US012590146B2

(12) United States Patent
Jheng et al.

(10) Patent No.: US 12,590,146 B2
(45) Date of Patent: Mar. 31, 2026

(54) CLDN18.2-TARGETING ANTIBODY, PREPARATION METHOD THEREFOR, AND USE THEREOF

(71) Applicant: NONA BIOSCIENCES (SUZHOU) CO., LTD., Suzhou (CN)

(72) Inventors: Ming-Jin Jheng, Suzhou (CN); Wei Zhang, Suzhou (CN); Jieli Wang, Suzhou (CN)

(73) Assignee: NONA BIOSCIENCES (SUZHOU) CO., LTD., Suzhou (CN)

( * ) Notice: Subject to any disclaimer, the term of this patent is extended or adjusted under 35 U.S.C. 154(b) by 1037 days.

(21) Appl. No.: 17/764,338

(22) PCT Filed: Sep. 29, 2020

(86) PCT No.: PCT/CN2020/118650
§ 371 (c)(1),
(2) Date: Mar. 28, 2022

(87) PCT Pub. No.: WO2021/063336
PCT Pub. Date: Apr. 8, 2021

(65) Prior Publication Data
US 2022/0332814 A1 Oct. 20, 2022

(30) Foreign Application Priority Data
Sep. 30, 2019 (CN) .......................... 201910941316.3

(51) Int. Cl.
| | |
|---|---|
| *C07K 16/28* | (2006.01) |
| *A61K 47/68* | (2017.01) |
| *A61P 35/00* | (2006.01) |
| *C12N 5/10* | (2006.01) |

(52) U.S. Cl.
CPC ........ *C07K 16/28* (2013.01); *A61K 47/68031* (2023.08); *A61K 47/6849* (2017.08); *A61P 35/00* (2018.01); *C12N 5/10* (2013.01)

(58) Field of Classification Search
CPC ................ C07K 16/28; C07K 2317/56; C07K 2317/565; C07K 2317/71; C07K 2317/72; C07K 2317/732; C07K 2317/734; C07K 2317/77; A61K 47/68031; A61K 47/6849; A61K 38/00; A61K 45/06; A61K 2039/505; A61P 35/00; C12N 5/10
USPC ...................................................... 424/133.1
See application file for complete search history.

(56) References Cited

U.S. PATENT DOCUMENTS

| | | | |
|---|---|---|---|
| 3,896,111 | A | 7/1975 | Kupchan et al. |
| 4,151,042 | A | 4/1979 | Higashide et al. |
| 7,750,116 | B1 | 7/2010 | Doronina et al. |
| 8,168,427 | B2 | 5/2012 | Sahin et al. |
| 9,433,675 | B2 | 9/2016 | Sahin et al. |
| 10,137,195 | B2 | 11/2018 | Sahin et al. |
| 10,421,817 | B1 | 9/2019 | Hu et al. |
| 10,858,415 | B2 | 12/2020 | Sahin et al. |
| 2018/0117174 | A1 | 5/2018 | Sahin et al. |
| 2020/0399364 | A1 | 12/2020 | Wang et al. |
| 2021/0009686 | A1 | 1/2021 | Song et al. |

FOREIGN PATENT DOCUMENTS

| | | |
|---|---|---|
| CN | 104427999 A | 3/2015 |
| CN | 103509110 B | 12/2015 |
| CN | 107667118 A | 2/2018 |
| CN | 109762067 A | 5/2019 |
| EP | 1948693 A1 | 7/2008 |
| EP | 3170842 A1 | 5/2017 |
| JP | 2009517354 A | 4/2009 |
| JP | 2017522024 A | 8/2017 |
| JP | 2018513146 A | 5/2018 |
| WO | WO-2014146672 A1 | 9/2014 |
| WO | WO-2015113576 A1 | 8/2015 |
| WO | WO-2019173420 A1 | 9/2019 |
| WO | WO-2019174617 A1 | 9/2019 |

OTHER PUBLICATIONS

Rudikoff et al (Proc. Natl. Acad. Sci. USA, 79(6):1979-1983, Mar. 1982).*
Colman P. M. (Research in Immunology, 145:33-36, 1994).*
Oct. 21, 2022 partial supplementary European Search Report issued in Patent Application of 20872423.7.
Oct. 18, 2024 First Office Action issued in Korean Patent Application No. 10-2022-7014720.
Oct. 14, 2024 Second Office Action issued in European Patent Application No. 20872423.7.
Dondelinger M, et al., "Understanding the Significance and Implications of Antibody Numbering and Antigen-Binding Surface/ Residue Definition". Frontiers in Immunology, Oct. 16, 2018;9:2278.
Jan. 5, 2021 International Search Report issued in International Patent Application No. PCT/CN2020/118650.
Jan. 5, 2021 Written Opinion of the International Searching Authority issued in International Patent Application No. PCT/CN2020/ 118650.
Feb. 21, 2022 Taiwan First Office Action issued in Patent Application of TW109133811.
Woll S. et al. "Claudin 18.2 is a target for IMAB362 antibody in pancreatic neoplasms" International Journal of Cancer, vol. 134, Dec. 31, 2014, pp. 731-739.

(Continued)

*Primary Examiner* — Yan Xiao
(74) *Attorney, Agent, or Firm* — Harness, Dickey & Pierce, P.L.C.

(57) ABSTRACT

Provided are a CLDN18.2-targeting antibody or an antigen-binding fragment thereof, a preparation method therefor, and the use thereof. The antibody comprises a light chain variable region and/or a heavy chain variable region, and the heavy chain variable region comprises HCDR1, HCDR2 and HCDR3, and the light chain variable region comprises LCDR1, LCDR2 and LCDR3. Compared with the prior art, the antibody has significant advantages in terms of binding affinity, ADCC, CDC, inhibitory effects on growth, endocytic activity, etc.

19 Claims, 15 Drawing Sheets
Specification includes a Sequence Listing.

(56) References Cited

OTHER PUBLICATIONS

Sahin U. et al. "Claudin-18 Splice Variant 2 Is a Pan-Cancer Target Suitable for Therapeutic Antibody Development" Clin. Cancer Res., vol. 14, No. 23, Dec. 1, 2008, pp. 7624-7634.

Jiang H. et al."Claudin18.2-Specific Chimeric Antigen Receptor Engineered T Cells for the Treatment of Gastric Cancer" Journal of the National Cancer Institute, vol. 111, No. 4, Sep. 6, 2018, pp. 409-418.

Front Pharmacol. Sep. 13, 2018; 9: 404.

Mol Cell Biol. Nov. 2001; 21(21):7380-90.

Eur J Cancer. Sep. 2018; 100:17-26.

JMol Biol 273:927-48, 1997.

Bird et al., Science 242:423-426 (1988).

Huston al., Proc. Natl. Acad. Sci. USA 85:5879-5883(1988).

Yu et al. (2002) PNAS 99: 7968-7973.

Jan. 26, 2023 European Search Report issued in Patent Application of EP20872423.7.

Feb. 7, 2023 First office action issued in Patent Application of EP20872423.7.

Mar. 20, 2023 First office action issued in Patent Application of JP2022-520345.

Jul. 28, 2023 First Office Action issued in Chinese Patent Application No. 202080068747.4.

Jul. 28, 2023 Search Report issued in Chinese Patent Application No. 202080068747.4.

Sep. 19, 2023 Second Office Action issued in Japanese Patent Application No. 2022-520345.

Jun. 4, 2024 Second Office Action issued in Chinese Patent Application No. 2020800687474.

* cited by examiner

A    HEK293 hCLDN18.2

B    NUGC4 D8

C    HEK293 hCLDN18.1

SEQUENCE LISTING

<160> NUMBER OF SEQ ID NOS: 98

<210> SEQ ID NO 1

-continued

```
<211> LENGTH: 25
<212> TYPE: PRT
<213> ORGANISM: Artificial Sequence
<220> FEATURE:
<223> OTHER INFORMATION: Antibody PR000400 HFWR1 Chothia

<400> SEQUENCE: 1

Gln Val Gln Leu Gln Gln Pro Gly Ala Glu Leu Val Arg Pro Gly Ala
1               5                   10                  15

Ser Val Lys Leu Ser Cys Lys Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Antibody PR002725 HFWR1 Chothia, Antibody
      PR002726 HFWR1 Chothia, Antibody PR003197 HFWR1 Chothia

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: Antibody PR002727 HFWR1 Chothia, Antibody
      PR003240 HFWR1 Chothia, Antibody PR003894 HFWR1 Chothia

<400> SEQUENCE: 3

Glu Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: Antibody PR003289 HFWR1 Chothia, Antibody
      PR003890 HFWR1 Chothia, Antibody PR003897 HFWR1 Chothia

<400> SEQUENCE: 4

Gln Val Gln Leu Val Glu Ser Gly Gly Gly Leu Val Gln Pro Gly Gly
1               5                   10                  15

Ser Leu Arg Leu Ser Cys Ala Thr Ser
            20                  25

<210> SEQ ID NO 5
<211> LENGTH: 7
<212> TYPE: PRT
<213> ORGANISM: Artificial Sequence
<220> FEATURE:
<223> OTHER INFORMATION: Antibody PR000400 HCDR1 Chothia

<400> SEQUENCE: 5

Gly Tyr Thr Phe Thr Ser Tyr
1               5
```

-continued

```
<210> SEQ ID NO 6
<211> LENGTH: 7
<212> TYPE: PRT
<213> ORGANISM: Artificial Sequence
<220> FEATURE:
<223> OTHER INFORMATION: Antibody PR002725 HCDR1 Chothia

<400> SEQUENCE: 6

Gly Phe Thr Phe Ser Gly Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: Antibody PR002726 HCDR1 Chothia, Antibody
      PR003197 HCDR1 Chothia, Antibody PR003292 HCDR1 Chothia

<400> SEQUENCE: 7

Gly Phe Thr Phe Ser Ser Phe
1               5

<210> SEQ ID NO 8
<211> LENGTH: 7
<212> TYPE: PRT
<213> ORGANISM: Artificial Sequence
<220> FEATURE:
<223> OTHER INFORMATION: Antibody PR002727 HCDR1 Chothia, Antibody
      PR003240 HCDR1 Chothia, Antibody PR003289 HCDR1 Chothia

<400> SEQUENCE: 8

Gly Phe Thr Phe Ser Ser Tyr
1               5

<210> SEQ ID NO 9
<211> LENGTH: 19
<212> TYPE: PRT
<213> ORGANISM: Artificial Sequence
<220> FEATURE:
<223> OTHER INFORMATION: Antibody PR000400 HFWR2 Chothia

<400> SEQUENCE: 9

Trp Ile Asn Trp Val Lys Gln Arg Pro Gly Gln Gly Leu Glu Trp Ile
1               5                   10                  15

Gly Asn Ile

<210> SEQ ID NO 10
<211> LENGTH: 19
<212> TYPE: PRT
<213> ORGANISM: Artificial Sequence
<220> FEATURE:
<223> OTHER INFORMATION: Antibody PR002725 HFWR2 Chothia

<400> SEQUENCE: 10

Val Met Ser Trp Val Arg Gln Ala Pro Gly Lys Gly Leu Glu Trp Val
1               5                   10                  15

Ser Ala Ile

<210> SEQ ID NO 11
<211> LENGTH: 19
<212> TYPE: PRT
<213> ORGANISM: Artificial Sequence
<220> FEATURE:
<223> OTHER INFORMATION: Antibody PR002726 HFWR2 Chothia, Antibody
      PR003197 HFWR2 Chothia, Antibody PR003292 HFWR2 Chothia
```

-continued

```
<400> SEQUENCE: 11

Val Met Ser Trp Val Arg Gln Ala Pro Gly Lys Gly Leu Glu Trp Val
1               5                   10                  15

Ser Thr Ile

<210> SEQ ID NO 12
<211> LENGTH: 19
<212> TYPE: PRT
<213> ORGANISM: Artificial Sequence
<220> FEATURE:
<223> OTHER INFORMATION: Antibody PR002727 HFWR2 Chothia, Antibody
      PR003240 HFWR2 Chothia, Antibody PR003894 HFWR2 Chothia

<400> SEQUENCE: 12

Gly Met His Trp Val Arg Gln Ala Pro Gly Lys Gly Leu Glu Trp Val
1               5                   10                  15

Ala Val Ile

<210> SEQ ID NO 13
<211> LENGTH: 19
<212> TYPE: PRT
<213> ORGANISM: Artificial Sequence
<220> FEATURE:
<223> OTHER INFORMATION: Antibody PR003289 HFWR2 Chothia, Antibody
      PR003890 HFWR2 Chothia, Antibody PR003897 HFWR2 Chothia

<400> SEQUENCE: 13

Ala Met Ser Trp Val Arg Gln Ala Pro Gly Lys Gly Leu Glu Trp Val
1               5                   10                  15

Ser Leu Ile

<210> SEQ ID NO 14
<211> LENGTH: 19
<212> TYPE: PRT
<213> ORGANISM: Artificial Sequence
<220> FEATURE:
<223> OTHER INFORMATION: Antibody PR003291 HFWR2 Chothia, Antibody
      PR003891 HFWR2 Chothia, Antibody PR003898 HFWR2 Chothia

<400> SEQUENCE: 14

Ala Met Ser Trp Val Arg Gln Ala Pro Gly Lys Gly Leu Glu Trp Val
1               5                   10                  15

Ser Ala Ile

<210> SEQ ID NO 15
<211> LENGTH: 6
<212> TYPE: PRT
<213> ORGANISM: Artificial Sequence
<220> FEATURE:
<223> OTHER INFORMATION: Antibody PR000400 HCDR2 Chothia

<400> SEQUENCE: 15

Tyr Pro Ser Asp Ser Tyr
1               5

<210> SEQ ID NO 16
<211> LENGTH: 6
<212> TYPE: PRT
<213> ORGANISM: Artificial Sequence
<220> FEATURE:
<223> OTHER INFORMATION: Antibody PR002725 HCDR2 Chothia, Antibody
      PR003289 HCDR2 Chothia, Antibody PR003291 HCDR2 Chothia

<400> SEQUENCE: 16
```

-continued

```
Ser Gly Ser Gly Gly Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Antibody PR002726 HCDR2 Chothia, Antibody
      PR003197 HCDR2 Chothia, Antibody PR003292 HCDR2 Chothia

<400> SEQUENCE: 17

Ser Gly Ser Gly Arg Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Antibody PR002727 HCDR2 Chothia

<400> SEQUENCE: 18

Trp Tyr Asp Gly Ser Asn
1               5

<210> SEQ ID NO 19
<211> LENGTH: 6
<212> TYPE: PRT
<213> ORGANISM: Artificial Sequence
<220> FEATURE:
<223> OTHER INFORMATION: Antibody PR003240 HCDR2 Chothia, Antibody
      PR003894 HCDR2 Chothia

<400> SEQUENCE: 19

Trp Tyr Glu Gly Ser Asn
1               5

<210> SEQ ID NO 20
<211> LENGTH: 41
<212> TYPE: PRT
<213> ORGANISM: Artificial Sequence
<220> FEATURE:
<223> OTHER INFORMATION: Antibody PR000400 HFWR3 Chothia

<400> SEQUENCE: 20

Thr Asn Tyr Asn Gln Lys Phe Lys Asp Lys Ala Thr Leu Thr Val Asp
1               5                   10                  15

Lys Ser Ser Ser Thr Ala Tyr Met Gln Leu Ser Ser Pro Thr Ser Glu
            20                  25                  30

Asp Ser Ala Val Tyr Tyr Cys Thr Arg
        35                  40

<210> SEQ ID NO 21
<211> LENGTH: 41
<212> TYPE: PRT
<213> ORGANISM: Artificial Sequence
<220> FEATURE:
<223> OTHER INFORMATION: Antibody PR002725 HFWR3 Chothia, Antibody
      PR002727 HFWR3 Chothia, Antibody PR003240 HFWR3 Chothia

<400> SEQUENCE: 21

Lys Tyr Tyr Ala Asp Ser Val Lys Gly Arg Phe Thr Ile Ser Arg Asp
1               5                   10                  15

Asn Ser Lys Asn Thr Leu Tyr Leu Gln Met Asn Ser Leu Arg Ala Glu
            20                  25                  30
```

-continued

Asp Thr Ala Val Tyr Tyr Cys Ala Lys
        35                  40

<210> SEQ ID NO 22
<211> LENGTH: 41
<212> TYPE: PRT
<213> ORGANISM: Artificial Sequence
<220> FEATURE:
<223> OTHER INFORMATION: Antibody PR002726 HFWR3 Chothia, Antibody
      PR003197 HFWR3 Chothia, Antibody PR003292 HFWR3 Chothia

<400> SEQUENCE: 22

Thr Tyr Tyr Ala Asp Ser Val Lys Gly Arg Phe Thr Ile Ser Arg Asp
1               5                   10                  15

Asn Ser Lys Asn Thr Leu His Leu Gln Met Asn Ser Leu Arg Ala Glu
            20                  25                  30

Asp Thr Ala Val Tyr Tyr Cys Ala Lys
        35                  40

<210> SEQ ID NO 23
<211> LENGTH: 41
<212> TYPE: PRT
<213> ORGANISM: Artificial Sequence
<220> FEATURE:
<223> OTHER INFORMATION: Antibody PR003289 HFWR3 Chothia, Antibody
      PR003890 HFWR3 Chothia, Antibody PR003897 HFWR3 Chothia

<400> SEQUENCE: 23

Pro Tyr Tyr Ala Asp Ser Val Lys Gly Arg Phe Thr Ile Ser Arg Asp
1               5                   10                  15

Asn Ser Lys Asn Thr Leu Tyr Leu Gln Met Asn Ser Leu Arg Ala Glu
            20                  25                  30

Asp Thr Ala Val Tyr Tyr Cys Ala Lys
        35                  40

<210> SEQ ID NO 24
<211> LENGTH: 41
<212> TYPE: PRT
<213> ORGANISM: Artificial Sequence
<220> FEATURE:
<223> OTHER INFORMATION: Antibody PR003291 HFWR3 Chothia, Antibody
      PR003891 HFWR3 Chothia, Antibody PR003898 HFWR3 Chothia

<400> SEQUENCE: 24

Thr Tyr Tyr Ala Asp Ser Val Lys Gly Arg Phe Thr Ile Ser Arg Asp
1               5                   10                  15

Asn Ser Lys Asn Thr Leu Tyr Leu Gln Met Asn Ser Leu Arg Ala Glu
            20                  25                  30

Asp Thr Ala Val Tyr Tyr Cys Ala Lys
        35                  40

<210> SEQ ID NO 25
<211> LENGTH: 9
<212> TYPE: PRT
<213> ORGANISM: Artificial Sequence
<220> FEATURE:
<223> OTHER INFORMATION: Antibody PR000400 HCDR3 Chothia

<400> SEQUENCE: 25

Ser Trp Arg Gly Asn Ser Phe Asp Tyr
1               5

<210> SEQ ID NO 26

```
<211> LENGTH: 10
<212> TYPE: PRT
<213> ORGANISM: Artificial Sequence
<220> FEATURE:
<223> OTHER INFORMATION: Antibody PR002725 HCDR3 Chothia

<400> SEQUENCE: 26

Gly Asp Ile Ala Val Leu Leu Phe Asp Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Antibody PR002726 HCDR3 Chothia, Antibody
      PR003197 HCDR3 Chothia, Antibody PR003292 HCDR3 Chothia

<400> SEQUENCE: 27

Asp Ala Ala Ala Ala Gly Thr Lys Phe Asp Tyr
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Antibody PR002727 HCDR3 Chothia, Antibody
      PR003240 HCDR3 Chothia, Antibody PR003894 HCDR3 Chothia

<400> SEQUENCE: 28

Asp Gly Tyr Tyr Gly Ser Gly Thr Tyr Tyr Tyr Val Met Asn Ala
1               5                   10                  15

<210> SEQ ID NO 29
<211> LENGTH: 11
<212> TYPE: PRT
<213> ORGANISM: Artificial Sequence
<220> FEATURE:
<223> OTHER INFORMATION: Antibody PR003289 HCDR3 Chothia, Antibody
      PR003291 HCDR3 Chothia, Antibody PR003890 HCDR3 Chothia

<400> SEQUENCE: 29

Gly Val Val Asn Trp Gly Ser Leu Phe Asp Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Antibody PR000400 HFWR4 Chothia

<400> SEQUENCE: 30

Trp Gly Gln Gly Thr Thr Leu Thr Val Ser Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Antibody PR002725 HFWR4 Chothia, Antibody
      PR002726 HFWR4 Chothia, Antibody PR003197 HFWR4 Chothia

<400> SEQUENCE: 31

Trp Gly Gln Gly Thr Leu Val Thr Val Ser Ser
1               5                   10
```

```
<210> SEQ ID NO 32
<211> LENGTH: 11
<212> TYPE: PRT
<213> ORGANISM: Artificial Sequence
<220> FEATURE:
<223> OTHER INFORMATION: Antibody PR002727 HFWR4 Chothia, Antibody
      PR003240 HFWR4 Chothia, Antibody PR003894 HFWR4 Chothia

<400> SEQUENCE: 32

Trp Gly Gln Gly Ala Ser Val Thr Val Ser Ser
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Antibody PR003291 HFWR4 Chothia, Antibody
      PR003891 HFWR4 Chothia, Antibody PR003898 HFWR4 Chothia

<400> SEQUENCE: 33

Trp Gly Gln Gly Thr Leu Val Thr Phe Ser Ser
1               5                   10

<210> SEQ ID NO 34
<211> LENGTH: 23
<212> TYPE: PRT
<213> ORGANISM: Artificial Sequence
<220> FEATURE:
<223> OTHER INFORMATION: Antibody PR000400 LFWR1 Chothia

<400> SEQUENCE: 34

Asp Ile Val Met Thr Gln Ser Pro Ser Ser Leu Thr Val Thr Ala Gly
1               5                   10                  15

Glu Lys Val Thr Met Ser Cys
            20

<210> SEQ ID NO 35
<211> LENGTH: 23
<212> TYPE: PRT
<213> ORGANISM: Artificial Sequence
<220> FEATURE:
<223> OTHER INFORMATION: Antibody PR002725 LFWR1 Chothia

<400> SEQUENCE: 35

Glu Met Val Met Thr Gln Ser Pro Ala Thr Leu Ser Val Ser Pro Gly
1               5                   10                  15

Glu Arg Ala Thr Leu Ser Cys
            20

<210> SEQ ID NO 36
<211> LENGTH: 23
<212> TYPE: PRT
<213> ORGANISM: Artificial Sequence
<220> FEATURE:
<223> OTHER INFORMATION: Antibody PR002726 LFWR1 Chothia, Antibody
      PR003197 LFWR1 Chothia, Antibody PR003292 LFWR1 Chothia

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys
            20
```

<210> SEQ ID NO 37
<211> LENGTH: 23
<212> TYPE: PRT
<213> ORGANISM: Artificial Sequence
<220> FEATURE:
<223> OTHER INFORMATION: Antibody PR002727 LFWR1 Chothia, Antibody
      PR003240 LFWR1 Chothia, Antibody PR003894 LFWR1 Chothia

<400> SEQUENCE: 37

Glu Ile Val Met Thr Gln Ser Pro Ala Thr Leu Ser Val Ser Pro Gly
1               5                   10                  15

Glu Arg Val Thr Leu Ser Cys
            20

<210> SEQ ID NO 38
<211> LENGTH: 23
<212> TYPE: PRT
<213> ORGANISM: Artificial Sequence
<220> FEATURE:
<223> OTHER INFORMATION: Antibody PR003289 LFWR1 Chothia, Antibody
      PR003291 LFWR1 Chothia, Antibody PR003890 LFWR1 Chothia

<400> SEQUENCE: 38

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 39
<211> LENGTH: 17
<212> TYPE: PRT
<213> ORGANISM: Artificial Sequence
<220> FEATURE:
<223> OTHER INFORMATION: Antibody PR000400 LCDR1 Chothia

<400> SEQUENCE: 39

Lys Ser Ser Gln Ser Leu Leu Asn Ser Gly Asn Gln Lys Asn Tyr Leu
1               5                   10                  15

Thr

<210> SEQ ID NO 40
<211> LENGTH: 11
<212> TYPE: PRT
<213> ORGANISM: Artificial Sequence
<220> FEATURE:
<223> OTHER INFORMATION: Antibody PR002725 LCDR1 Chothia

<400> SEQUENCE: 40

Arg Ala Ser Gln Ser Val Ser Arg Asn Leu Ala
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Antibody PR002726 LCDR1 Chothia, Antibody
      PR003197 LCDR1 Chothia, Antibody PR003292 LCDR1 Chothia

<400> SEQUENCE: 41

Arg Ala Ser Gln Ser Val Ser Ser Tyr Leu Ala
1               5                   10

<210> SEQ ID NO 42
<211> LENGTH: 11
<212> TYPE: PRT

-continued

```
<213> ORGANISM: Artificial Sequence
<220> FEATURE:
<223> OTHER INFORMATION: Antibody PR002727 LCDR1 Chothia, Antibody
      PR003240 LCDR1 Chothia, Antibody PR003289 LCDR1 Chothia

<400> SEQUENCE: 42

Arg Ala Ser Gln Ser Val Ser Ser Asn Leu Ala
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Antibody PR000400 LFWR2 Chothia

<400> SEQUENCE: 43

Trp Tyr Gln Gln Lys Pro Gly Gln Pro Pro Lys Leu Leu Ile Tyr
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Antibody PR002725 LFWR2 Chothia

<400> SEQUENCE: 44

Trp Phe Gln Gln Lys Pro Gly Gln Ala Pro Arg Leu Leu Ile Tyr
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Antibody PR002726 LFWR2 Chothia, Antibody
      PR002727 LFWR2 Chothia, Antibody PR003197 LFWR2 Chothia

<400> SEQUENCE: 45

Trp Tyr Gln Gln Lys Pro Gly Gln Ala Pro Arg Leu Leu Ile Tyr
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: Antibody PR000400 LCDR2 Chothia

<400> SEQUENCE: 46

Trp Ala Ser Thr Arg Glu Ser
1               5

<210> SEQ ID NO 47
<211> LENGTH: 7
<212> TYPE: PRT
<213> ORGANISM: Artificial Sequence
<220> FEATURE:
<223> OTHER INFORMATION: Antibody PR002725 LCDR2 Chothia, Antibody
      PR002727 LCDR2 Chothia, Antibody PR003240 LCDR2 Chothia

<400> SEQUENCE: 47

Gly Ala Ser Thr Arg Ala Thr
1               5

<210> SEQ ID NO 48
```

-continued

```
<211> LENGTH: 7
<212> TYPE: PRT
<213> ORGANISM: Artificial Sequence
<220> FEATURE:
<223> OTHER INFORMATION: Antibody PR002726 LCDR2 Chothia, Antibody
      PR003197 LCDR2 Chothia, Antibody PR003292 LCDR2 Chothia

<400> SEQUENCE: 48

Asp Ala Ser Asn Arg Ala Thr
1               5

<210> SEQ ID NO 49
<211> LENGTH: 32
<212> TYPE: PRT
<213> ORGANISM: Artificial Sequence
<220> FEATURE:
<223> OTHER INFORMATION: Antibody PR000400 LFWR3 Chothia

<400> SEQUENCE: 49

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Antibody PR002725 LFWR3 Chothia, Antibody
      PR002727 LFWR3 Chothia, Antibody PR003240 LFWR3 Chothia

<400> SEQUENCE: 50

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Antibody PR002726 LFWR3 Chothia, Antibody
      PR003197 LFWR3 Chothia, Antibody PR003292 LFWR3 Chothia

<400> SEQUENCE: 51

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Antibody PR003289 LFWR3 Chothia, Antibody
      PR003890 LFWR3 Chothia, Antibody PR003897 LFWR3 Chothia

<400> SEQUENCE: 52

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Asp Cys
            20                  25                  30
```

-continued

```
<210> SEQ ID NO 53
<211> LENGTH: 32
<212> TYPE: PRT
<213> ORGANISM: Artificial Sequence
<220> FEATURE:
<223> OTHER INFORMATION: Antibody PR003291 LFWR3 Chothia, Antibody
      PR003891 LFWR3 Chothia, Antibody PR003898 LFWR3 Chothia

<400> SEQUENCE: 53

Gly Ile Pro Ala Arg Phe Ser Gly Ser Gly Ser Gly Thr Glu Phe Thr
1               5                   10                  15

Leu Thr Ile Ser Ser Leu Gln Ser Asp Asp Phe Ala Val Tyr Tyr Cys
            20                  25                  30

<210> SEQ ID NO 54
<211> LENGTH: 9
<212> TYPE: PRT
<213> ORGANISM: Artificial Sequence
<220> FEATURE:
<223> OTHER INFORMATION: Antibody PR000400 LCDR3 Chothia

<400> SEQUENCE: 54

Gln Asn Asp Tyr Ser Tyr Pro Phe Thr
1               5

<210> SEQ ID NO 55
<211> LENGTH: 9
<212> TYPE: PRT
<213> ORGANISM: Artificial Sequence
<220> FEATURE:
<223> OTHER INFORMATION: Antibody PR002725 LCDR3 Chothia, Antibody
      PR003289 LCDR3 Chothia, Antibody PR003890 LCDR3 Chothia

<400> SEQUENCE: 55

Gln Gln Tyr Asn Asn Trp Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Antibody PR002726 LCDR3 Chothia, Antibody
      PR003197 LCDR3 Chothia, Antibody PR003292 LCDR3 Chothia

<400> SEQUENCE: 56

Gln Gln Arg Ser Asn Trp Pro Leu Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Antibody PR002727 LCDR3 Chothia, Antibody
      PR003240 LCDR3 Chothia, Antibody PR003894 LCDR3 Chothia

<400> SEQUENCE: 57

Gln Gln Tyr Asn Tyr Trp Pro Leu Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Antibody PR003291 LCDR3 Chothia, Antibody
```

PR003891 LCDR3 Chothia, Antibody PR003898 LCDR3 Chothia

<400> SEQUENCE: 58

Gln Gln Asn Asn Asn Trp Pro Leu Thr
1               5

<210> SEQ ID NO 59
<211> LENGTH: 10
<212> TYPE: PRT
<213> ORGANISM: Artificial Sequence
<220> FEATURE:
<223> OTHER INFORMATION: Antibody PR000400 LFWR4 Chothia

<400> SEQUENCE: 59

Phe Gly Ser Gly Thr Lys Leu Glu Ile Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Antibody PR002725 LFWR4 Chothia, Antibody
      PR002726 LFWR4 Chothia, Antibody PR002727 LFWR4 Chothia

<400> SEQUENCE: 60

Phe Gly Gly Gly Thr Lys Val Glu Ile Lys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Antibody PR003289 LFWR4 Chothia, Antibody
      PR003890 LFWR4 Chothia, Antibody PR003897 LFWR4 Chothia

<400> SEQUENCE: 61

Phe Gly Gln Gly Thr Lys Val Glu Ile Lys
1               5                   10

<210> SEQ ID NO 62
<211> LENGTH: 118
<212> TYPE: PRT
<213> ORGANISM: Artificial Sequence
<220> FEATURE:
<223> OTHER INFORMATION: Antibody PR000400 VH

<400> SEQUENCE: 62

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: Antibody PR002725 VH

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Val Met Ser Trp Val Arg Gln Ala Pro Gly Lys Gly Leu Glu Trp Val
        35                  40                  45

Ser Ala Ile Ser Gly Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Ile Ala Val Leu Leu Phe Asp Tyr Trp Gly Gln Gly
            100                 105                 110

Thr Leu Val Thr Val Ser Ser
        115

<210> SEQ ID NO 64
<211> LENGTH: 120
<212> TYPE: PRT
<213> ORGANISM: Artificial Sequence
<220> FEATURE:
<223> OTHER INFORMATION: Antibody PR002726 VH, Antibody PR003197 VH,
      Antibody PR003292 VH, Antibody PR003293 VH, Antibody PR003340 VH

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Val Met Ser Trp Val Arg Gln Ala Pro Gly Lys Gly Leu Glu Trp Val
        35                  40                  45

Ser Thr Ile Ser Gly Ser Gly Arg Ser Thr Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Lys Asp Ala Ala Ala Ala Gly Thr Lys Phe Asp Tyr Trp Gly Gln
            100                 105                 110

Gly Thr Leu Val Thr Val Ser Ser
        115                 120

<210> SEQ ID NO 65
<211> LENGTH: 125
<212> TYPE: PRT
<213> ORGANISM: Artificial Sequence
<220> FEATURE:
<223> OTHER INFORMATION: Antibody PR002727 VH

<400> SEQUENCE: 65

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Tyr Tyr Gly Ser Gly Thr Tyr Tyr Tyr Val Met
            100                 105                 110

Asn Ala Trp Gly Gln Gly Ala Ser Val Thr Val Ser Ser
        115                 120                 125

<210> SEQ ID NO 66
<211> LENGTH: 125
<212> TYPE: PRT
<213> ORGANISM: Artificial Sequence
<220> FEATURE:
<223> OTHER INFORMATION: Antibody PR003240 VH, Antibody PR003894 VH

<400> SEQUENCE: 66

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Tyr Tyr Gly Ser Gly Thr Tyr Tyr Tyr Val Met
            100                 105                 110

Asn Ala Trp Gly Gln Gly Ala Ser Val Thr Val Ser Ser
        115                 120                 125

<210> SEQ ID NO 67
<211> LENGTH: 120
<212> TYPE: PRT
<213> ORGANISM: Artificial Sequence
<220> FEATURE:
<223> OTHER INFORMATION: Antibody PR003289 VH, Antibody PR003890 VH,
      Antibody PR003897 VH

<400> SEQUENCE: 67

Gln Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Val Arg Gln Ala Pro Gly Lys Gly Leu Glu Trp Val

-continued

```
                35                  40                  45

Ser Leu Ile Ser Gly Ser Gly Gly Ser Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Val Asn Trp Gly Ser Leu Phe Asp Tyr Trp Gly Gln
                100                 105                 110

Gly Thr Leu Val Thr Val Ser Ser
        115                 120

<210> SEQ ID NO 68
<211> LENGTH: 120
<212> TYPE: PRT
<213> ORGANISM: Artificial Sequence
<220> FEATURE:
<223> OTHER INFORMATION: Antibody PR003291 VH, Antibody PR003891 VH,
      Antibody PR003898 VH

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Val Asn Trp Gly Ser Leu Phe Asp Tyr Trp Gly Gln
                100                 105                 110

Gly Thr Leu Val Thr Phe Ser Ser
        115                 120

<210> SEQ ID NO 69
<211> LENGTH: 113
<212> TYPE: PRT
<213> ORGANISM: Artificial Sequence
<220> FEATURE:
<223> OTHER INFORMATION: Antibody PR000400 VL

<400> SEQUENCE: 69

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95
```

-continued

```
Asp Tyr Ser Tyr Pro Phe Thr Phe Gly Ser Gly Thr Lys Leu Glu Ile
            100                 105                 110

Lys

<210> SEQ ID NO 70
<211> LENGTH: 107
<212> TYPE: PRT
<213> ORGANISM: Artificial Sequence
<220> FEATURE:
<223> OTHER INFORMATION: Antibody PR002725 VL

<400> SEQUENCE: 70

Glu Met Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
            85                  90                  95

Thr Phe Gly Gly Gly Thr Lys Val Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: Antibody PR002726 VL, Antibody PR003197 VL,
      Antibody PR003292 VL, Antibody PR003293 VL, Antibody PR003340 VL

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
            85                  90                  95

Thr Phe Gly Gly Gly Thr Lys Val Glu Ile Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: Antibody PR002727 VL, Antibody PR003240 VL,
      Antibody PR003894 VL

<400> SEQUENCE: 72
```

```
Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Tyr Trp Pro Leu
                85                  90                  95

Thr Phe Gly Gly Gly Thr Lys Val Glu Ile Lys
            100                 105
```

<210> SEQ ID NO 73
<211> LENGTH: 107
<212> TYPE: PRT
<213> ORGANISM: Artificial Sequence
<220> FEATURE:
<223> OTHER INFORMATION: Antibody PR003289 VL, Antibody PR003890 VL,
      Antibody PR003897 VL

<400> SEQUENCE: 73

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Asp Cys Gln Gln Tyr Asn Asn Trp Pro Leu
                85                  90                  95

Thr Phe Gly Gln Gly Thr Lys Val Glu Ile Lys
            100                 105
```

<210> SEQ ID NO 74
<211> LENGTH: 107
<212> TYPE: PRT
<213> ORGANISM: Artificial Sequence
<220> FEATURE:
<223> OTHER INFORMATION: Antibody PR003291 VL, Antibody PR003891 VL,
      Antibody PR003898 VL

<400> SEQUENCE: 74

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80
```

```
Asp Asp Phe Ala Val Tyr Tyr Cys Gln Gln Asn Asn Asn Trp Pro Leu
            85                  90                  95

Thr Phe Gly Gly Gly Thr Lys Val Glu Ile Lys
            100                 105

<210> SEQ ID NO 75
<211> LENGTH: 448
<212> TYPE: PRT
<213> ORGANISM: Artificial Sequence
<220> FEATURE:
<223> OTHER INFORMATION: Antibody PR000400 HC

<400> SEQUENCE: 75

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
            85                  90                  95

Thr Arg Ser Trp Arg Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335
```

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 76
<211> LENGTH: 449
<212> TYPE: PRT
<213> ORGANISM: Artificial Sequence
<220> FEATURE:
<223> OTHER INFORMATION: Antibody PR002725 HC

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Val Met Ser Trp Val Arg Gln Ala Pro Gly Lys Gly Leu Glu Trp Val
            35                  40                  45

Ser Ala Ile Ser Gly Ser Gly Gly Ser Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Ile Ala Val Leu Leu Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

-continued

```
Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

```
<210> SEQ ID NO 77
<211> LENGTH: 450
<212> TYPE: PRT
<213> ORGANISM: Artificial Sequence
<220> FEATURE:
<223> OTHER INFORMATION: Antibody PR002726 HC

<400> SEQUENCE: 77
```

```
Glu Val Gln Leu Leu Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Phe
        20                  25                  30

Val Met Ser Trp Val Arg Gln Ala Pro Gly Lys Gly Leu Glu Trp Val
        35                  40                  45

Ser Thr Ile Ser Gly Ser Gly Arg Ser Thr Tyr Tyr Ala Asp Ser Val
        50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Lys Asp Ala Ala Ala Ala Gly Thr Lys Phe Asp Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160
```

-continued

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450
```

```
<210> SEQ ID NO 78
<211> LENGTH: 455
<212> TYPE: PRT
<213> ORGANISM: Artificial Sequence
<220> FEATURE:
<223> OTHER INFORMATION: Antibody PR002727 HC

<400> SEQUENCE: 78
```

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
        50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Tyr Tyr Gly Ser Gly Thr Tyr Tyr Tyr Val Met
                100                 105                 110

Asn Ala Trp Gly Gln Gly Ala Ser Val Thr Val Ser Ser Ala Ser Thr
                115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
    450                 455
```

<210> SEQ ID NO 79
<211> LENGTH: 450
<212> TYPE: PRT

<213> ORGANISM: Artificial Sequence
<220> FEATURE:
<223> OTHER INFORMATION: Antibody PR003197 HC

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Val Met Ser Trp Val Arg Gln Ala Pro Gly Lys Gly Leu Glu Trp Val
            35                  40                  45

Ser Thr Ile Ser Gly Ser Gly Arg Ser Thr Tyr Tyr Ala Asp Ser Val
        50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Lys Asp Ala Ala Ala Ala Gly Thr Lys Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val

-continued

```
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 80
<211> LENGTH: 455
<212> TYPE: PRT
<213> ORGANISM: Artificial Sequence
<220> FEATURE:
<223> OTHER INFORMATION: Antibody PR003240 HC

<400> SEQUENCE: 80

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Tyr Tyr Gly Ser Gly Thr Tyr Tyr Tyr Val Met
            100                 105                 110

Asn Ala Trp Gly Gln Gly Ala Ser Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Asp Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
```

-continued

```
                    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                    325                 330                 335

Pro Ala Pro Glu Glu Lys Thr Ile Ser Lys Ala Lys Gly Gln Pro Arg
                    340                 345                 350

Glu Pro Gln Val Tyr Thr Leu Pro Pro Ser Arg Glu Glu Met Thr Lys
                    355                 360                 365

Asn Gln Val Ser Leu Thr Cys Leu Val Lys Gly Phe Tyr Pro Ser Asp
                    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                    420                 425                 430

Cys Ser Val Met His Glu Ala Leu His Asn His Tyr Thr Gln Lys Ser
                    435                 440                 445

Leu Ser Leu Ser Pro Gly Lys
    450                 455

<210> SEQ ID NO 81
<211> LENGTH: 450
<212> TYPE: PRT
<213> ORGANISM: Artificial Sequence
<220> FEATURE:
<223> OTHER INFORMATION: Antibody PR003289 HC

<400> SEQUENCE: 81

Gln Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Leu Ile Ser Gly Ser Gly Gly Ser Pro Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Val Asn Trp Gly Ser Leu Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
```

-continued

```
                195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
    435                 440                 445
Gly Lys
    450
```

```
<210> SEQ ID NO 82
<211> LENGTH: 450
<212> TYPE: PRT
<213> ORGANISM: Artificial Sequence
<220> FEATURE:
<223> OTHER INFORMATION: Antibody PR003291 HC

<400> SEQUENCE: 82

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Val Val Asn Trp Gly Ser Leu Phe Asp Tyr Trp Gly Gln
```

-continued

```
                 100                 105                 110
Gly Thr Leu Val Thr Phe Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 83
<211> LENGTH: 450
<212> TYPE: PRT
<213> ORGANISM: Artificial Sequence
<220> FEATURE:
<223> OTHER INFORMATION: Antibody PR003292 HC

<400> SEQUENCE: 83

Glu Val Gln Leu Leu Glu Ser Gly Gly Gly Leu Val Gln Pro Gly Gly
```

-continued

```
 1                5                10               15

Ser Leu Arg Leu Ser Cys Ala Ala Ser Gly Phe Thr Phe Ser Ser Phe
             20              25              30

Val Met Ser Trp Val Arg Gln Ala Pro Gly Lys Gly Leu Glu Trp Val
             35              40              45

Ser Thr Ile Ser Gly Ser Gly Arg Ser Thr Tyr Tyr Ala Asp Ser Val
             50              55              60

Lys Gly Arg Phe Thr Ile Ser Arg Asp Asn Ser Lys Asn Thr Leu His
65               70              75              80

Leu Gln Met Asn Ser Leu Arg Ala Glu Asp Thr Ala Val Tyr Tyr Cys
             85              90              95

Ala Lys Asp Ala Ala Ala Ala Gly Thr Lys Phe Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
            130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
            210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Tyr Ile
            245             250             255

Thr Arg Glu Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Asn Ser Thr Tyr Arg
            290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
            355             360             365

Thr Cys Leu Val Lys Gly Phe Tyr Pro Ser Asp Ile Ala Val Glu Trp
            370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430
```

-continued

```
Glu Ala Leu His Asn His Tyr Thr Gln Lys Ser Leu Ser Leu Ser Pro
        435                 440                 445

Gly Lys
    450

<210> SEQ ID NO 84
<211> LENGTH: 450
<212> TYPE: PRT
<213> ORGANISM: Artificial Sequence
<220> FEATURE:
<223> OTHER INFORMATION: Antibody PR003293 HC

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Val Met Ser Trp Val Arg Gln Ala Pro Gly Lys Gly Leu Glu Trp Val
            35                  40                  45

Ser Thr Ile Ser Gly Ser Gly Arg Ser Thr Tyr Tyr Ala Asp Ser Val
        50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Lys Asp Ala Ala Ala Ala Gly Thr Lys Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335
```

-continued

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

```
<210> SEQ ID NO 85
<211> LENGTH: 450
<212> TYPE: PRT
<213> ORGANISM: Artificial Sequence
<220> FEATURE:
<223> OTHER INFORMATION: Antibody PR003340 HC

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Val Met Ser Trp Val Arg Gln Ala Pro Gly Lys Gly Leu Glu Trp Val
            35                  40                  45

Ser Thr Ile Ser Gly Ser Gly Arg Ser Thr Tyr Tyr Ala Asp Ser Val
            50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Lys Asp Ala Ala Ala Ala Gly Thr Lys Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240
```

-continued

```
Pro Asp Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Gln Phe Asn Trp Tyr Val Asp Gly Val Glu Val His
            275             280             285

Asn Ala Lys Thr Lys Pro Arg Glu Glu Gln Phe Asn Ser Thr Phe Arg
    290             295             300

Val Val Ser Val Leu Thr Val Val His Gln Asp Trp Leu Asn Gly Lys
305             310             315             320

Glu Tyr Lys Cys Lys Val Ser Asn Lys Ala Leu Pro Ala Pro Glu Glu
            325             330             335

Lys Thr Ile Ser Lys Thr Lys Gly Gln Pro Arg Glu Pro Gln Val Tyr
            340             345             350

Thr Leu Pro Pro Ser Arg Glu Glu Met Thr Lys Asn Gln Val Ser Leu
            355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Met
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450
```

```
<210> SEQ ID NO 86
<211> LENGTH: 450
<212> TYPE: PRT
<213> ORGANISM: Artificial Sequence
<220> FEATURE:
<223> OTHER INFORMATION: Antibody PR003890 HC

<400> SEQUENCE: 86

Gln Val Gln Leu Val Glu Ser Gly Gly Gly Leu Val Gln Pro Gly Gly
1               5               10              15

Ser Leu Arg Leu Ser Cys Ala Thr Ser Gly Phe Thr Phe Ser Ser Tyr
            20              25              30

Ala Met Ser Trp Val Arg Gln Ala Pro Gly Lys Gly Leu Glu Trp Val
            35              40              45

Ser Leu Ile Ser Gly Ser Gly Gly Ser Pro Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Lys Gly Val Val Asn Trp Gly Ser Leu Phe Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
    130             135             140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 87
<211> LENGTH: 450
<212> TYPE: PRT
<213> ORGANISM: Artificial Sequence
<220> FEATURE:
<223> OTHER INFORMATION: Antibody PR003891 HC

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45
```

-continued

```
Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Gly Val Val Asn Trp Gly Ser Leu Phe Asp Tyr Trp Gly Gln
            100             105             110

Gly Thr Leu Val Thr Phe Ser Ser Ala Ser Thr Lys Gly Pro Ser Val
        115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
    210             215             220

Lys Thr His Thr Cys Pro Pro Cys Pro Ala Pro Glu Leu Leu Gly Gly
225             230             235             240

Pro Asp Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
    275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Glu Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
            355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450
```

```
<210> SEQ ID NO 88
<211> LENGTH: 455
<212> TYPE: PRT
<213> ORGANISM: Artificial Sequence
<220> FEATURE:
<223> OTHER INFORMATION: Antibody PR003894 HC

<400> SEQUENCE: 88

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Glu Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Tyr Tyr Gly Ser Gly Thr Tyr Tyr Tyr Val Met
            100                 105                 110

Asn Ala Trp Gly Gln Gly Ala Ser Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Asp Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
        290                 295                 300

Asn Ser Thr Phe Arg Val Val Ser Val Leu Thr Val Val His Gln Asp
305                 310                 315                 320

Trp Leu Asn Gly Lys Glu Tyr Lys Cys Lys Val Ser Asn Lys Ala Leu
                325                 330                 335

Pro Ala Pro Glu Glu Lys Thr Ile Ser Lys Thr Lys Gly Gln Pro Arg
            340                 345                 350

Glu Pro Gln Val Tyr Thr Leu Pro Pro Ser Arg Glu Glu Met Thr Lys
            355                 360                 365
```

-continued

```
Asn Gln Val Ser Leu Thr Cys Leu Val Lys Gly Phe Tyr Pro Ser Asp
    370             375                 380

Ile Ala Val Glu Trp Glu Ser Asn Gly Gln Pro Glu Asn Asn Tyr Lys
385             390                 395                 400

Thr Thr Pro Pro Met Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455
```

```
<210> SEQ ID NO 89
<211> LENGTH: 450
<212> TYPE: PRT
<213> ORGANISM: Artificial Sequence
<220> FEATURE:
<223> OTHER INFORMATION: Antibody PR003897 HC

<400> SEQUENCE: 89
```

```
Gln Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Leu Ile Ser Gly Ser Gly Gly Ser Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Val Val Asn Trp Gly Ser Leu Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270
```

-continued

Asp Pro Glu Val Gln Phe Asn Trp Tyr Val Asp Gly Val Glu Val His
　　　275　　　　　　　　　　280　　　　　　　285

Asn Ala Lys Thr Lys Pro Arg Glu Glu Gln Phe Asn Ser Thr Phe Arg
　　290　　　　　　　　295　　　　　　　　300

Val Val Ser Val Leu Thr Val Val His Gln Asp Trp Leu Asn Gly Lys
305　　　　　　　　310　　　　　　　315　　　　　　　320

Glu Tyr Lys Cys Lys Val Ser Asn Lys Ala Leu Pro Ala Pro Glu Glu
　　　　　　325　　　　　　　330　　　　　　　335

Lys Thr Ile Ser Lys Thr Lys Gly Gln Pro Arg Glu Pro Gln Val Tyr
　　　　340　　　　　　　345　　　　　　　350

Thr Leu Pro Pro Ser Arg Glu Glu Met Thr Lys Asn Gln Val Ser Leu
　　　355　　　　　　　360　　　　　　　365

Thr Cys Leu Val Lys Gly Phe Tyr Pro Ser Asp Ile Ala Val Glu Trp
　　370　　　　　　　375　　　　　　　380

Glu Ser Asn Gly Gln Pro Glu Asn Asn Tyr Lys Thr Thr Pro Pro Met
385　　　　　　　390　　　　　　　395　　　　　　　400

Leu Asp Ser Asp Gly Ser Phe Phe Leu Tyr Ser Lys Leu Thr Val Asp
　　　　　　405　　　　　　　410　　　　　　　415

Lys Ser Arg Trp Gln Gln Gly Asn Val Phe Ser Cys Ser Val Met His
　　　　420　　　　　　　425　　　　　　　430

Glu Ala Leu His Asn His Tyr Thr Gln Lys Ser Leu Ser Leu Ser Pro
　　　435　　　　　　　440　　　　　　　445

Gly Lys
　　450

<210> SEQ ID NO 90
<211> LENGTH: 450
<212> TYPE: PRT
<213> ORGANISM: Artificial Sequence
<220> FEATURE:
<223> OTHER INFORMATION: Antibody PR003898 HC

<400> SEQUENCE: 90

Glu Val Gln Leu Leu Glu Ser Gly Gly Gly Leu Val Gln Pro Gly Gly
1　　　　　　5　　　　　　　10　　　　　　　15

Ser Leu Arg Leu Ser Cys Ala Ala Ser Gly Phe Thr Phe Ser Ser Tyr
　　　20　　　　　　　25　　　　　　　30

Ala Met Ser Trp Val Arg Gln Ala Pro Gly Lys Gly Leu Glu Trp Val
　　　35　　　　　　　40　　　　　　　45

Ser Ala Ile Ser Gly Ser Gly Gly Ser Thr Tyr Tyr Ala Asp Ser Val
　　50　　　　　　　55　　　　　　　60

Lys Gly Arg Phe Thr Ile Ser Arg Asp Asn Ser Lys Asn Thr Leu Tyr
65　　　　　　　70　　　　　　　75　　　　　　　80

Leu Gln Met Asn Ser Leu Arg Ala Glu Asp Thr Ala Val Tyr Tyr Cys
　　　　　　85　　　　　　　90　　　　　　　95

Ala Lys Gly Val Val Asn Trp Gly Ser Leu Phe Asp Tyr Trp Gly Gln
　　　　　　100　　　　　　　105　　　　　　　110

Gly Thr Leu Val Thr Phe Ser Ser Ala Ser Thr Lys Gly Pro Ser Val
　　　115　　　　　　　120　　　　　　　125

Phe Pro Leu Ala Pro Ser Ser Lys Ser Thr Ser Gly Gly Thr Ala Ala
　　　130　　　　　　　135　　　　　　　140

Leu Gly Cys Leu Val Lys Asp Tyr Phe Pro Glu Pro Val Thr Val Ser
145　　　　　　　150　　　　　　　155　　　　　　　160

Trp Asn Ser Gly Ala Leu Thr Ser Gly Val His Thr Phe Pro Ala Val
　　　　　　165　　　　　　　170　　　　　　　175

-continued

```
Leu Gln Ser Ser Gly Leu Tyr Ser Leu Ser Ser Val Val Thr Val Pro
            180                     185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Ala Leu Pro Ala Pro Glu Glu
            325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

```
<210> SEQ ID NO 91
<211> LENGTH: 220
<212> TYPE: PRT
<213> ORGANISM: Artificial Sequence
<220> FEATURE:
<223> OTHER INFORMATION: Antibody PR000400 LC

<400> SEQUENCE: 91

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

```
Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 92
<211> LENGTH: 214
<212> TYPE: PRT
<213> ORGANISM: Artificial Sequence
<220> FEATURE:
<223> OTHER INFORMATION: Antibody PR002725 LC

<400> SEQUENCE: 92

Glu Met Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Phe Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 93
<211> LENGTH: 214
<212> TYPE: PRT
<213> ORGANISM: Artificial Sequence
<220> FEATURE:
<223> OTHER INFORMATION: Antibody PR002726 LC, Antibody PR003197 LC,
      Antibody PR003292 LC, Antibody PR003293 LC, Antibody PR003340 LC

<400> SEQUENCE: 93

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 94
<211> LENGTH: 214
<212> TYPE: PRT
<213> ORGANISM: Artificial Sequence
<220> FEATURE:
<223> OTHER INFORMATION: Antibody PR002727 LC, Antibody PR003240 LC,
      Antibody PR003894 LC

<400> SEQUENCE: 94

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

```
Glu Asp Phe Ala Val Tyr Tyr Cys Gln Gln Tyr Asn Tyr Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 95
<211> LENGTH: 214
<212> TYPE: PRT
<213> ORGANISM: Artificial Sequence
<220> FEATURE:
<223> OTHER INFORMATION: Antibody PR003289 LC, Antibody PR003890 LC,
      Antibody PR003897 LC

<400> SEQUENCE: 95

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Asp Cys Gln Gln Tyr Asn Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 96
<211> LENGTH: 214
<212> TYPE: PRT
<213> ORGANISM: Artificial Sequence
<220> FEATURE:
<223> OTHER INFORMATION: Antibody PR003291 LC, Antibody PR003891 LC,
      Antibody PR003898 LC

<400> SEQUENCE: 96

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Asp Asp Phe Ala Val Tyr Tyr Cys Gln Gln Asn Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 97
<211> LENGTH: 330
<212> TYPE: PRT
<213> ORGANISM: Artificial Sequence
<220> FEATURE:
<223> OTHER INFORMATION: human IgG1 constant region

<400> SEQUENCE: 97

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 98
<211> LENGTH: 107
<212> TYPE: PRT
<213> ORGANISM: Artificial Sequence
<220> FEATURE:
<223> OTHER INFORMATION: human kappa constant region

<400> SEQUENCE: 98
```

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

CLDN18.2-TARGETING ANTIBODY, PREPARATION METHOD THEREFOR, AND USE THEREOF

REFERENCE TO SEQUENCE LISTING

The Sequence Listing is submitted concurrently with the specification as an ASCII formatted text file via EFS-Web. The Sequence Listing filed via EFS-Web is part of the specification and is incorporated in its entirety by reference herein.

The present application is a National Stage of International Application No. PCT/CN2020/118650, filed on Sep. 29, 2020, which claims priority of the Chinese Patent Application No. CN2019109413163, filed on Sep. 30, 2019, the contents of which are incorporated herein by reference in their entireties.

TECHNICAL FIELD

The present invention belongs to the field of biomedicine, and specially relates to an antibody targeting CLDN18.2 and a preparation method and application thereof.

BACKGROUND

Cancer is one of the most lethal diseases in human world today. In 2018 World Health Organization (WHO) report, there are about 18.07 million new cases of cancer each year. There are approximately 9.55 million deaths due to cancer each year. According to estimation of WHO, gastric cancer is the fifth most commonly diagnosed cancer in the world. Gastric cancer is the third (for men) and fourth (for women) leading cause of cancer-related deaths. Every year, there are 1 million new patients diagnosed with gastric cancer worldwide, and approximately 35% of first-time diagnoses in the U.S. are advanced gastric cancer. The 5-year survival rate for diagnosed advanced gastric cancer is 5%, and the median survival period is about 6 months. The first-line medication for the treatment of patients with metastatic/recurrent gastric cancer is divided into two categories: (1) patients positive in HER2-neu test are treated with Transtuzumab in combination with chemotherapeutic drugs, and (2) for patients negative in HER2-neu test, chemotherapy is the only treatment available, and the therapeutic effect is unsatisfactory (Front Pharmacol. 2018 Sep. 13; 9: 404).

The Genbank accession numbers of splice variant 1 (CLDN18A1, i.e. CLDN18.1) of CLDN18 (claudin18) are NP_057453 and NM016369, and that of splice variant 2 (CLD18A2, i.e. CLDN18.2) are NM_001002026 and NP_001002026, which are intrinsic transmembrane proteins with a molecular weight of approximately 27.9/27.72 kD. Claudins are intrinsic membrane proteins located in the tight junction between the epithelium and the endothelium. The other two major tight junction family proteins are occludin and junctional adhesion molecule (JAM). Claudins are essential components of tight junctions and play an important role in maintaining the polarity of epithelial cells, controlling paracellular diffusion and regulating cell growth and differentiation. It is hypothesized that claudins are nearly inaccessible to antibodies in structured epithelium, but would become exposed in tumor cells. The claudin molecules span the cell membrane four times with both N-terminus and C-terminus locating in the cytoplasm. Among them, human CLDN18.2 (claudin 18.2) protein is a transmembrane protein with a full length of 261 amino acids, of which amino acids 1-23 are signal peptides; it has two extracellular regions, namely an extracellular loop 1 (ECL1) of approximately 55 amino acids post the signal peptide and an ECL2 of 23 amino acids, respectively. CLDN18.1 (claudin 18.1) and CLDN18.2 differ in the first 21 amino acids at the N-terminus, including the first TM and loop 1 (i.e. ECL1), while the primary protein sequence at the C-terminus is identical. The ECL1 regions of human CLDN18.2 and human CLDN18.1 are very similar, and the ECL2 regions of human CLDN18.2 and human CLDN18.1 are identical. Thus, the development of antibodies targeting the human CLDN18.2 protein requires the search for antibodies against the ECL1 region or spatial structure of the human CLDN18.2 protein, which makes this work even more difficult. CLDN18.1 is selectively expressed in the epithelium of normal lung and stomach (Mol Cell Biol. 2001 November; 21(21):7380-90). Expression of CLDN18.2 in normal tissues is highly restricted to differentiated cells of the gastric epithelium while no expression in gastric stem cell region. However, it is highly expressed in several cancer types, including gastric cancer, esophageal cancer, pancreatic cancer, lung cancer and human cancer cell lines. The molecular weight of the protein differs in some cancers and in adjacent normal tissues. The higher molecular weight protein observed in healthy tissues can be converted to the same molecular weight as observed in cancer by treating the tissue lysis with the deglycosylated compound PNGaseF. This suggests that claudins are less N-glycosylated in cancer compared to their counterparts in normal tissue. This structural difference is likely to result in altered epitopes. The classical N-glycosylation motif is at amino acid position 116 of the D3 domain of the molecule ring (CN103509110B).

Currently, among the studies on antibody against human CLDN18.2, only Claudiximab (IMAB362) (see WO2014/146672) is in clinical trial phase. IMAB362 mediates antibody-dependent cell-mediated cytotoxicity (ADCC) and complement dependent cytotoxicity (CDC) effects as well as mediates tumor killing effect. IMAB362 has shown encouraging efficacy in Phase I and Phase II clinical trials for the treatment of advanced gastric and esophageal cancers (Eur J Cancer. 2018 September; 100:17-26). However, since IMAB362 is a human-mouse chimeric antibody, there is a risk of immunogenicity, and the affinity is not very high. Cytological experiments have proved that IMAB362 has only weak endocytosis activity, which makes it unsuitable for ADC development, and its therapeutic effect is extremely limited. Due to the unmet medical need for a large number of malignancies, there is a need for other CLDN18.2 antibodies with more desirable pharmaceutical characteristics. Therefore, there is a lack of effective antibodies targeting human CLDN18.2 protein in the art, especially of fully human antibodies, and antibodies with better cell-binding activity, ADCC activity, CDC activity, growth inhibitory effect, endocytic activity, etc.

Content of the Present Invention

The technical problem to be solved by the present invention is to overcome the defect of lacking antibodies targeting CLDN18.2 in the art, and an antibody targeting CLDN18.2 (human claudin 18.2) and a preparation method and application thereof are provided.

In order to solve the technical problems described above, the first aspect of the present invention provides: an antibody targeting CLDN18.2 or an antigen-binding fragment thereof, comprising a light chain variable region (VL) and/or a heavy chain variable region (VH), the heavy chain variable region comprises HCDR1, HCDR2 and HCDR3, the light chain variable region comprises LCDR1, LCDR2 and LCDR3; wherein the HCDR1 has an amino acid sequence of SEQ ID NO: 8 or variant 1 thereof, the HCDR2 has an amino acid sequence selected from the group consisting of SEQ ID NO: 16 and variant 2 thereof, and SEQ ID NO: 18 and variant 3 thereof, the HCDR3 has an amino acid sequence of any one of SEQ ID NO: 26-29, the LCDR1 has an amino acid sequence of SEQ ID NO: 42 or variant 4 thereof, the LCDR2 has an amino acid sequence of SEQ ID NO: 47 or variant 5 thereof, the LCDR3 has an amino acid sequence of SEQ ID NO: 55 or variant 6 thereof, the variant has substitution, deletion or addition of 1, 2 or 3 amino acids to the original amino acid sequence, and antibody or antigen-binding fragment comprising the variant retains binding ability to CLDN18.2.

In the sentence similar to "with 3, 2 or 1 amino acid mutation", the "amino acid mutation" refers to the amino acid mutation in the sequence of the variant comparing to the original amino acid sequence, including addition, deletion or substitution of amino acids based on the original amino acid sequence. An exemplary explanation is that the mutation of CDR may comprise 3, 2 or 1 amino acid mutations, the same or a different number of amino acid residues can optionally be selected for mutation between these CDRs, for example, it can be one amino acid mutation for CDR1, but no amino acid mutation for CDR2 and CDR3.

In the present invention, the mutations may comprise mutations as currently known to those skilled in the art, such as some mutations that may be made to the antibody during production or application thereof, such as mutations at sites that may exist, in particular the sites of potential post-translational modifications (PTMs) of the CDR region, including mutations at sites related to those like aggregation sites of antibodies, deamidation sensitive sites (NG, NS, NH, etc.), aspartate isomerization (DG, DP) sensitive sites, N-glycosylation (N-{P}S/T) sensitive sites, oxidation sensitive sites.

With regard to the "variant" described above, wherein:
the variant 1 has a mutation preferably occurring at least at position 6 and/or position 7 of the amino acid sequence of SEQ ID NO: 8.
The variant 2 has a mutation preferably occurring at least at position 5 of the amino acid sequence of SEQ ID NO: 16.
The variant 3 has a mutation preferably occurring at least at position 3 of the amino acid sequence of SEQ ID NO: 18.
The variant 4 has a mutation preferably occurring at least at position 8 and/or position 9 of the amino acid sequence of SEQ ID NO: 42.
The variant 5 has a mutation preferably occurring at least at position 1 and/or position 4 of the amino acid sequence of SEQ ID NO: 47.
The variant 6 has a mutation preferably occurring at least at one or more of positions 3-5 of the amino acid sequence of SEQ ID NO: 55.
Preferably, the variant 1 comprises mutation S6G and/or Y7F, the variant 2 comprises mutation G5R, the variant 3 comprises mutation D3E, the variant 4 comprises mutation S8R and/or N9Y, the variant 5 comprises mutation G1D and/or T4N, and the variant 6 comprises one or more mutations of Y3R/N, N4S and N5Y.
In a preferred embodiment of the present invention, amino acid sequence of the variant 1 is SEQ ID NO: 6 or 7;
in a preferred embodiment of the present invention, amino acid sequence of the variant 2 is SEQ ID NO: 17;
in a preferred embodiment of the present invention, amino acid sequence of the variant 3 is SEQ ID NO: 19;

in a preferred embodiment of the present invention, amino acid sequence of the variant 4 is SEQ ID NO: 40 or 41;
in a preferred embodiment of the present invention, amino acid sequence of the variant 5 is SEQ ID NO: 48;
in a preferred embodiment of the present invention, amino acid sequence of the variant 6 is any one of SEQ ID NO: 56-58.

In a preferred embodiment of the present invention, amino acid sequence of the HCDR1 is SEQ ID NO: 7, amino acid sequence of the HCDR2 is SEQ ID NO: 17, and amino acid sequence of the HCDR3 is SEQ ID NO: 27; amino acid sequence of the HCDR1 is SEQ ID NO: 8, amino acid sequence of the HCDR2 is SEQ ID NO: 18, and amino acid sequence of the HCDR3 is SEQ ID NO: 28; amino acid sequence of the HCDR1 is SEQ ID NO: 8, amino acid sequence of the HCDR2 is SEQ ID NO: 16, and amino acid sequence of the HCDR3 is SEQ ID NO: 29; or, amino acid sequence of the HCDR1 is SEQ ID NO: 8, amino acid sequence of the HCDR2 is SEQ ID NO: 19, and amino acid sequence of the HCDR3 is SEQ ID NO: 28;
and/or, amino acid sequence of the LCDR1 is SEQ ID NO: 41, amino acid sequence of the LCDR2 is SEQ ID NO: 48, and amino acid sequence of the LCDR3 is SEQ ID NO: 56; amino acid sequence of the LCDR1 is SEQ ID NO: 42, amino acid sequence of the LCDR2 is SEQ ID NO: 47, and amino acid sequence of the LCDR3 is SEQ ID NO: 57; amino acid sequence of the LCDR1 is SEQ ID NO: 42, amino acid sequence of the LCDR2 is SEQ ID NO: 47, and amino acid sequence of the LCDR3 is SEQ ID NO: 55; or, amino acid sequence of the LCDR1 is SEQ ID NO: 42, amino acid sequence of the LCDR2 is SEQ ID NO: 47, and amino acid sequence of the LCDR3 is SEQ ID NO: 58.
Preferably, the VH further comprises a framework region of the heavy chain variable region (VH FWR), and/or, the VL further comprises a framework region of the light chain variable region (VL FWR);
more preferably, the VH FWR is a framework region of the heavy chain variable region of a human antibody, the VL FWR is a framework region of the heavy chain variable region of a human antibody. Wherein:
gene encoding the framework region of the heavy chain variable region is preferably derived from germline V gene IGHV3-23; preferably, in the framework region of the heavy chain variable region, HFR1 comprises an amino acid sequence of any one of SEQ ID NO: 2-4 or a variant thereof, HFR2 comprises an amino acid sequence of any one of SEQ ID NO: 10-14 or a variant thereof, HFR3 comprises an amino acid sequence of any one of SEQ ID NO: 21-24 or a variant thereof, HFR4 comprises an amino acid sequence of any one of SEQ ID NO: 31-33 or a variant thereof.
Gene encoding the framework region of the light chain variable region is preferably derived from germline V gene IGKV3-11 or IGKV3-15;
preferably, in the framework region of the light chain variable region, LFR1 comprises an amino acid sequence of any one of SEQ ID NO: 35-38 or a variant thereof, LFR2 comprises an amino acid sequence of SEQ ID NO: 44 or 45 or a variant thereof, LFR3 comprises an amino acid sequence of any one of SEQ ID NO: 50-53 or a variant thereof, LFR4 comprises an amino acid sequence of SEQ ID NO: 60 or 61 or a variant thereof.
In a most preferred embodiment of the present invention, amino acid sequence of the HCDR1 is SEQ ID NO: 7, amino acid sequence of the HCDR2 is SEQ ID NO: 17, amino acid sequence of the HCDR3 is SEQ ID NO: 27, amino acid sequence of the LCDR1 is SEQ ID NO: 41, amino acid sequence of the LCDR2 is SEQ ID NO: 48, and amino acid sequence of the LCDR3 is SEQ ID NO: 56;

amino acid sequence of the HCDR1 is SEQ ID NO: 8, amino acid sequence of the HCDR2 is SEQ ID NO: 18, amino acid sequence of the HCDR3 is SEQ ID NO: 28, amino acid sequence of the LCDR1 is SEQ ID NO: 42, amino acid sequence of the LCDR2 is SEQ ID NO: 47, and amino acid sequence of the LCDR3 is SEQ ID NO: 57;

amino acid sequence of the HCDR1 is SEQ ID NO: 8, amino acid sequence of the HCDR2 is SEQ ID NO: 16, amino acid sequence of the HCDR3 is SEQ ID NO: 29, amino acid sequence of the LCDR1 is SEQ ID NO: 42, amino acid sequence of the LCDR2 is SEQ ID NO: 47, and amino acid sequence of the LCDR3 is SEQ ID NO: 55;

amino acid sequence of the HCDR1 is SEQ ID NO: 8, amino acid sequence of the HCDR2 is SEQ ID NO: 16, amino acid sequence of the HCDR3 is SEQ ID NO: 29, amino acid sequence of the LCDR1 is SEQ ID NO: 42, amino acid sequence of the LCDR2 is SEQ ID NO: 47, and amino acid sequence of the LCDR3 is SEQ ID NO: 58;

or, amino acid sequence of the HCDR1 is SEQ ID NO: 8, amino acid sequence of the HCDR2 is SEQ ID NO: 19, amino acid sequence of the HCDR3 is SEQ ID NO: 28, amino acid sequence of the LCDR1 is SEQ ID NO: 42, amino acid sequence of the LCDR2 is SEQ ID NO: 47, and amino acid sequence of the LCDR3 is SEQ ID NO: 57.

In a specific embodiment of the present invention, the heavy chain variable region comprises an amino acid sequence of SEQ ID NO: 64 or a variant thereof, and the light chain variable region comprises an amino acid sequence of SEQ ID NO: 71 or a variant thereof;

the heavy chain variable region comprises an amino acid sequence of SEQ ID NO: 67 or a variant thereof, and the light chain variable region comprises an amino acid sequence of SEQ ID NO: 73 or a variant thereof;

the heavy chain variable region comprises an amino acid sequence of SEQ ID NO: 65 or a variant thereof, and the light chain variable region comprises an amino acid sequence of SEQ ID NO: 72 or a variant thereof;

the heavy chain variable region comprises an amino acid sequence of SEQ ID NO: 68 or a variant thereof, and the light chain variable region comprises an amino acid sequence of SEQ ID NO: 74 or a variant thereof;

or, the heavy chain variable region comprises an amino acid sequence of SEQ ID NO: 66 or a variant thereof, and the light chain variable region comprises an amino acid sequence of SEQ ID NO: 72 or a variant thereof;

wherein, the variant retains at least function of pre-mutated sequence, and the variant has at least 85%, preferably at least 90%, more preferably at least 95%, further more preferably at least 99% identity to the pre-mutated sequence.

In the present application, the amino acid sequences of the CDRs listed above are defined according to Chothia definition (the sequences in the claims of the present invention are also defined according to Chothia definition). However, it is well known to those skilled in the art that the CDR of antibody can be defined in the art according to a variety of methods, such as Kabat definition based on sequence variability (see, Kabat et al., sequences of proteins of immunological interest, fifth edition, national institutes of health, Bethesda, Maryland (1991)), and Chothia definition based on the location of a structural loop region (see J Mol Biol 273:927-48, 1997). In the present application, amino acid residues in variable domain sequences may also be determined using a Combined definition that incorporates both Kabat definition and Chothia definition. The Combined definition refers to the combination of the ranges of Kabat definition and Chothia definition, based on which a larger scope is taken, see Table 1-1. It should be understood by those skilled in the art that unless otherwise specified, the terms "CDR" and "complementarity determining region" of a given antibody or region thereof (e.g., a variable region) should be understood to encompass the complementary determining region as defined according to any of the embodiments described above of the present invention. Although the scope of protection claimed in the claims of the present invention is based on the sequences defined according to Chothia definition, amino acid sequences defined according to other CDR definitions should also fall within the scope of protection of the present invention.

TABLE 1-1

| CDR definition methods for antibodies of this application (available at http://bioinf.org.uk/abs/) | | | |
|---|---|---|---|
| | Kabat | Chothia | Combined |
| VL CDR1 | L24-L34 | L24-L34 | L24-L34 |
| VL CDR2 | L50-L56 | L50-L56 | L50-L56 |
| VL CDR3 | L89-L97 | L89-L97 | L89-L97 |
| VH CDR1 | H31-H35 | H26-H32 | H26-H35 |
| VH CDR2 | H50-H65 | H52-H56 | H50-H65 |
| VH CDR3 | H95-H102 | H95-H102 | H95-H102 |

Wherein, Laa-Lbb may refer to amino acid sequence from position aa to position bb starting from N-terminus of the light chain of an antibody; Haa-Hbb may refer to amino acid sequence from position aa to position bb starting from N-terminus of the heavy chain of an antibody. For example, L24-L34 may refer to amino acid sequence from position 24 to position 34 starting from N-terminus of the light chain of an antibody according to Chothia definition; and H26-H32 may refer to amino acid sequence from position 26 to position 32 starting from N-terminus of the heavy chain of an antibody according to Chothia definition. It is known to those skilled in the art that when the CDR is defined by Chothia, there may be addition sites at some positions, amino acid sequence of the VH CDR2 shown in SEQ ID NO: 17 in the present invention, for example, which has a 52A addition after position 52, as shown in Table 1-2 below.

TABLE 1-2

| Number of amino acid position | 52 | 52A | 53 | 54 | 55 | 56 |
|---|---|---|---|---|---|---|
| VH CDR2 ( SEQ ID NO: 17) | S | G | S | G | R | S |

Preferably, the antibody targeting CLDN18.2 further comprises an antibody heavy chain constant region and an antibody light chain constant region.

More preferably, the heavy chain constant region is selected from hIgG1, hIgG2, hIgG3 or hIgG4 or variants thereof, and the light chain constant region is selected from κ chain or λ chain of a human antibody or variants thereof.

Further more preferably, the heavy chain constant region is hIgG1, and the light chain constant region is κ chain of a human antibody.

Preferably, the antibody targeting CLDN18.2 is a full-length antibody, a Fab, a Fab', a F(ab')$_2$, a Fv, a scFv (single chain antibody fragment), a bispecific antibody, a multispecific antibody, a heavy-chain antibody or a single-domain antibody, or a monoclonal antibody or a polyclonal antibody derived from the antibody as defined above. The monoclonal antibody can be developed by a variety of routes and techniques, including hybridoma technology, phage display technology, single lymphocyte gene cloning technology, etc., the main technical means is the preparation of monoclonal antibodies from wild-type or transgenic mice by hybridoma technology.

When the antibody targeting CLDN18.2 is a bispecific antibody, it may comprise a first protein functional region and a second protein functional region. The first protein functional region may be a protein described above that targets CLDN18.2; the second protein functional region is a protein that does not target CLDN18.2 or is an antibody that also targets CLDN18.2 but not the antibody targeting CLDN18.2 of the present invention. Wherein, the first protein functional region may be an immunoglobulin, the second protein functional region may be one or more scFv; or, the second protein functional region may be an immunoglobulin, the first protein functional region may be one or more scFv.

Preferably, the antibody targeting CLDN18.2 is a full-length antibody, the full-length antibody comprises a heavy chain and a light chain, the heavy chain comprises an amino acid sequence of any one of SEQ ID NO: 77-90, and the light chain comprises an amino acid sequence of any one of SEQ ID NO: 93-96.

In a more specific embodiment, the heavy chain comprises an amino acid sequence of SEQ ID NO: 77, and the light chain comprises an amino acid sequence of SEQ ID NO: 93; the heavy chain comprises an amino acid sequence of SEQ ID NO: 78, and the light chain comprises an amino acid sequence of SEQ ID NO: 94; the heavy chain comprises an amino acid sequence of SEQ ID NO: 79, and the light chain comprises an amino acid sequence of SEQ ID NO: 93; the heavy chain comprises an amino acid sequence of SEQ ID NO: 85, and the light chain comprises an amino acid sequence of SEQ ID NO: 93; the heavy chain comprises an amino acid sequence of SEQ ID NO: 83, and the light chain comprises an amino acid sequence of SEQ ID NO: 93; the heavy chain comprises an amino acid sequence of SEQ ID NO: 84, and the light chain comprises an amino acid sequence of SEQ ID NO: 93; the heavy chain comprises an amino acid sequence of SEQ ID NO: 81, and the light chain comprises an amino acid sequence of SEQ ID NO: 95; the heavy chain comprises an amino acid sequence of SEQ ID NO: 82, and the light chain comprises an amino acid sequence of SEQ ID NO: 96; the heavy chain comprises an amino acid sequence of SEQ ID NO: 80, and the light chain comprises an amino acid sequence of SEQ ID NO: 94; the heavy chain comprises an amino acid sequence of SEQ ID NO: 86, and the light chain comprises an amino acid sequence of SEQ ID NO: 95; the heavy chain comprises an amino acid sequence of SEQ ID NO: 87, and the light chain comprises an amino acid sequence of SEQ ID NO: 96; the heavy chain comprises an amino acid sequence of SEQ ID NO: 88, and the light chain comprises an amino acid sequence of SEQ ID NO: 94; the heavy chain comprises an amino acid sequence of SEQ ID NO: 89, and the light chain comprises an amino acid sequence of SEQ ID NO: 95; or, the heavy chain comprises an amino acid sequence of SEQ ID NO: 90, and the light chain comprises an amino acid sequence of SEQ ID NO: 96. The sequence numbers of the exemplary antibodies are summarized in Table 1-3 below.

TABLE 1-3

| Antibody name | Type of light or heavy chain | Chain | Fv | FR1 | CDR1 | FR2 | CDR2 | FR3 | CDR3 | FR4 |
|---|---|---|---|---|---|---|---|---|---|---|
| PR000400 | HC | 75 | 62 | 1 | 5 | 9 | 15 | 20 | 25 | 30 |
| PR000400 | LC | 91 | 69 | 34 | 39 | 43 | 46 | 49 | 54 | 59 |
| PR002725 | HC | 76 | 63 | 2 | 6 | 10 | 16 | 21 | 26 | 31 |
| PR002725 | LC | 92 | 70 | 35 | 40 | 44 | 47 | 50 | 55 | 60 |
| PR002726 | HC | 77 | 64 | 2 | 7 | 11 | 17 | 22 | 27 | 31 |
| PR002726 | LC | 93 | 71 | 36 | 41 | 45 | 48 | 51 | 56 | 60 |
| PR002727 | HC | 78 | 65 | 3 | 8 | 12 | 18 | 21 | 28 | 32 |
| PR002727 | LC | 94 | 72 | 37 | 42 | 45 | 47 | 50 | 57 | 60 |
| PR003197 | HC | 79 | 64 | 2 | 7 | 11 | 17 | 22 | 27 | 31 |
| PR003197 | LC | 93 | 71 | 36 | 41 | 45 | 48 | 51 | 56 | 60 |
| PR003340 | HC | 85 | 64 | 2 | 7 | 11 | 17 | 22 | 27 | 31 |
| PR003340 | LC | 93 | 71 | 36 | 41 | 45 | 48 | 51 | 56 | 60 |
| PR003292 | HC | 83 | 64 | 2 | 7 | 11 | 17 | 22 | 27 | 31 |
| PR003292 | LC | 93 | 71 | 36 | 41 | 45 | 48 | 51 | 56 | 60 |
| PR003293 | HC | 84 | 64 | 2 | 7 | 11 | 17 | 22 | 27 | 31 |
| PR003293 | LC | 93 | 71 | 36 | 41 | 45 | 48 | 51 | 56 | 60 |
| PR003289 | HC | 81 | 67 | 4 | 8 | 13 | 16 | 23 | 29 | 31 |
| PR003289 | LC | 95 | 73 | 38 | 42 | 45 | 47 | 52 | 55 | 61 |
| PR003291 | HC | 82 | 68 | 2 | 8 | 14 | 16 | 24 | 29 | 33 |
| PR003291 | LC | 96 | 74 | 38 | 42 | 45 | 47 | 53 | 58 | 60 |
| PR003240 | HC | 80 | 66 | 3 | 8 | 12 | 19 | 21 | 28 | 32 |
| PR003240 | LC | 94 | 72 | 37 | 42 | 45 | 47 | 50 | 57 | 60 |
| PR003890 | HC | 86 | 67 | 4 | 8 | 13 | 16 | 23 | 29 | 31 |
| PR003890 | LC | 95 | 73 | 38 | 42 | 45 | 47 | 52 | 55 | 61 |
| PR003891 | HC | 87 | 68 | 2 | 8 | 14 | 16 | 24 | 29 | 33 |
| PR003891 | LC | 96 | 74 | 38 | 42 | 45 | 47 | 53 | 58 | 60 |
| PR003894 | HC | 88 | 66 | 3 | 8 | 12 | 19 | 21 | 28 | 32 |

TABLE 1-3-continued

| Antibody name | Type of light or heavy chain | Chain | Fv | FR1 | CDR1 | FR2 | CDR2 | FR3 | CDR3 | FR4 |
|---|---|---|---|---|---|---|---|---|---|---|
| PR003894 | LC | 94 | 72 | 37 | 42 | 45 | 47 | 50 | 57 | 60 |
| PR003897 | HC | 89 | 67 | 4 | 8 | 13 | 16 | 23 | 29 | 31 |
| PR003897 | LC | 95 | 73 | 38 | 42 | 45 | 47 | 52 | 55 | 61 |
| PR003898 | HC | 90 | 68 | 2 | 8 | 14 | 16 | 24 | 29 | 33 |
| PR003898 | LC | 96 | 74 | 38 | 42 | 45 | 47 | 53 | 58 | 60 |

Note:
the numbers in the above table represent the SEQ ID NO: of each antibody or its functional fragment in the sequence listing, and the antibody names do not impose any limitation on the antibody structure.

The variant has deletion, substitution or addition of one or more amino acid residues in the amino acid sequence of the VL and/or VH, and the mutated amino acid sequence has at least 8500 sequence identity to the amino acid sequence of the VL and/or VH, and retains or improves binding of the antibody to CLDN18.2; the at least 85% sequence identity is preferably at least 900% sequence identity; more preferably, at least 9500 sequence identity; most preferably, at least 9900 sequence identity.

In the present invention, "Fab fragment" consists of CH1 and variable region of a light chain and a heavy chain. The heavy chain of a Fab molecule cannot form a disulfide bond with another heavy chain molecule. "Fc" region has two heavy chain fragments comprising CH1 and CH2 domains of antibody. The two heavy chain fragments are linked together by two or more disulfide bonds and by hydrophobic interaction between CH3 domains. "Fab' fragment" contains a light chain and a portion of a heavy chain comprising a VH domain, a CH1 domain and a region between CH1 and CH2 domain, whereby an interchain disulfide bond can be formed between two heavy chains of the two Fab' fragments to form a $F(ab')_2$ molecule. The "$F(ab')_2$ fragment" has two light chains and two heavy chains that contain a portion of the constant region between the CH1 and CH2 domains, thereby forming an interchain disulfide bond between the two heavy chains. Thus, the $F(ab')_2$ fragment consists of two Fab' fragments held together by a disulfide bond between the two heavy chains. The term "Fv" refers to an antibody fragment consisting of the VL and VH domains of a single arm of antibody, but lacking a constant region.

In the present invention, the scFv (single chain antibody fragment) can be a conventional single chain antibody fragment in the art, which comprises a heavy chain variable region, a light chain variable region, and a short peptide of 15 to 20 amino acids. Wherein, the VL and VH domains form a monovalent molecule through a linker which enables the VH and VL to be paired as a single polypeptide chain [see, e.g., Bird et al., Science 242:423-426 (1988) and Huston et al., Proc. Natl. Acad. Sci. USA 85:5879-5883 (1988)]. Such scFv molecules may have a general structure: NH2-VL-linker-VH-COOH or NH2-VH-linker-VL-COOH. Suitable linker in the prior art consists of a repetitive $G_4S$ amino acid sequence or a variant thereof. For example, a linker having an amino acid sequence of $(G_4S)_4$ or $(G_4S)_3$ may be used, but variants thereof may also be used.

The term "multi-specific antibody" is used in its broadest sense to encompass antibodies with multi-specificity for epitopes. These multi-specific antibodies include, but are not limited to: antibodies comprising heavy chain variable regions (VH) and light chain variable regions (VL), wherein VH-VL units have multi-specificity for epitopes; antibodies having two or more VL and VH regions, wherein each VH-VL unit binds to a different target or a different epitope of the same target; antibodies having two or more single variable regions, wherein each single variable region binds to a different target or a different epitope of the same target; full-length antibodies, antibody fragments, bispecific antibodies (diabodies), and triantibodies (triabodies), antibody fragments covalently or non-covalently linked together, etc.

Antibodies of the present invention comprise monoclonal antibodies. The monoclonal antibodies or mAb or Ab of the present invention refer to antibodies obtained from single clonal cell strain, which is not limited to eukaryotic, prokaryotic or phage clonal cell strains.

In the present invention, the term "heavy chain antibody" refers to an antibody comprising only one heavy chain variable region (VHH) and two conventional CH2 and CH3 regions, also known as HCAbs.

In the present invention, the term "single domain antibody", also known as "nanobody", refers to a VHH structure cloned from a heavy chain antibody, which is the smallest unit known that has binding ability to a target antigen.

In order to solve the technical problems described above, the second aspect of the present invention provides: an isolated nucleic acid encoding the antibody targeting CLDN18.2 as described in the first aspect of the present invention.

The preparation method of the nucleic acid is a conventional preparation method in the art, preferably comprising the following steps: obtaining a nucleic acid molecule encoding the antibody described above by gene cloning technique or obtaining a nucleic acid molecule encoding the antibody described above by artificial full sequence synthesis method.

It is known to those skilled in the art that the base sequence encoding the amino acid sequence of the antibody described above may suitably incorporate substitution, deletion, alteration, insertion or addition to provide a homologue of a polynucleotide. The homologue of the polynucleotide of the present invention can be obtained by substitution, deletion or addition of one or more bases of a gene encoding the antibody sequence within a range of maintaining antibody activity.

In order to solve the technical problems described above, the third aspect of the present invention provides: a recombinant expression vector comprising the isolated nucleic acid as described in the second aspect of the present invention.

The recombinant expression vector can be obtained by conventional methods in the art, namely, which is constructed by connecting the nucleic acid molecule described in the present invention to various expression vectors. The expression vectors are various vectors conventionally used in the art as long as they are capable of carrying the nucleic acid molecule described above.

Preferably, the recombinant expression vector is a plasmid, a cosmid, a phage or a viral vector, and the viral vector is preferably a retroviral vector, a lentiviral vector, an adenovirus vector or an adeno-associated virus vector.

In order to solve the technical problems described above, the fourth aspect of the present invention provides: a transformant, which is a host cell comprising the recombinant expression vector as described in the third aspect of the present invention.

The preparation method of recombinant expression transformant can be a conventional preparation method in the art, for example, by transforming the recombinant expression vector into a host cell. The host cells are various host cells conventionally used in the art as long as the recombinant expression vector stably replicates itself and the carried nucleic acid can be efficiently expressed. Preferably, the host cell is an *E. coli* TG1 or a BL21 cell (for expressing single-chain antibody or Fab antibody), or a CHO-K1 cell (for expressing full-length IgG antibody). A preferred recombinant expression transformant of the present invention is obtained by transforming the recombinant expression plasmid described above into a host cell. Wherein the transformation method is a conventional transformation method in the art, preferably, a method of chemical transformation, a heat shock method or an electronporation method.

In the present invention, the antibody targeting CLDN18.2 can be used to prepare a chimeric antigen receptor (CAR) and so on, which can be modified onto cells such as T cells or NK cells. The present invention thus provides an antibody targeting CLDN18.2 as described in the first aspect of the present invention or an antigen-binding fragment thereof. For example, it is a chimeric antigen receptor that utilizes the scFv of the antibody targeting CLDN18.2 described above as an extracellular antigen-binding domain. Thus, in order to solve the technical problems described above, the fifth aspect of the present invention provides: a genetically modified cell comprising the antibody targeting CLDN18.2 as described in the first aspect of the present invention.

Preferably, the genetically modified cell is a eukaryotic cell, preferably, an isolated human cell; more preferably, an immune cell such as a T cell (e.g. in the form of CAR-T), or a NK cell.

In order to solve the technical problems described above, the sixth aspect of the present invention provides: a method for preparing the antibody targeting CLDN18.2, which comprises: culturing the transformant as described in the fourth aspect of the present invention and obtaining the antibody targeting CLDN18.2 from culture.

In order to solve the technical problems described above, the seventh aspect of the present invention provides: an antibody-drug conjugate (ADC) comprising a cytotoxic agent, and the antibody targeting CLDN18.2 as described in the first aspect of the present invention.

The cytotoxic agent is preferably a cytotoxic agent, a chemotherapeutic agent, a radioisotope, a therapeutic nucleic acid, an immunomodulator, an anti-angiogenic agent, an anti-proliferative pro-apoptotic agent or a cytolytic enzyme; more preferably, the cytotoxic agent is a tubulin synthetase inhibitor—methylaurethatin F (MMAF), or methylaurethatin E (MMAE).

The method for preparing the antibody-drug conjugate can be conventional in the art, preferably using the preparation method described in *Doronina, 2006, Bioconjugate Chem.* 17, 114-124. Preferably, the antibody-drug conjugate yielded in the method has a minimum low coupling fraction (LCF) of less than 10%.

The antibody-drug conjugate can exist in any physical form known in the art, preferably, a clear solution.

In order to solve the technical problems described above, the eighth aspect of the present invention provides: a pharmaceutical composition comprising the antibody targeting CLDN18.2 as described in the first aspect of the present invention and/or the antibody-drug conjugate as described in the seventh aspect of the present invention, and a pharmaceutically acceptable carrier.

The pharmaceutical composition preferably further comprises other anti-tumor antibodies as an active ingredient, and/or comprises one or more in the group consisting of hormone agents, targeted small molecule agents, proteasome inhibitors, imaging agents, diagnostic agents, chemotherapeutic agents, oncolytic drugs, cytotoxic agents, cytokines, activators of co-stimulatory molecules, inhibitors of inhibitory molecules and vaccines.

The pharmaceutically acceptable carrier can be a conventional carrier in the art, and the carrier can be any suitable physiologically or pharmaceutically acceptable pharmaceutical excipient. The pharmaceutical excipients are conventional pharmaceutical excipients in the art, preferably comprising pharmaceutically acceptable vehicles, fillers, stabilizers or diluents, etc. More preferably, the pharmaceutical composition comprises 0.01-990.99% of the protein and/or the antibody-drug conjugate, and 0.01-99.99% of a pharmaceutical carrier, the percentage is mass percentage of the pharmaceutical composition.

Preferably, the pharmaceutical composition is an anti-tumor drug. More preferably, the pharmaceutical composition a medicament for treating gastric cancer, esophageal cancer, lung cancer, ovarian cancer, melanoma, renal cancer, breast cancer, colorectal cancer, liver cancer, pancreatic cancer, bladder cancer, head and neck cancer, bronchial cancer, glioma, and/or leukemia.

The route of administration of the pharmaceutical composition of the present invention is preferably parenteral administration, injection administration or oral administration. The injection administration preferably includes intravenous injection, intramuscular injection, intraperitoneal injection, intradermal injection or subcutaneous injection, etc. The pharmaceutical composition is in various conventional dosage forms in the art, preferably, in solid form, semi-solid form or liquid form, i.e., as aqueous solution, non-aqueous solution or suspension, more preferably in form of tablet, capsule, granule, injection or infusion, etc. More preferably, it is administered intravascularly, subcutaneously, intraperitoneally or intramuscularly. Preferably, the pharmaceutical composition can also be administered as aerosol or as coarse spray, i.e., nasally; or it can be administered intrathecally, intramedullary or intraventricularly. More preferably, the pharmaceutical composition can also be administered transdermally, percutaneously, topically, enterally, vaginally, sublingually or rectally.

The dose level for administration of the pharmaceutical composition of the present invention can be adjusted according to the amount of composition that can achieve the desired diagnostic or therapeutic effect. The administration regimen may also be a single injection or multiple injections, or adjusted. The dose level and regimen selected are reasonably adjusted depending on various factors including activity, stability (i.e., half life), formulation and route of administration of the described pharmaceutical composition, combinations with other drugs or treatments, disease or condition to be detected and/or treated, health status and prior medical history of the subject to be treated.

The therapeutically effective dose of the pharmaceutical composition of the present invention may initially be estimated in cell culture experiments or animal models such as rodent, rabbit, dog, pig and/or primate. Animal models can also be used to determine suitable concentration ranges and routes of administration. It can be used to determine the useful dose and route of administration in humans can be subsequently determined based on results of animal models. In general, the determination and adjustment of effective amount or dose to be administered and the evaluation of when and how such adjustment is to be made are known to those skilled in the art.

For combination therapy, the above-antibody targeting CLDN18.2 as described above, the antibody-drug conjugate as described above, and/or additional therapeutic or diagnostic agents may each be used as a single agent over any period suitable for performing the intended therapy or diagnosis. Accordingly, these single agents may be administered substantially simultaneously (i.e., either as a single agent or within minutes or hours) or sequentially in succession. For example, these single agents may be administered within one year, or within 10, 8, 6, 4 or 2 months, or within 4, 3, 2, or 1 week, or within 5, 4, 3, 2, or 1 day.

Additional guidance on formulation, dose, administration regimens, and measurable therapeutic effects is provided in Berkow et al. (2000) The Merck Manual of Medical Information and Merck & Co. Inc., White House Station, New Jersey; Ebadi (1998) CRC Desk Reference of Clinical Pharmacology, etc.

In order to solve the technical problems described above, the ninth aspect of the present invention provides: a use of the antibody targeting CLDN18.2 as described in the first aspect of the present invention, the antibody-drug conjugate as described in the seventh aspect of the present invention and/or the pharmaceutical composition as described in the eighth aspect of the present invention in the preparation of a medicament for diagnosis, prevention and/or treatment of a tumor.

Preferably, the tumor is a CLDN18.2 positive tumor; more preferably, the tumor is gastric cancer, esophageal cancer, lung cancer, melanoma, renal cancer, breast cancer, colorectal cancer, liver cancer, pancreatic cancer, bladder cancer, glioma, and/or leukemia.

In order to solve the technical problems described above, the present invention also provides a use of the antibody targeting CLDN18.2 as described in the first aspect of the present invention, the antibody-drug conjugate as described in the seventh aspect of the present invention and/or the pharmaceutical composition as described in the eighth aspect of the present invention in diagnosis, prevention and/or treatment of a tumor. Preferably, the tumor is as described in the ninth aspect of the present invention.

In order to solve the technical problems described above, the tenth aspect of the present invention provides: a kit comprising kit A and kit B, wherein, the kit A is the antibody targeting CLDN18.2 as described in the first aspect of the present invention, and/or the antibody-drug conjugate as described in the seventh aspect of the present invention, and/or the pharmaceutical composition as described in the eighth aspect of the present invention; the kit B contains other anti-tumor antibodies or pharmaceutical composition comprising the other anti-tumor antibodies, and the kit B can also contain chemotherapeutic agents, oncolytic drugs, cytotoxic agents, cytokines, activators of co-stimulatory molecules, inhibitors of inhibitory molecules, vaccines, imaging agents, diagnostic agents, hormone agents, targeted small molecule agents, proteasome inhibitors, and the like, or the kit B also contains other anti-tumor antibodies or pharmaceutical composition comprising the other anti-tumor antibodies, as well as hormone agents, targeted small molecule agents, proteasome inhibitors, imaging agents, diagnostic agents, chemotherapeutic agents, oncolytic drugs, cytotoxic agents, cytokines, activators of co-stimulatory molecules, inhibitors of inhibitory molecules, vaccines, and the like. The kit A and the kit B can be used at the same time, or the kit A can be used before the kit B, or the kit B can be used before the kit A, it can be determined according to actual requirements of specific applications.

In order to solve the technical problems described above, the antibody targeting CLDN18.2 or the antigen-binding fragment thereof as described in the first aspect of the present invention, the chimeric antigen receptor as described above of the present invention, the genetically modified cell as described in the fifth aspect of the present invention, the antibody-drug conjugate as described in the seventh aspect of the present invention and/or the pharmaceutical composition as described in the eighth aspect of the present invention may also be co-administered with other drugs, for example, may be co-administered with hormone agents, targeted small molecule agents, proteasome inhibitors, imaging agents, diagnostic agents, chemotherapeutic agents, oncolytic drugs, cytotoxic agents, cytokines, activators of co-stimulatory molecules, inhibitors of inhibitory molecules, vaccines, and/or other anti-tumor antibodies (or pharmaceutical compositions comprising the other anti-tumor antibodies). The "CLDN18.2 positive" cells described in the present invention are cells that overexpress CLDN18.2 protein, such as NUGC4_D8 cell strain; conversely, cells that do not overexpress CLDN18.2 are named "CLDN18.2 negative" cells.

The eleventh aspect of the present invention provides: a method for diagnosing, treating and/or preventing CLDN18.2-mediated disease or symptom, which comprises: administering a therapeutically effective amount of the antibody targeting CLDN18.2 or the antigen-binding fragment thereof as described in the first aspect, the antibody-drug conjugate as described in the seventh aspect, or the pharmaceutical composition as described in the eighth aspect, or using a kit as described in the tenth aspect to the patient in need thereof.

Wherein, the CLDN18.2-mediated disease or symptom can be a tumor, preferably a CLDN18.2 positive tumor, more preferably gastric cancer, esophageal cancer, lung cancer, ovarian cancer, melanoma, renal cancer, breast cancer, colorectal cancer, liver cancer, pancreatic cancer, bladder cancer, head and neck cancer, bronchial cancer, glioma, and/or leukemia.

The twelfth aspect of the present invention provides: a method for immunoassaying or measuring CLDN18.2, which comprises using the antibody targeting CLDN18.2 or the antigen-binding fragment thereof as described in the first aspect, the antibody-drug conjugate as described in the seventh aspect, or the pharmaceutical composition as described in the eighth aspect.

The thirteenth aspect of the present invention provides: a combination therapy, which comprises: administering the antibody targeting CLDN18.2 or the antigen-binding fragment thereof as described in the first aspect, the antibody-drug conjugate as described in the seventh aspect or the pharmaceutical composition as described in the eighth aspect, and a second therapeutic agent, respectively, to a patient in need; the second therapeutic agent preferably comprises other anti-tumor antibodies or a pharmaceutical composition comprising the other anti-tumor antibodies, and/or one or more in the group consisting of hormone agents, targeted small molecule agents, proteasome inhibitors, imaging agents, diagnostic agents, chemotherapeutic agents, oncolytic drugs, cytotoxic agents, cytokines, activators of co-stimulatory molecules, inhibitors of inhibitory molecules and vaccines.

In the present invention, scientific and technical terms used herein have the meanings commonly understood by those skilled in the art, unless otherwise specified. Furthermore, laboratory procedures of culture of cell, molecular genetics, nucleic acid chemistry and immunology used herein are conventional procedures that are widely used in the respective fields. Meanwhile, for better understanding of the present invention, definitions and explanations of the related terms are provided below.

In the present invention, the term "variable" generally refers to the fact that certain portions of the sequence of the variable domain of antibody varies enormously, which determine binding activity and specificity of various specific antibodies to their specific antigens. However, variability does not uniformly locate throughout variable region of antibody. It is mainly located in three segments in variable regions of light and heavy chains, which are known as complementarity determining regions (CDR) or hypervariable regions (HVR). The relatively more conservative portions of the variable domain are known as framework regions (FWR). Each variable region of natural heavy and light chains comprises four FWRs, most of which adopt a β-folded configuration and are connected by three CDRs that form a loop linkage and in some cases form part of the β-folded structure. The CDRs in each chain are in close proximity to each other through the FWR region and together with the CDRs from the other chain form antigen binding site of an antibody, the constant regions are not directly involved in binding of antibody to antigen, but they exhibit different effector functions, such as involved in antibody-dependent cytotoxicity of antibody.

Three-letter codes and single-letter codes of amino acid used in the present invention are as known to those skilled in the art, or as described in J. Biol. Chem, 243, p 3558 (1968).

As used herein, the terms "include" or "comprise" are intended to indicate that compositions and methods include the elements described but do not exclude other elements, so is the case of "consisting of" as understood by the context.

The term "CLDN18.2" includes isotypes, CLDN18.2 of mammals (e.g., humans), species homologues of human CLDN18.2, and analogues comprising at least one same epitope of CLDN18.2. The amino acid sequence of CLDN18.2 (e.g., human CLDN18.2) is known in the art, as shown in the NCBI database.

The term "CLDN18.1" includes isotypes, CLDN18.1 of mammals (e.g., humans), species homologues of human CLDN18.1, and analogues comprising at least one same epitope of CLDN18.1. The amino acid sequence of CLDN18.1 (e.g., human CLDN18.1) is known in the art, as shown in the NCBI database.

The term "epitope" refers to portion of an antigen (e.g., human CLDN18.2) that specifically interacts with an antibody molecule. The term "competes" in the present invention means that an antibody molecule interferes with the binding ability of an anti-CLDN18.2 antibody molecule to a target (e.g., human CLDN18.2). The interference with binding can be direct or indirect (e.g., by allosteric modulation of antibody molecules or targets). Competitive binding assays (e.g., FACS assays, ELISA, or BIACORE assays) can be used to determine the extent to which an antibody molecule is capable of interfering with the binding of another antibody molecule to its target.

The term "antibody" as used in the present invention includes immunoglobulin, which is a four-peptide chain structure formed by connecting two identical heavy chains and two identical light chains through inter-chain disulfide bonds. Since amino acids in heavy chain constant region of immunoglobulin are different in composition and order, their antigenicity is also different. Accordingly, immunoglobulins can be divided into five classes, or isotypes of immunoglobulins, i.e., IgM, IgD, IgG, IgA, and IgE, whose corresponding heavy chains are $\mu$ chain, $\delta$ chain, $\gamma$ chain, $\alpha$ chain and $\epsilon$ chain, respectively. The same class of Ig can be divided into different subclasses according to the differences in amino acid composition of its hinge region and the number and position of the disulfide bonds of the heavy chains, e.g. IgG can be divided into IgG1, IgG2, IgG3 and IgG4. The light chains are divided into $\kappa$ chain or $\lambda$ chain according to the difference in the constant region. Each of the five classes of Ig can have either $\kappa$ chain or $\lambda$ chain.

In the present invention, the antibody light chain variable region described in the present invention may further comprise a light chain constant region comprising human $\kappa$ chain, $\lambda$ chain or variants thereof. In the present invention, the antibody heavy chain variable region described in the present invention may further comprise a heavy chain constant region comprising human IgG1, 2, 3, 4 or variants thereof.

The sequence of about 110 amino acids at N terminus in heavy chain and light chain of antibody is highly variable and is known as variable region; the sequence of other amino acids at C terminus is relatively stable and is known as constant region (region C). The variable region consists of three highly variable regions (HVR) and four sequence-relatively conservative framework regions (FWR). The three hypervariable regions determine the specificity of antibody, also known as complementarity determining region (CDR). Each light-chain variable region (VL) and heavy-chain variable region (VH) consists of three CDRs and four FWRs, which are sequentially arranged from the amino terminus to the carboxyl terminus in the following order: FWR1, CDR1, FWR2, CDR2, FWR3, CDR3 and FWR4. The three CDRs of the light chain refer to LCDR1, LCDR2 and LCDR3; the three CDRs of the heavy chain refer to HCDR1, HCDR2 and HCDR3.

Within the light and heavy chains, the variable and constant regions are connected by a "J" region of about 12 or more amino acids, and the heavy chain further comprises a "D" region of about 3 or more amino acids. Each heavy chain consists of a heavy chain variable region (VH) and a heavy chain constant region (CH). The heavy chain constant region consists of three domains (CH1, CH2, and CH3). Each light chain consists of a light chain variable region (VL) and a light chain constant region (CL). The light chain constant region consists of a CL domain. A constant region of antibody can mediate binding of an immunoglobulin to a host tissue or factor, including various cells (e.g., effector cells) of immune system and a first component (C1q) of the classical complement system. The VH region and VL region can also be subdivided into regions with high variability [referred to as complementarity determining region (CDR)], regions with more conservative regions referred to as framework region (FWR) interspersed therebetween. Each VH and VL consists of 3 CDRs and 4 FWRs arranged from the amino terminus to the carboxy terminus in the following order: FWR1, CDR1, FWR2, CDR2, FWR3, CDR3, FWR4. The variable regions corresponding to each heavy chain/ light chain (VH and VL) form an antibody binding site, respectively. In particular, the heavy chain may also contain more than 3 CDRs, e.g. 6, 9 or 12 CDRs. For example, in the bispecific antibodies of the present invention, the heavy chain may be the N-terminus of the heavy chain of an IgG antibody connected to the ScFv of another antibody, in which case the heavy chain has 9 CDRs.

The term "humanized antibody" includes antibodies having variable region and constant region of human germline immunoglobulin sequences. Humanized antibodies of the present invention may include amino acid residues that are not encoded by human germline immunoglobulin sequences (e.g., mutations introduced by random or site-specific mutagenesis in vitro or by somatic mutations in vivo). However, the term "human antibody" does not include antibodies in which CDR sequences derived from a germline of another mammalian species (e.g., mouse) has been grafted into a human framework sequence (i.e., "humanized antibody").

As used in the present invention, the term "specific" with respect to an antibody means an antibody that recognizes a specific antigen but does not substantially recognize or bind to other molecules in the sample. For example, an antibody that specifically binds to an antigen from one species may also bind to the antigen from one or more species. However, this interspecies cross-reactivity itself does not change the classification of antibodies based on specificity. In another example, an antibody that specifically binds to an antigen may also bind to different allelic forms of the antigen. However, this cross-reactivity itself does not change the classification of antibodies based on specificity. In some cases, the term "specific" or "specific binding" may be used to refer to the interaction of antibody, protein, or peptide with a second chemical, meaning that the interaction depends on the presence of a particular structure (e.g., an antigenic determinant cluster or epitope) on the chemical; for example, antibody generally recognizes and binds to specific protein structure, rather than protein. If an antibody is specific for epitope "A", the presence of another molecule containing epitope A (or dissociate, unlabeled A) will reduce the amount of labeled A bound to the antibody in the reaction between labeled "A" and antibody.

As used herein, the term "chimeric antigen receptor" or "CAR" refers to a polypeptide comprising an extracellular domain (extracellular binding domain), a hinge domain, a transmembrane domain (transmembrane region), and peptide which enables the transmission of cytoplasmic signal to domain (i.e., intracellular signaling domains). The hinge domain may be considered as part of a system for providing flexibility to the extracellular antigen binding region. The intracellular signal domain refers to a protein that transmits information into the cell via a certain signal transduction pathway by generating a second messenger to regulate cell activity, or a protein that acts as an effector corresponding to such messenger to generate signals that can promote immune effector function of CAR cells (e.g., CART cells). The intracellular signal domain comprises a signal transduction domain and may also comprise a co-stimulated intracellular domain derived from a co-stimulatory molecule.

"Identity", "variant sequence", and "mutation" refer to sequence similarity between two polynucleotide sequences or between two polypeptides. When the position in two compared sequences is occupied by the same base or amino acid monomer subunit, for example, if each position of two DNA molecules is occupied by adenine, then the molecules are homologous at that position. The percentage of identity between two sequences is a function of the number of matching or homologous positions that are shared the two sequences divided by the number of positions comparedx 100. For example, in the best sequence alignment, if 6 of the 10 positions in the two sequences are matched or homologous, the two sequences are 60% homologous. In general, comparisons are made when the two sequences are compared and the maximum percentage identity is obtained. "Optimize" refers to a mutation that retains or improves the binding of the antibody to the antigen, and in the present invention, a mutation that retains, maintains or improves binding to CLDN18.2.

The terms "polypeptide", "peptide" and "protein" (if single-stranded) are used interchangeably in the present invention. The terms "nucleic acid", "nucleic acid sequence", "nucleotide sequence" or "polynucleotide sequence" and "polynucleotide" are used interchangeably.

The term "mutation" includes substitution, addition and/or deletion of amino acids or nucleotides, "amino acid substitution" and "conservative amino acid substitution" are defined as the substitution of an amino acid residue with another amino acid residue and the substitution of an amino acid residue with a similar side chain, respectively.

As used herein, "lentivirus" refers to the genus of Retroviridae family. Lentiviruses are unique among retroviruses in their ability to infect non-dividing cells; they can deliver significant amounts of genetic information into DNA of host cells and are therefore one of the most effective methods of gene delivery vector. HIV, SIV and FIV are examples of lentiviruses. Vectors from lentiviruses provide means to achieve significant levels of gene transfer in vivo.

The term "vector" as used herein is a composition comprising isolated nucleic acid and can be used to deliver the isolated nucleic acid to the interior of a cell. Many vectors are known in the art, including but not limited to linear polynucleotides, polynucleotides associated with ionic or amphiphilic compounds, plasmids and viruses. Thus, the term "vector" includes an autonomously replicating plasmid or virus. The term should also be interpreted to include non-plasmid and non-viral compounds that promote the transfer of nucleic acids into cells, such as polylysine compounds, liposomes, etc. Examples of viral vectors include, but are not limited to, adenovirus vectors, adeno-associated viral vectors, retroviral vectors, etc.

The expressions "cell" and "cell line" as used in the present invention are used interchangeably, and all such names include descendants. The term "host cell" refers to cells that can be used to introduce a vector, including but not limited to prokaryotic cells such as *E. coli*, fungal cells such as yeast cells, or animal cells such as fibroblasts, CHO cells, COS cells, NSO cells, HeLa cells, BHK cells, HEK 293 cells or human cells.

The term "transfection" refers to the introduction of exogenous nucleic acids into eukaryotic cells. Transfection can be achieved by a variety of means known in the art, including calcium phosphate-DNA co-precipitation, DEAE-dextran-mediated transfection, polybrene-mediated transfection, electroporation, microinjection, liposome fusion, lipid transfection, protoplast fusion, retroviral infection and biolistics.

The term "immune cells" refers to cells that can trigger immune response, and "immune cells" and other grammatical forms thereof can refer to immune cells of any origin. "Immune cells" include, for example, white blood cells (leukocytes), lymphocytes (T cells, B cells, natural killer (NK) cells), and cells of bone marrow origin (neutrophils, eosinophils, basophils, monocytes, macrophages, dendritic cells) derived from hematopoietic stem cells (HSC) produced in bone marrow. The term "immune cell" can also be human or non-human.

As used herein, the term "T cells" refers to a class of lymphocytes that matures in the thymus. T cells play an important role in cell-mediated immunity and differ from other lymphocytes (e.g., B cells) in the presence of T cell receptors on the cell surface. "T cells" include all types of immune cells that express CD3, including helper T cells (CD4+ cells), cytotoxic T cells (CD8+ cells), natural killer T cells, regulatory T cells (Treg) and γ-δ T cells. "Cytotoxic cells" include CD8+ T cells, natural killer (NK) cells and neutrophils, which are capable of mediating cytotoxic responses. As used herein, the term "NK cells" refers to a class of lymphocytes that originates from the bone marrow and plays an important role in the innate immune system. NK cells provide a rapid immune response against virally infected cells, tumor cells or other stressed cells, even in the absence of antibodies and major histocompatibility complexes on the cell surface.

For example, the immune cells can be derived from blood, such as autologous T cells, allogeneic T cells, autologous NK cells and allogeneic NK cells, or from cell lines, such as NK cell lines prepared using EBV virus infection, NK cells and NK92 cell lines induced and differentiated from embryonic stem cells and iPSC.

"Optional", "any one", "any" or "any item" means that the event or circumstance described subsequently may, but need not, occur. For example, "optionally comprising one antibody heavy chain variable region" means that a specific sequence of antibody heavy chain variable regions may, but need not, be present. As used herein, "a" and "an" are used to refer to one or more grammatical objects in the present invention. Unless clearly indicated otherwise in the content, the term "or" is used herein to mean the term "and/or" and is used interchangeably therewith. "about" and "approximately" should generally mean the degree of acceptable error of the measured amount in view of the property or accuracy of the measurement. Exemplary degrees of error are generally within 10% thereof and more generally within 5% thereof. The methods and compositions disclosed herein encompass polypeptides and nucleic acids having a specified sequence, a variant sequence, or a sequence substantially identical or similar thereto, e.g., a sequence that is at least 85%, 90%, 95%, 99% or more identical to the sequence specified. In the case of an amino acid sequence, the term "substantially identical" is used in the present invention to refer to a first amino acid sequence.

As used herein, the term $EC_{50}$ refers to the concentration for 50% of maximal effect, i.e., the concentration that causes 50% of maximal effect.

The pharmaceutical composition of the present invention can be made into various dosage forms as needed, and can be administered by a physician at a dose that is beneficial to the patient based on the type, age, body weight and general disease condition of the patient, the mode of administration, etc. The mode of administration may be, for example, by injection or other treatments.

As use herein, the terms "antibody-drug conjugate" or "ADC" are used interchangeably.

Auristatin is a fully synthetic drug and the chemical structure is relatively easy to modify in order to optimize its physical properties and drug-forming properties. The main auristatin derivatives used for antibody coupling include monomethyl auristatin E (MMAE) and monomethyl auristatin F (MMAF), the former is a synthetic pentapeptide derived from the natural microtubulin polymerase inhibitor dolastatin-10, which is synthesized by adding a 2-amino-1-phenylpropyl-1-alcohol to the C-terminus thereof. The inhibitory activity of MMAE is less than one nanomole against a variety of human tumor cell lines. In order to reduce the cytotoxic activity of MMAE itself, MMAF adds a phenylalanine to the C-terminus of dolastatin-10. Due to the introduction of a carboxyl group in the structure, the cell membrane permeability of MMAF is relatively poor and therefore its biological activity on cells is significantly reduced. However, its inhibitory activity on cells is significantly increased after conjugating with antibody (U.S. Pat. No. 7,750,116).

In some embodiments, the antibody cytotoxic drug conjugate or a pharmaceutically acceptable salt or solvent compound thereof comprises an antibody of the present invention conjugated to one or more maytansinoid molecules. Maytansinoids are mitotic inhibitors that inhibiting the defunctionalization of microtubule protein polymerization. Maytansine was originally isolated from the East African shrub *Maytenus serrata* (U.S. Pat. No. 3,896,111). Subsequently, it was discovered that certain microorganisms also produce maytansinoids, such as maytanol and C-3 maytanol vinegar (U.S. Pat. No. 4,151,042). Maytansinoids are attractive drug modules in antibody-drug conjugates because they are: (i) relatively easy to prepare by fermentation or chemical modification or derivatization of fermentation products; (ii) easily derivatized with functional groups suitable for conjugating to antibody via non-disulfide junctions; (iii) stable in plasma; (iv) effective against a variety of tumor cell lines. Maytansinoid compounds suitable for use as pharmaceutical modules of maytansinoids are well known in the art and can be isolated from natural sources according to known methods or produced using genetic engineering techniques (see Yu et al. (2002) PNAS 99: 7968-7973). Maytanol and maytanol analogues can also be prepared synthetically according to known methods. Exemplary embodiments of the maytansinoid drug module include DM1, DM3 and DM4, as disclosed herein.

The method, composition, and combination therapy as described in the present invention may be combined with other active agents or treatments. The method comprises administering the anti-CLDN18.2 antibody of the present invention to a subject, in an amount effective to treat or prevent disease (e.g., cancer), optionally, with immunotherapy with PD-1 antibody, PD-L1 antibody, PD-L2 antibody, LAG-3 antibody, CTLA-4 antibody and Tim-3 antibody, etc., or other oncotherapeutic antibodies like Her-2 antibody, EGFR antibody, VEGF antibody and VEGFR antibody, as well as combinations of one or more inhibitors of ADCs (e.g., T-DM1), bispecific antibodies, chemotherapeutic drugs, etc., further comprising administering anti-CLDN18.2 antibody molecule, additional active agent, or all, which may be administered in such an amount or a dose that is higher, lower, or equal to the amount or dose of each active agent used alone (e.g., as monotherapy). Anti-CLDN18.2 antibody, additional active agent, or all, is administered in an amount or dose lower (e.g., at least 20%, at least 30%, at least 40%, or at least 50%) than the amount or dose of each active agent used alone (e.g., as monotherapy).

Furthermore, as described in embodiments of the present invention, anti-CLDN18.2 antibody and antibody-drug conjugate of CLDN18.2 antibody can bind to CLDN18.2 to induce apoptosis of target cells (tumor cells), inhibit tumor cell growth and increase ADCC and CDC killing effect of effector cells on tumor cells in vivo to achieve the purpose of treating cancer patients. Thus, in certain embodiments, the anti-CLDN18.2 antibodies and the antibody-drug con-jugates of CLDN18.2 antibodies described in the present invention exhibit the anti-tumor effects of the antibodies of the present invention by these mechanisms, as well as methods of inhibiting tumor cell growth, comprising admin-istering to a subject a therapeutically effective amount of the anti-CLDN18.2 antibodies and the antibody-drug conju-gates of CLDN18.2 antibodies described in the present invention. The method is suitable for in vivo treatment of cancer. In order to obtain a target-specific therapeutic effect, the anti-CLDN18.2 antibody molecule can be administered together with other antibodies. In the administration of one or more active agents in combination with anti-CLDN18.2 antibodies and antibody-drug conjugates of CLDN18.2 anti-bodies, the combination can be administered in any order or simultaneously to types of cancers, particularly tumors with high expression of CLDN18.2. In certain aspect, treatment for (e.g., to reduce or alleviate) hyperproliferative conditions or disease (e.g., cancer) to a subject is provided. The treatment comprises administering to a subject, either alone or in combination with other active agents or treatments, one or more of the anti-CLDN18.2 antibodies and the antibody-drug conjugates of CLDN18.2 antibodies described in the present invention.

Anti-CLDN18.2 antibody molecules alone or in combi-nation with another immunomodulator (e.g., anti-LAG-3, anti-Tim-3, anti-PD-1 or anti-PD-L1, anti-CTLA-4 antibody molecules) are used to treat gastric cancer, pancreatic cancer, lung cancer, esophageal cancer, ovarian cancer, etc. Anti-CLDN18.2 antibody molecules can be administered in com-bination with one or more of the following: immune-based strategies, targeted agents (e.g., VEGF inhibitors such as monoclonal antibodies against VEGF); VEGF tyrosine kinase inhibitors such as sunitinib, sorafenib, apartinib; inhibitors of RNAi or inhibitors of downstream mediators of VEGF signaling, for example, inhibitors of rapamycin mam-malian target (mTOR).

As used in the present invention, the terms "cancer", "cancers" and "cancer patient" are intended to include all types of cancerous growths or tumorigenic processes, meta-static tissues or malignant transformed cells, tissues or organs, regardless of their histopathological type or aggres-sive phase. Examples include, but are not limited to, solid tumors, hematological cancers, soft tissue tumors, and meta-static lesions.

Non-limiting examples of cancers that can be suitably treated with the antibodies targeting CLDN18.2 disclosed in the present invention include gastric cancer, esophageal cancer, lung cancer, melanoma, renal cancer, breast cancer, colorectal cancer, liver cancer, pancreatic cancer, bladder cancer, glioma, and/or leukemia, etc., or metastatic lesions thereof.

It should be noted that when referring to "variant 1", "variant 2" and the like in the present invention, the arabic numerals "1" and "2" after the terms have no practical meaning, but only refer to the same terms.

On the basis of meeting the common knowledge in the art, each of the preferred conditions described above can be arbitrarily combined to obtain each preferred example of the present invention. Reagents and raw materials used in the present invention are commercially available.

The positive and progressive effects of the present inven-tion are:

Compared with antibodies in the prior art, the antibodies of the present invention have significant advantages in binding affinity, ADCC (antibody-dependent cell-mediated cytotoxicity), CDC (complement dependent cytotoxicity), growth inhibitory effect, and endocytosis activity, etc., thereby having great potential for treating tumors. In one preferred embodiment of the present invention, HBM1029, PR003197, PR003340, PR003292, PR003293, PR003240, PR003291, PR003289, PR003890, PR003891, PR003894, PR003897 and PR003898 antibodies present higher binding affinity to NUGC4_D8 cells that endogenously express CLDN18.2 than IMAB362 analogue; HBM1029, PR003197, PR003340, PR003240, and PR003894 antibod-ies of the present invention mediate better ADCC effect than IMAB362 analogue in a dose-dependent manner specifically in NUGC4_D8; HBM1029, PR003197, PR003340 antibod-ies mediate better CDC effect than IMAB362 analogue in a dose-dependent manner in HEK293 hCLDN18.2; HBM1029 antibody mediates stronger growth inhibitory effect than IMAB362 analogue in a dose-dependent manner in HEK293 hCLDN 18.2; HBM1029 antibody mediates better endocytosis activity than IMAB362 analogue in a dose-dependent manner in NUGC4_D8; when co-cultured with anti-human IgG antibody-conjugated with MMAF, HBM1029 antibody produces better cytotoxic effect than IMAB362 analogue in a dose-dependent manner in NUGC4_D8 cells and HEK293 hCLDN18.2 cells.

DETAILED DESCRIPTION OF THE PREFERRED EMBODIMENT

Figure 1:
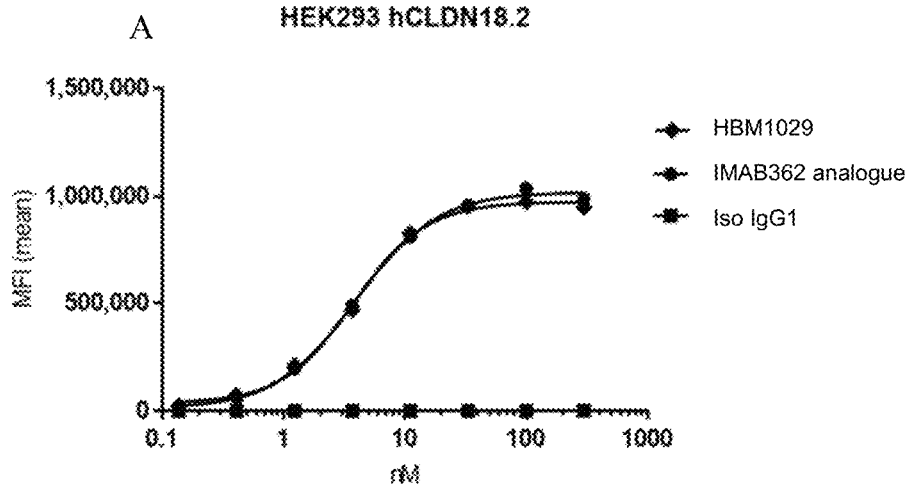
FIG. 1 shows the binding affinity of antibodies HBM1029 and PR002727 to HEK293 hCLDN18.2 cells (A), NUGC4_D8 cells (B), and HEK293 hCLDN18.1 cells (C), respectively.
Figure 1:
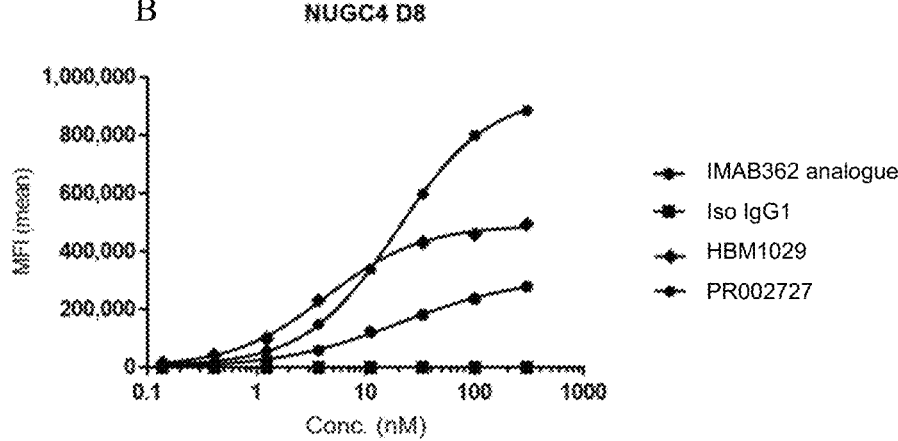
Figure 1:
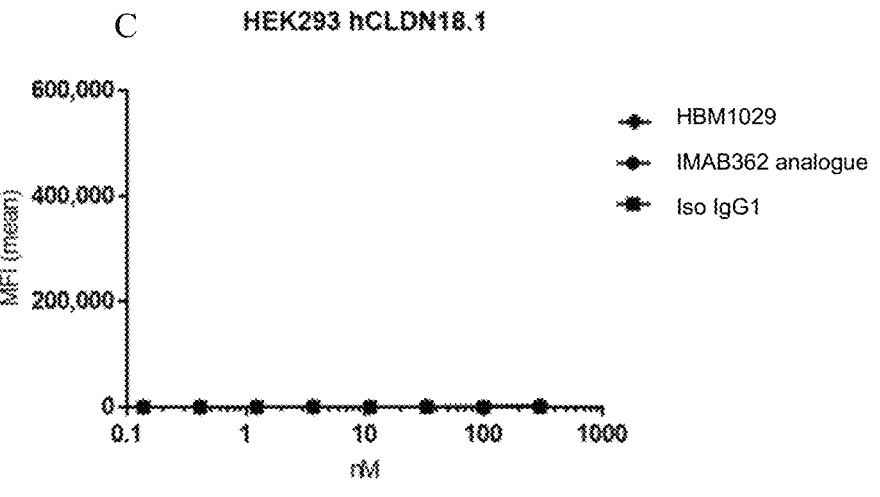

The present invention will be further illustrated by examples described below, which, however, are not intended to limit the scope of the present invention. The experimental methods for which specific conditions are not indicated in the following examples are selected according to conventional methods and conditions, or according to the commercial instruction.

Example 1: Antigen Preparation, Mouse Immunization and Hybridoma Preparation a. Preparation of an Expression Vector for Immunized Mice The preparation method of the human CLDN18.2 expression vector for immunizing the fully humanized transgenic mice is as follows: a cDNA sequence encoding human CLDN18.2 (Uniprot ID P56856-iso2) is synthesized, and the encoding sequence of the above gene is cloned into a pCAGGS plasmid (YOUBIO, VT1076) by enzymatic cleavage.

b. Preparation of Stably Transfected Cell Line

The construction of HEK293 (ATCC, Cat #: CRL-1573) cell line stably expressing human CLDN18.1 or CLDN18.2 is as follows: HEK293 cells were transfected with a plasmid encoding human CLDN18.1 (GenScript, OHu29174D) or CLDN18.2 (GenScript, OHu03374D) to generate stable cell line overexpressing human CLDN18.1 or CLDN18.2. The expression of CLDN18.1 and CLDN18.2 was detected by fluorescence-activated cell sorting (FACS). Specifically, 20,000 transfected cells were plated in each well of a 96-well plate and followed by addition of a commercially available rabbit anti-human CLDN18 antibody (LifeSpan Bio, Cat #: LS-C168812-400). After incubation for 1 h at 4° C., the plate was washed 2 times with PBS, and then AF-680-conjugated goat anti-rabbit IgG secondary antibody (Invitrogen, Cat #: A21091) was added. After incubation at 4° C. for 1 hour, the plate was washed 3 times with PBS, then the cell fluorescence was monitored using a FACS machine (IntelliCytiQue Plus BR).

Example 2: Production and Screening of CLDN18.2 Monoclonal Antibody

Fully humanized transgenic mice (HarbourH2L2 mice, commercially available mice, purchased from Harbour Biomed) were immunized with the human CLDN18.2 expression vector and the HEK293 cells (HEK293 hCLDN18.2 cells) expressing human CLDN18.2 prepared above. The human CLDN18.2 vector and gold powder were prepared into the bullets of a gene gun, and the mice were immunized with the gene gun at multiple points on the abdomen. Expression vector DNA was used to immunize with a dosage of 50 µg each time, with an interval of 2 weeks each time, after immunization for three times, HEK293 hCLDN18.2 cells were used to immunize, with $4\times10^6$ cells each time for each mouse, with an interval of 2 weeks each time, then blood samples were collected and titer was measured after cell immunization for 2 times. The binding affinity of mouse serum was detected by FACS using CHO K1 cells expressing human CLDN18.2 (CHOK1 hCLDN18.2, purchased from kyinno (KC-1180)) or CHO K1 cells expressing CLDN18.1 (CHO K1 hCLDN18.1, purchased from kyinno (KC-1181)). According to the results of serum titer test of immunized mice, mice were selected for hybridoma fusion; three days before fusion, HEK293 hCLDN18.2 cells was used for booster immunization at a dose of $4\times10^6$ cells for the mice. Spleen cells and lymph node cells of the mouse and mouse myeloma cells SP2/0 were mixed at a ratio of 2:1 (cell number ratio), and the mixed cells were fused with an electrofusion instrument (BTX ECM2001); the fused cells were placed on a 96-well cell culture plate, and incubated in a $CO_2$ incubator at 37° C. for 10 days before the primary screening of hybridomas. Primary screening was performed by Mirrorball using CHO K1 cells expressing human CLDN18.2, as follows: the cells were resuspended with a medium (F12K 10% FBS); the cell density was adjusted to $5\times10^4$ cells/ml, and 40 µl cell suspension was added into each well of a 384-well plate and incubated in a $CO_2$ incubator at 37° C. overnight. After staining the wells with the nuclear dye DRAQ5, the supernatant of the well plates was discarded, and 50 µl of the supernatant of the hybridoma culture plate was taken out and added into a 384-well microplate; after incubation at 4° C. for two hours, AF488-conjugated fluorescent secondary antibody (invitrogen, Cat #: A11066) was added and incubated at 4° C. overnight, then the 384-well microplate was detected by Mirrorball. Positive hybridomas were selected and transferred from the 96-well plate to a 24-well plate for expansion culture. 5 days later, supernatants from 24-well plates were rescreened. The rescreening was performed by FACS using CHOK1hCLDN18.1 cells and CHOK1hCLDN18.2 cells. Cells were centrifuged at 300 g for 5 minutes and then resuspended in FACS buffer (PBS containing 2% FBS). The density of cells was adjusted to $10^6$ cells/ml, and 50 µl of cell suspension was added into each well of a 96-well plate. After incubation at 4° C. for 2 hours, the plate was washed 2 times with FACS buffer. Subsequently, FACS buffer containing APC-conjugated goat anti-rat IgG secondary antibody (Biolegend, Cat #: 405407) was added. After incubation at 4° C. for 1 hour, the plate was washed 2 times with FACS buffer. Cells were resuspended with fixative for monitoring the fluorescence of the cells using a FACS machine (ACEA NovoCyte). The hybridomas with good specificity were subcloned by limiting dilution analysis, and primary screening of subclones was conducted after incubating the hybridomas in a $CO_2$ incubator at 37° C. for 7 days. The primary screening of subclones was detected by Mirrorball using CHO K1 cells expressing human CLDN18.2. According to the test results and observation under a microscope, clones that were both monoclonal and positively bound to CHOK1/CLDN18.2, were selected for expansion in a 24-well plate, and the supernatants in the wells were rescreened after incubation in a $CO_2$ incubator at 37° C. for 3 days. Rescreening was performed by FACS (the same rescreening procedure as described above) using CHOK1hCLDN18.1 and CHOK1hCLDN18.2 cell lines.

Monoclonal clones with specific binding were identified using subtype identification kit (invitrogen, Cat #: 88-50640-88). Cells with antibody subtype IgG2b were selected for sequencing (sequencing company: GENEWIZ Biotechnology Co., Ltd.).

It is well known to those skilled in the art that the CDR of an antibody can be defined in the art by a variety of methods, such as the Kabat definition rule based on sequence variability (see, Kabat et al., sequences of proteins of immunological interest, fifth edition, national institutes of health, Bethesda, Maryland (1991)) and Chothia definition rule based on the location of a structural loops region (see J Mol Biol 273:927-48, 1997). In the present application, amino acid residues in variable domain sequences may also be determined using a Combined definition rule that incorporates both Kabat definition and Chothia definition. The Combined definition rule refers to the combination of the ranges of Kabat definition and Chothia definition, based on which a larger range is taken, see Table 1-1 in the content of the present invention. The germline gene analysis and PTM site analysis obtained after sequencing in this embodiment are shown in Table 2 below. The design information of mutation sites of antigen-binding protein is shown in Table 3 below. The sequence number of antigen-binding protein is shown in Table 4 below.

TABLE 2 germline gene analysis and PTM site analysis of antibodies

| Clone number | VH germ- line V gene | VL germ- line V gene | VH PTM | VL PTM | Recom- binant anti- bodies | subtypes of recom- binant anti- bodies |
|---|---|---|---|---|---|---|
| 11C12- 13C2 | VH3-23 | VK3-15 | None | None | PR002725 | Human IgG1 |
| 13E6F4 | VH3-23 | VK3-11 | None | None | PR002726 | Human IgG1 |
| 31H3E2 | VH3-30 | VK3-15 | DG (HCDR2), DG (HCDR3) | None | PR002727 | Human IgG1 |
| 205A7F1D3 | VH3-23 | VK3-15 | None | None | PR003289 | Human IgG1 |
| 214C4G11 | VH3-23 | VK3-15 | None | None | PR003291 | Human IgG1 |

TABLE 3 design of antigen-binding protein mutation sites

| Primary antibodies | Variants | Variable region mutations | subtypes of recombinant antibodies | Fc mutations |
|---|---|---|---|---|
| PR002726 | PRO03197 | None | Human IgG1 | S239D, I332E |
| PR002726 | PR003292 | None | Human IgG1 | M252Y, S254T, T256E |
| PR002726 | PR003293 | None | Human IgG1 | S239D, I332E, M252Y, S254T, T256E |
| PR002726 | PR003340 | None | Human IgG1 | S239D, I332E, K274Q, Y300F, L309V, Y296F, A339T, V397M |
| PR003289 | PR003890 | None | Human IgG1 | S239D, I332E |
| PR003289 | PR003897 | None | Human IgG1 | S239D, I332E, K274Q, Y300F, L309V, Y296F, A339T, V397M |
| PR003291 | PR003891 | None | Human IgG1 | S239D, I332E |
| PR003291 | PR003898 | None | Human IgG1 | S239D, I332E, K274Q, Y300F, L309V, Y296F, A339T, V397M |
| PR002727 | PR003240 | VH:D54E | Human IgG1 | S239D, I332E |
| PR002727 | PRO03894 | VH:D54E | Human IgG1 | S239D, I332E, K274Q, Y300F, L309V, Y296F, A339T, V397M |

TABLE 4 antigen-binding protein sequence number table

| Antibody number | Light chain | Heavy chain | VL | VH | LCDR1 | LCDR2 | LCDR3 | HCDR1 | HCDR2 | HCDR3 |
|---|---|---|---|---|---|---|---|---|---|---|
| PR000400 | 91 | 75 | 69 | 62 | 39 | 46 | 54 | 5 | 15 | 25 |
| PR002725 | 92 | 76 | 70 | 63 | 40 | 47 | 55 | 6 | 16 | 26 |
| PR002726 | 93 | 77 | 71 | 64 | 41 | 48 | 56 | 7 | 17 | 27 |
| PR002727 | 94 | 78 | 72 | 65 | 42 | 47 | 57 | 8 | 18 | 28 |
| PR003197 | 93 | 79 | 71 | 64 | 41 | 48 | 56 | 7 | 17 | 27 |
| PR003340 | 93 | 85 | 71 | 64 | 41 | 48 | 56 | 7 | 17 | 27 |
| PR003292 | 93 | 83 | 71 | 64 | 41 | 48 | 56 | 7 | 17 | 27 |
| PR003293 | 93 | 84 | 71 | 64 | 41 | 48 | 56 | 7 | 17 | 27 |
| PR003289 | 95 | 81 | 73 | 67 | 42 | 47 | 55 | 8 | 16 | 29 |
| PR003291 | 96 | 82 | 74 | 68 | 42 | 47 | 58 | 8 | 16 | 29 |
| PR003240 | 94 | 80 | 72 | 66 | 42 | 47 | 57 | 8 | 19 | 28 |
| PR003890 | 95 | 86 | 73 | 67 | 42 | 47 | 55 | 8 | 16 | 29 |

TABLE 4-continued

antigen-binding protein sequence number table

| Antibody number | Light chain | Heavy chain | VL | VH | LCDR1 | LCDR2 | LCDR3 | HCDR1 | HCDR2 | HCDR3 |
|---|---|---|---|---|---|---|---|---|---|---|
| PR003891 | 96 | 87 | 74 | 68 | 42 | 47 | 58 | 8 | 16 | 29 |
| PR003894 | 94 | 88 | 72 | 66 | 42 | 47 | 57 | 8 | 19 | 28 |
| PR003897 | 95 | 89 | 73 | 67 | 42 | 47 | 55 | 8 | 16 | 29 |
| PR003898 | 96 | 90 | 74 | 68 | 42 | 47 | 58 | 8 | 16 | 29 |

Note:
PR002726C mentioned in the above table is HBM1029, and in the present invention, both numbers refer to one same antibody; PR000400 is an analogue of IMAB362, and both numbers refer to one same antibody in the present invention.

Example 3: Expression, Purification and Characterization of Full-Length CLDN18.2 Monoclonal Antibody After obtaining the nucleic acid encoding light and heavy chain variable domain sequences of the antibody molecules, the light and heavy chain variable domain sequences and corresponding human antibody light and heavy chain constant domain sequences can be fused and expressed by the conventional recombinant DNA technology to obtain the recombinant antibody molecules. In this example, the gene encoding antibody heavy chain variable domain sequence (VH) is synthesized and cloned into a mammalian cell expression plasmid vector encoding a human IgG1 antibody heavy chain constant domain sequence to encode a full-length heavy chain of an IgG1 antibody. The gene encoding antibody light chain variable domain sequence (VL) is synthesized and cloned into a mammalian cell expression plasmid vector encoding a human antibody Igκ light chain constant domain sequence to encode a full-length light chain of an antibody. In this example, since the sequence of the variable domain of the monoclonal antibody molecule obtained from immunized Harbour H2L2 mice is a human antibody sequence, this example yields a fully human anti-CLDN18.2 recombinant IgG1 antibody.

Plasmid (Genscript US) encoding heavy chain of antibody and plasmid (Genscript US) encoding light chain of antibody are simultaneously transfected into a mammalian host cell (e.g. human embryonic kidney cell HEK293), and purified recombinant antibody with correct paired assembly of heavy chain and light chain can be obtained by conventional recombinant protein expression and purification technology. Specifically, HEK293 cells were expanded and cultured in FreeStyle™ F17 Expression Medium (Thermo, Cat #: A1383504). Prior to start of transient transfection, cell concentration was adjusted to $6\text{-}8\times10^5$ cells/ml, and the cells were incubated in a shaker at 37° C. in 8% $CO_2$ for 24 hours, the cell concentration reached $1.2\times10^6$ cells/ml. 30 ml of cultured cells were prepared. The plasmid encoding the heavy chain of the antibody and the plasmid encoding the light chain of the antibody were mixed in a ratio of 2:3 (mass ratio), and a total of 30 μg of plasmid was dissolved in 1.5 ml Opti-MEM serum reduction medium (Thermo, Cat #: 31985088) and sterilized by filtration through a 0.22 μm filter membrane. Then 120 μl of 1 mg/ml PEI (Polysciences, Cat #: 23966-2) was dissolved in 1.5 ml Opti-MEM and allowed to stand for 5 minutes. The PEI was slowly added to the plasmid and incubated at room temperature for 10 minutes; the plasmid PEI mixture solution was slowly added dropwise into the flask while shaking, then the solution was incubated at 37° C. in 8% $CO_2$ for 5 days, followed by observing cell viability. The culture was collected and centrifuged at 3300 g for 10 minutes, and then supernatant was taken; the supernatant was then centrifuged at high speed to remove impurities. Gravity column (Bio-Rad, Cat #: 7311550) containing MabSelect™ (GE Healthcare Life Science, Cat #: 71-5020-91 AE) was equilibrated and rinsed with PBS (pH 7.4) of 2-5 times of the column volume. The column was loaded with the supernatant sample, followed by washing with PBS of 5-10 times of the column volume. Then the target protein was eluted with 0.1 M glycine at pH 3.5, which was later adjusted to neutral with Tris-HCl at pH 8.0, and finally concentrated and changed into PBS buffer using an ultrafiltration tube (Millipore, Cat #: UFC901024) to obtain a purified antibody solution. Finally, the concentration was measured by NanoDrop (Thermo Scientific™ NanoDrop™ One), separately packed and stored for later use.

Appropriate amounts of the above purified samples were separately loaded onto analytical SEC column TSKgel G3000SWxl (HPLC machine model: Agilent 1260 Infinity II) to detect the purity of the samples, ensuring that the purity of the homogeneous samples was more than 95%. The condition of the method was: mobile phase of 1×PBS, pH 7.4 (Biotech, Cat #: E607016), room temperature, flow rate of 1.0 ml/min, sample concentration of 1 mg/ml, injection volume of 20 μl and the detection wavelength of 280 nm. After collection, the chromatograms were integrated by ChemStation software and relevant data were calculated. Appropriate amounts of the above purified samples were separately loaded onto analytical HIC column TSKGE 1BUTTY1-NPR 4.6*35 (HPLC machine model: Agilent 1260 Infinity II) to detect the purity and hydrophobicity thereof. The method consists of a linear gradient over 16 minutes from 100% mobile phase A (20 mM PB, 1.8 M $(NH_4)_2SO_4$, pH 6.0) to 100% mobile phase B (20 mM PB, pH 6.0). The flow rate was set to 0.7 ml/min, the sample concentration was 1 mg/ml, the injection volume was 20 μl, and the detection wavelength was 280 nm. After collection, the chromatograms were integrated by ChemStation software and relevant data were calculated. Differential Scanning Fluorimetry (DSF) is a common high-throughput method to determine the thermal stability of proteins. It monitors the change in the fluorescence intensity of the dye bound to the unfolded protein molecule using a real-time fluorescent quantitative PCR machine to reflect the denaturation process of protein, thereby reflecting the thermal stability of the protein molecule. In this example, the DSF method was used to determine the thermal denaturation temperature (Tm) of protein molecules. 10 g of protein was added to a 96-well PCR plate (Thermo, Cat #: AB-0700/W), followed by 2 μl of 100× diluted dye SYPRO™ (Invitrogen, 2008138), and then buffer was added to make a final volume of 40 μl per well. The PCR plate was sealed and placed on a real-time fluorescent PCR machine (Bio-Rad CFX96 PCR System). The PCR plate was first incubated at 25° C. for 5 min, followed by a gradual increase in temperature from 25° C. to 95° C. with a gradient of 0.2° C./0.2 min and a decrease in temperature to 25° C. at the end of the test. FRET scanning mode and Bio-Rad CFX Maestro software were used to analyze the data and calculate the TM of the samples. The results are shown in table 5 below.

TABLE 5

| | SEC-HPLC purity (%) | HIC-HPLC purity (%) | HIC-HPLC retention time (min) | Tm1 (° C.) | Tm2 (° C.) |
|---|---|---|---|---|---|
| HBM1029 | 98 | 100 | 15.653 | 62.8 | 68.2 |

Example 4: Binding Affinity of CLDN18.2 Monoclonal Antibody

Figure 2:
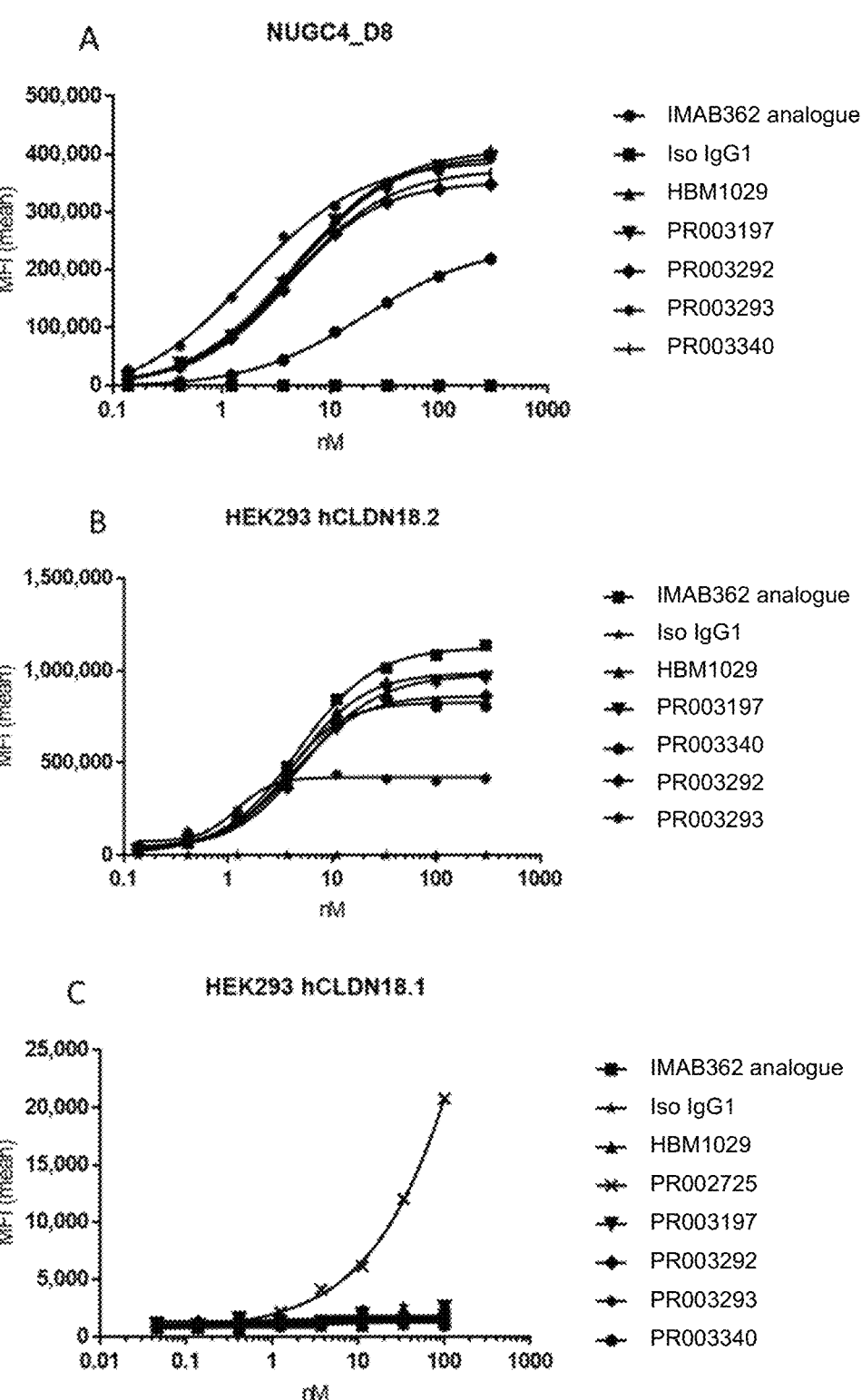
FIG. 2 shows the binding affinity of PR003197, PR003292, PR003293 and PR003340 antibodies to NUGC4_D8 cells (A) and HEK293 hCLDN18.2 cells (B); the binding affinity of PR003197, PR003292, PR003293, PR003340 and PR002725 antibodies to HEK293 hCLDN18.1 cells (C).
Figure 3:
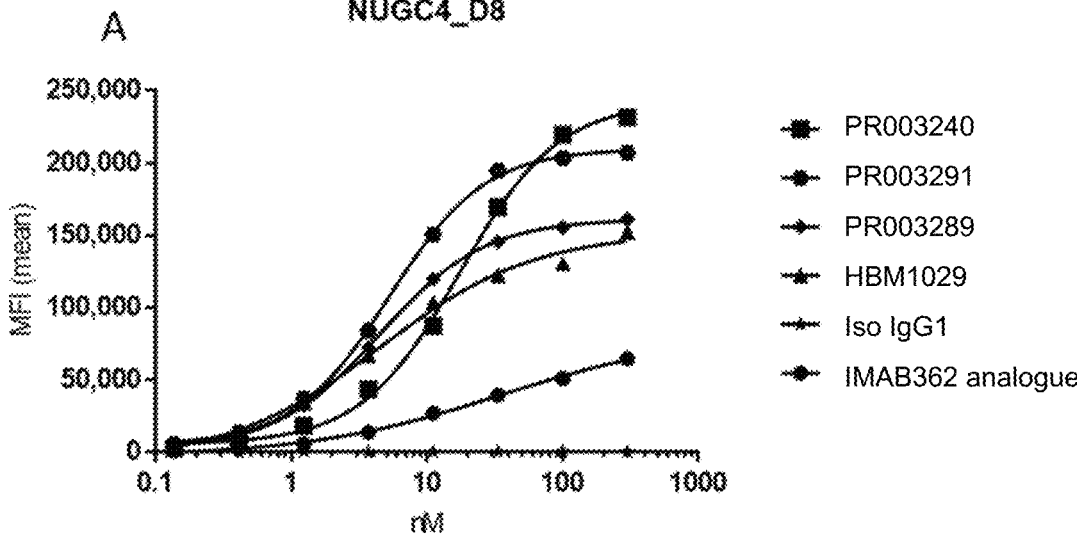
FIG. 3 shows the binding affinity of PR003240, PR003291, PR003289 and HBM1029 antibodies to NUGC4_D8 (A) and HEK293 hCLDN18.1 (B) cells, respectively.
Figure 3:
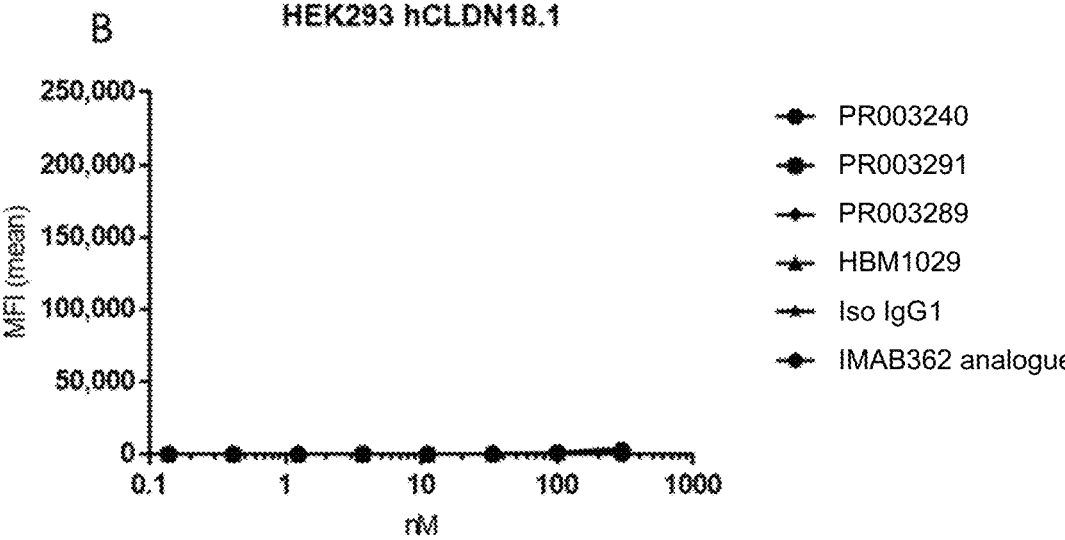
Figure 4:
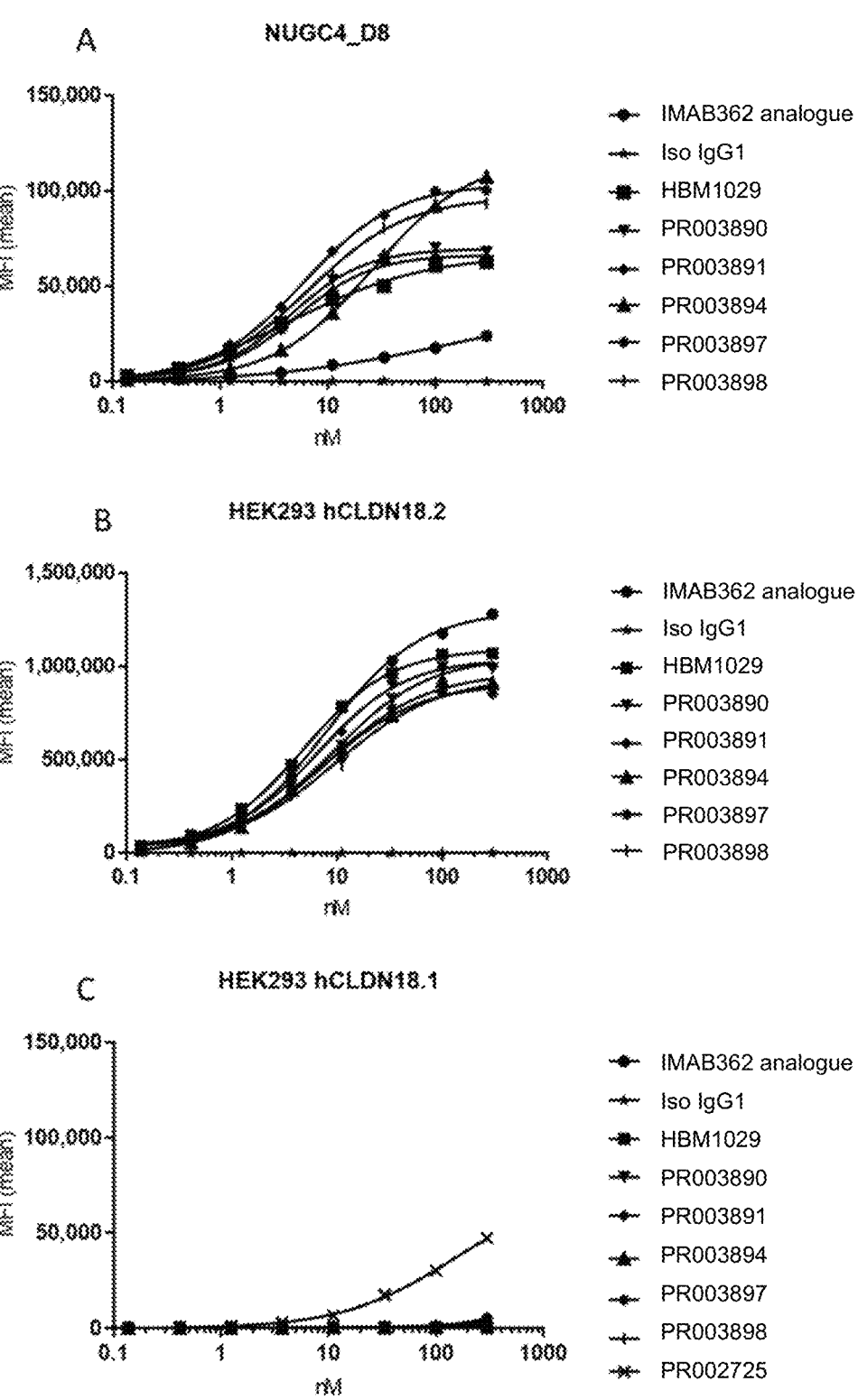
FIG. 4 shows the binding affinity of PR003890, PR003891, PR003894, PR003897 and PR003898 antibodies to NUGC4_D8 cells (A) and HEK293 hCLDN18.2 cells (B), respectively. The binding affinity of PR003890, PR003891, PR003894, PR003897, PR003898, PR002725 and HBM1029 antibodies to HEK293 hCLDN18.1 cells (C).

Antibody binding affinity was measured by FACS using HEK293 cells expressing human CLDN18.2 or CLDN18.1 and NUGC4_D8 cells endogenously expressing human CLDN18.2 (the NUGC cell line was purchased from JCRB, Cat #: JCRB0834), and selected by limiting dilution analysis to obtain NUGC4_D8 subclone cells), specifically: the cells were centrifuged at 300 g for 5 min and then resuspended in FACS buffer (PBS with 2% FBS). The cell density was adjusted to $10^6$ cells/ml, and 50 µl of cell suspension was added to each well of a 96-well plate. Antibodies were diluted to different concentrations with FACS buffer and 50 µl of antibody dilution was added to each well of the 96-well plate. After incubation at 4° C. for 2 hours, the plate was washed 2 times with FACS buffer. Subsequently, FACS buffer (final concentration of 1.5 µg/ml, Jackson, Cat #: 109-605-098) containing APC-conjugated goat anti-human IgG secondary antibody was added. After incubation at 4° C. for 1 hour, the plate was washed 2 times with FACS buffer. The cells were resuspended with fixative for monitoring the fluorescence of the cells using a FACS machine (ACEA NovoCyte). IMAB362 analogue (IMAB362 analogue was home-made, with amino acid sequence of heavy chain shown in SEQ ID NO: 75 and amino acid sequence of light chain shown in SEQ ID NO: 91 (synthesized by Genscript Biotechnology Co., Ltd.), which is identical to the variable region of IMAB362, with only individual amino acids different in the constant region, and both have similar activity) was used as positive control, and antibody of human Iso IgG1 (CrownBio, Cat #: C00001-4) was used as negative control. FIG. 1 shows the binding affinity of HBM1029 antibody to NUGC4_D8 cells endogenously expressing CLDN18.2, and HEK293 cells overexpressing human CLDN18.2 (HEK293 hCLDN 18.2) or HEK293 cells overexpressing human CLDN18.1 (HEK293 hCLDN18.1). PR002727 antibody was able to bind to NUGC4_D8 cells in a dose-dependent manner. HBM1029 antibody was able to bind to HEK293 hCLDN18.2 and NUGC4_D8 cells in a dose-dependent manner. The binding affinity of HBM1029 antibody to HEK293 hCLDN18.2 cells was comparable to that of the IMAB362 analogue; HBM1029 antibody showed higher binding affinity to NUGC4_D8 cells endogenously expressing CLDN18.2 compared to the IMAB362 analogue. The $EC_{50}$ values of HBM1029 are shown in Table 7, and HBM1029 showed lower $EC_{50}$ values for binding affinity to NUGC4_D8 cells endogenously expressing CLDN18.2 compared to the IMAB362 analogue. HBM1029 had a low binding affinity to HEK293 hCLDN18.1 cells. At the same time, it can be inferred that HBM1029 binds to ECL1 (Extracellular loop 1) of human CLDN18.2 protein instead of ECL2. FIG. 2, FIG. 3 and FIG. 4 show the binding affinity of CLDN18.2 antibody to NUGC4_D8 cells endogenously expressing CLDN18.2, HEK293 cells overexpressing human CLDN18.2 (HEK293 hCLDN 18.2) and HEK293 cells overexpressing human CLDN18.1 (HEK293 hCLDN18.1). Results show that: compared with the IMAB362 analogue, HBM1029, PR003197, PR003340, PR003292, PR003293, PR003240, PR003291, PR003289, PR003890, PR003891, PR003894, PR003897 and PR003898 antibodies presented higher binding affinity to NUGC4_D8 cells endogenously expressing CLDN18.2 and lower binding affinity to HEK293 hCLDN18.1 cells, while PR002725 showed high affinity to HEK293 hCLDN18.1.

TABLE 6

| amino acid sequences of IMAB362 analogue (synthesized by Genscript Biotechnoloy Co., Ltd.) | |
|---|---|
| amino acid sequence of heavy chain | SEQ ID NO: 75 |
| amino acid sequence of light chain | SEQ ID NO: 91 |

TABLE 7

| $EC_{50}$ values for binding affinity of HBM1029 antibody | | | |
|---|---|---|---|
| Cells | | HBM1029 | IMAB362 analogue |
| HEK293 hCLDN18.2 | Max Binding (MFI) | 976,754 | 1,022,190 |
| | $EC_{50}$ (nM) | 3.8 | 4.0 |
| NUGC4_D8 | Max Binding (MFI) | 490,220 | 313,021 |
| | $EC_{50}$ (nM) | 4.4 | 20.7 |

Example 5: ADCC Activity of CLDN18.2 Antibody

Figure 5:
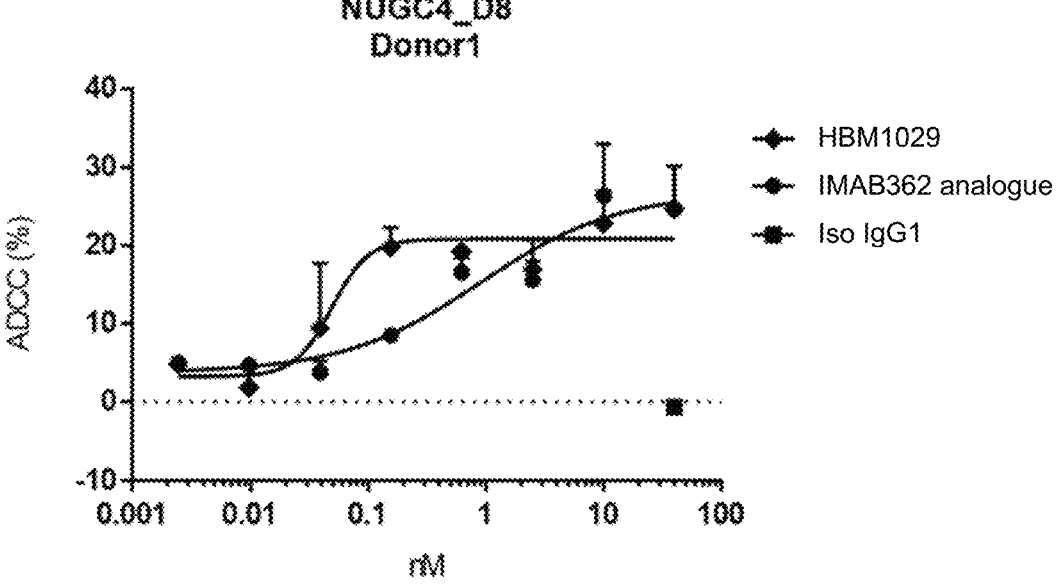
FIG. 5 shows that HBM1029 antibody exhibited ADCC activity to NUGC4_D8 cells, HEK293 hCLDN 18.1 cells by human PBMC.
Figure 5:
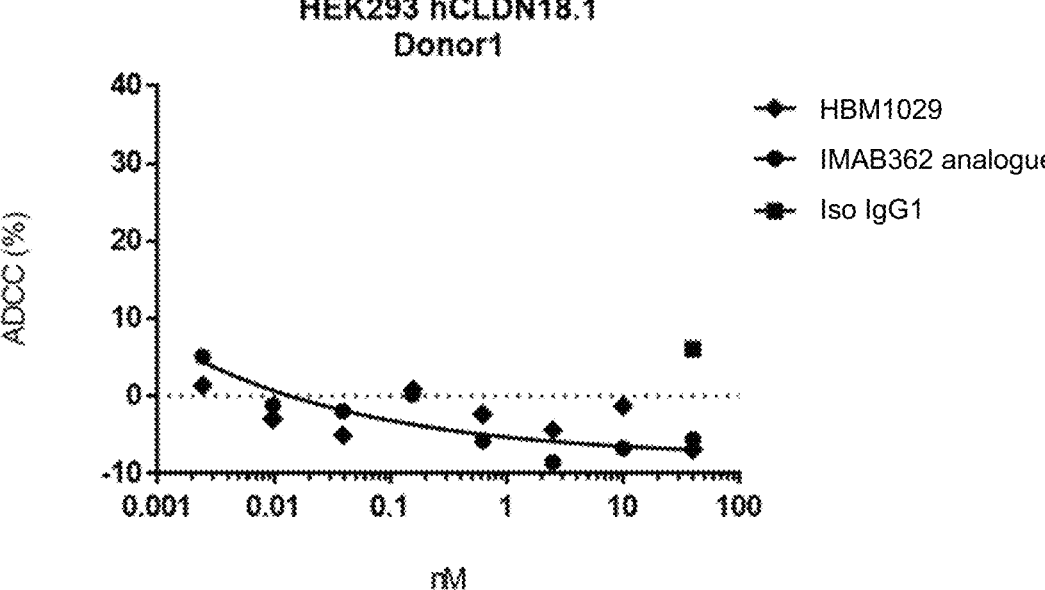

The activity of CLDN18.2 antibody mediating ADCC effect against NUGC4_D8 cells endogenously expressing human CLDN18.2 and HEK293 hCLDN 18.1 was assayed using CytoTox 96® Non-Radioactive Cytotoxicity Assay Kit (Promega, Cat #: G1780). Human PBMC (Miaotong) were centrifuged at 300 g for 5 minutes and incubated overnight in medium (RPMI1640+10% FBS). Target cells and human PBMC were centrifuged at 300 g for 5 minutes and then resuspended in medium (RPMI1640+2% FBS). The density of target cells was adjusted to $2\times10^5$ cells/ml, and the cell density of PBMC was adjusted to at least $6\times10^6$ cells/ml, then 50 µl of each type of cell was added into wells of a 96-well plate (the effective target ratio was at least 30:1). The antibodies to be tested were diluted with medium (RPMI1640+2% FBS) into different concentrations and added to each well. Samples were incubated at 37° C. for at least 4 hours, then 10 times Triton-X 100 lysate (RPMI1640+2% FBS+10% Triton-X 100) was added to the target cell maximum LDH release control wells and the volume correction control wells, mixed, and incubated at 37° C. for 0.5 hour. The 96-well plate was centrifuged at 300 g for 5 minutes, 50 µl of supernatant was removed, and then LDH chromogenic substrate was added at a concentration of 50 l/well. After the mixture was placed in the dark at room temperature for 20 minutes, the plate was read on MD StakMax ($OD_{490}$). IMAB362 analogue was used as positive control, and antibody of human Iso IgG1 (CrownBio, Cat #: C00001-4) was used as negative control. Results: firstly, the correction readings were calculated, the readings of experimental wells, target cell spontaneous LDH release control wells and effector cell spontaneous LDH release control wells were subtracted from the readings of medium background control wells, secondly, the readings of the target cell maximum LDH release control wells were subtracted from the readings of the volume corrected control wells. ADCC activity (%)=(experimental well corrected reading–effector cell spontaneous release LDH well corrected reading–target cell spontaneous LDH release well corrected reading)/(target cell maximum LDH release well corrected reading–target cell spontaneous release LDH well corrected reading)×100. FIG. 5 shows the ADCC activity of HBM1029 antibody against NUGC4_D8 cells endogenously expressing CLDN18.2 and HEK293 hCLDN18.1. HBM1029 antibody specifically mediated a stronger ADCC effect in a dose-dependent manner against NUGC4_D8 than IMAB362 analogue, while no cytotoxic effect was observed on HEK-293 cells overexpressing CLDN18.1. The $EC_{50}$ value of HBM1029 is shown in Table 8 and the $EC_{50}$ value of HBM1029-mediated ADCC against NUGC4_D8 was lower than the IMAB362 analogue.

TABLE 8

| | ADCC activity of HBM1029 | | |
| --- | --- | --- | --- |
| cell | | HBM1029 | IMAB362 analogue |
| NUGC4_D8 | Max Lysis (%) | 20.9 | 26.9 |
| | $EC_{50}$ (nM) | 0.05 | 0.91 |

Figure 6:
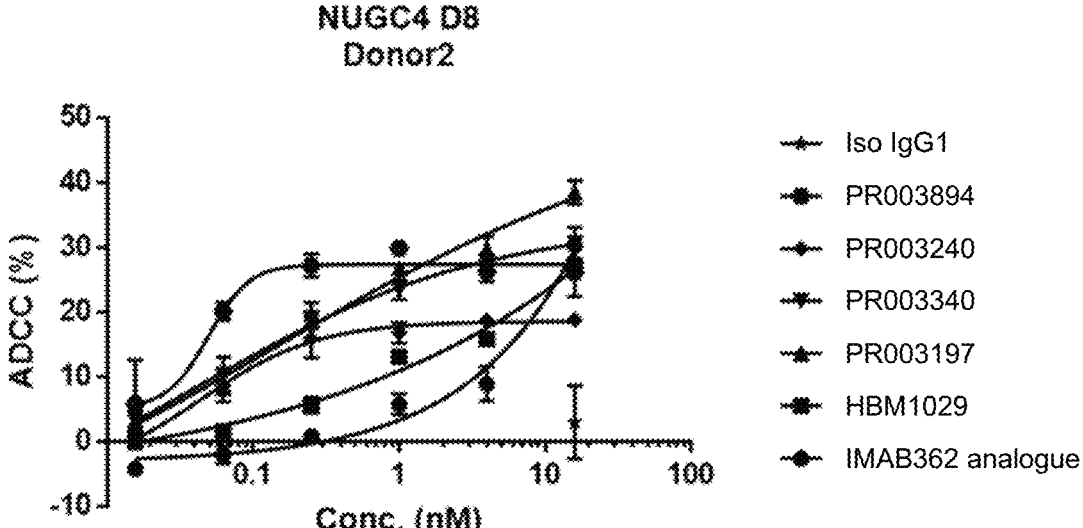
FIG. 6 shows that PR003894, PR003240, PR003340, PR003197 and HBM1029 exhibited ADCC activity to NUGC4_D8 cells by human PBMC.

FIG. 6 illustrates the ADCC activities of HBM1029, PR003197, PR003340, PR003240 and PR003894 against NUGC4_D8 cells endogenously expressing CLDN18.2; HBM1029, PR003197, PR003340, PR003240 and PR003894 were able to mediate stronger ADCC effect in a dose-dependent manner on NUGC4_D8 than IMAB362 analogue.

Figure 7:
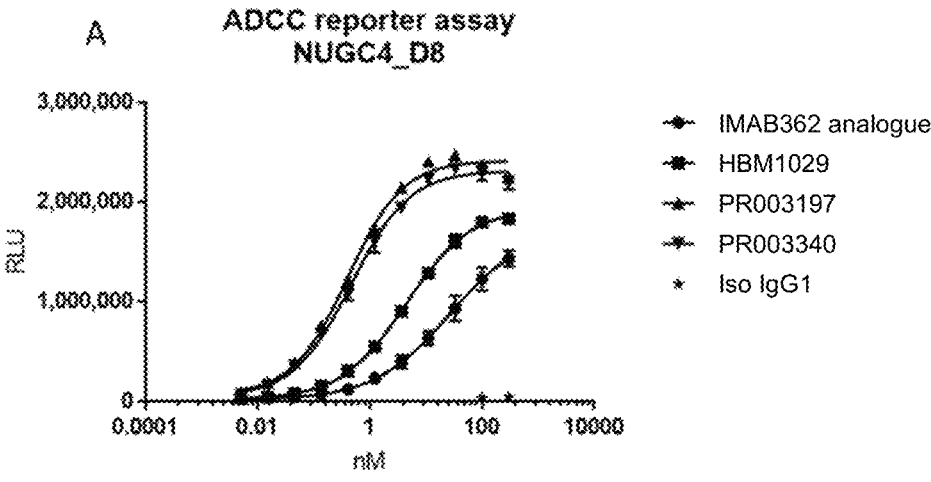
FIG. 7 shows that HBM1029, PR003894, PR003240, PR003340, PR003197, PR003891 and PR003898 exhibited ADCC activity to NUGC4_D8 cells by reporter cells.
Figure 7:
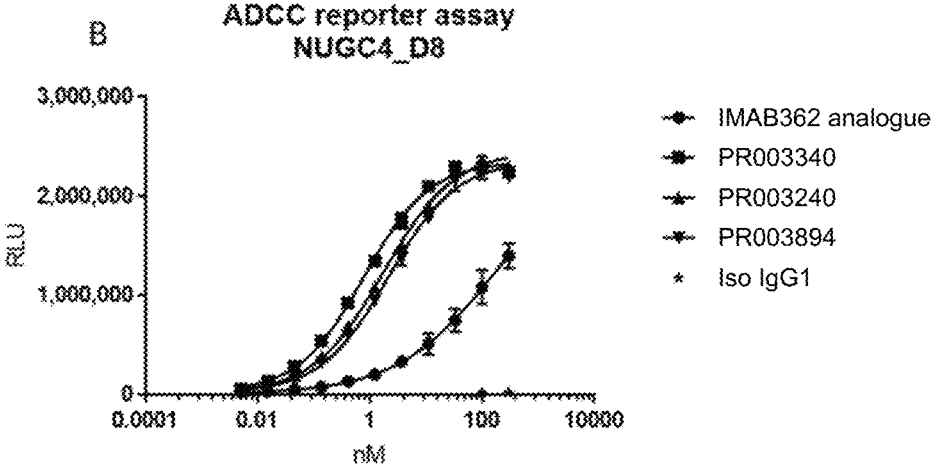
Figure 7:
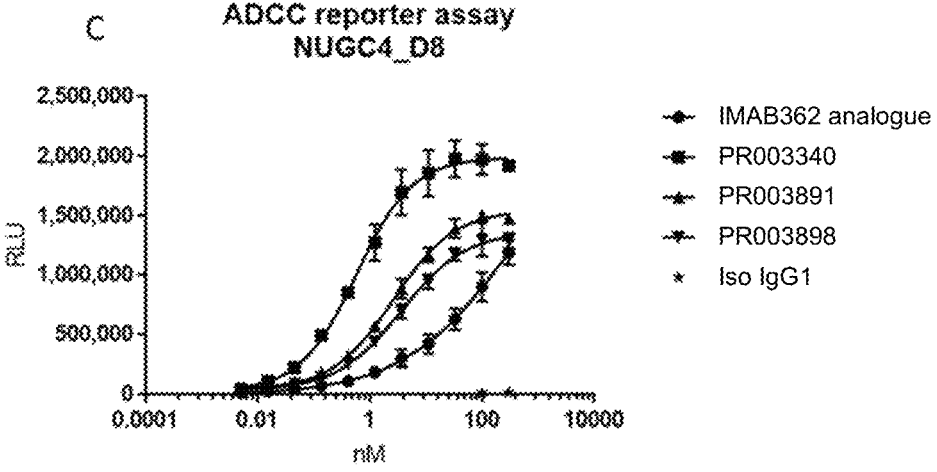

Jurkat FcγRIIIa-V158/NFAT-Luc cells were used to detect the ADCC activity mediated by CLDN18.2 antibody against NUGC4_D8 and HEK293 hCLDN18.1. NUGC4_D8 and HEK293 hCLDN18.1 were centrifuged at 300 g for 5 minutes and then resuspended in RPMI1640+4% FBS serum culture medium. The density of cells was adjusted to $6×10^5$ cells/ml, and 50 μl of cell suspension was added to each well of a 96-well plate, and then incubated at 37° C. overnight. Jurkat FcγRIIIa-V158/NFAT-Luc cells were centrifuged at 400 g for 4 minutes, and then resuspended in RPMI1640+4% FBS serum culture medium. The density of cells was adjusted to $3×10^6$ cells/ml, and 50 μl of cell suspension was added to each well of a 96-well plate. Antibodies were diluted to different concentrations with RPMI1640+4% FBS medium, and 50 μl of antibody dilution was added in each well of a 96-well plate. Cells were incubated with antibody at 37° C. for 5 hours. The 96-well plate was allowed to stand at room temperature for 30 minutes, and 60 l/well of One-Glo chromogenic substrate (Promega) at room temperature was added. The samples were then incubated in the dark at room temperature for 10 minutes. The 96-well plate was read with PE Enspire. IMAB362 analogue was used as positive control, and antibody of human Iso IgG1 (CrownBio, Cat #: C0001-4) was used as negative control. FIG. 7 shows the ADCC activity of CLDN18.2 antibody against NUGC4_D8 cells endogenously expressing CLDN18.2; HBM1029, PR003197, PR003340, PR003240, PR003894, PR003891 and PR003898 were able to mediate stronger ADCC effect in a dose-dependent manner against NUGC4_D8 than the IMAB362 analogue.

Example 6: CDC Activity of CLDN18.2 Antibody

Figure 8:
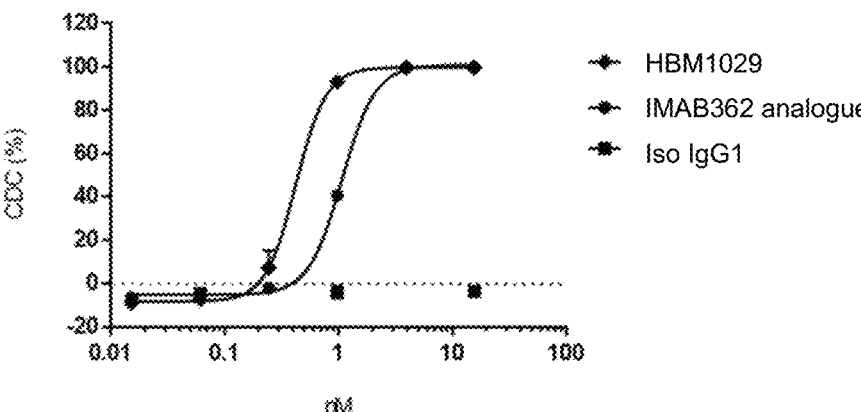
FIG. 8 shows HBM1029 antibody triggered CDC effect in HEK293 hCLDN18.2 cells, HEK293 hCLDN18.1 cells and NUGC4_D8 cells.
Figure 8:
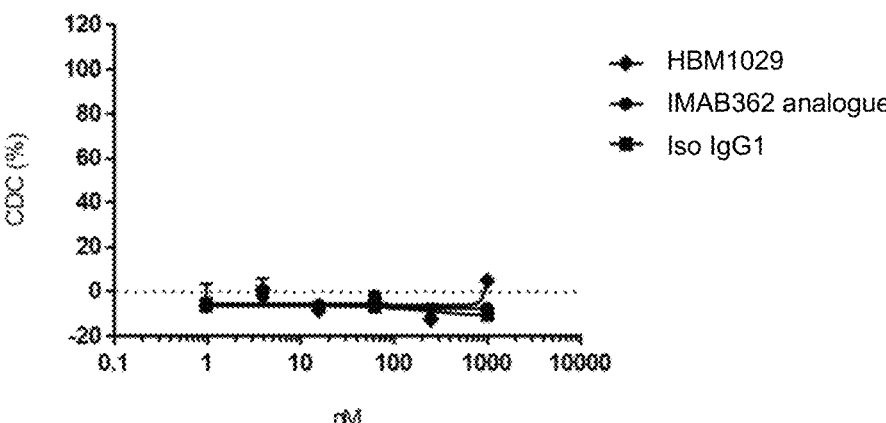
Figure 8:
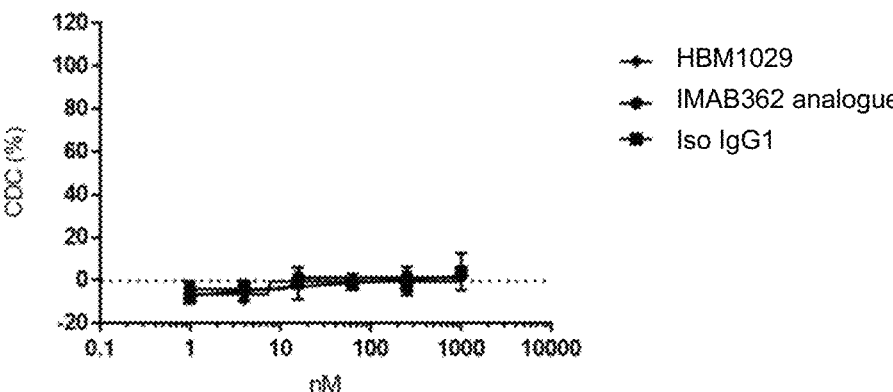

The ability of CLDN18.2 antibodies to mediate CDC effect against HEK293 hCLDN18.1, HEK293 hCLDN18.2 and NUGC4_D8 cells was detected using the CellTiter-Glo luminescent cell viability assay kit (Promega, Cat #: G7573). Target cells HEK293 hCLDN18.1 and HEK293 hCLDN18.2 were centrifuged at 300 g for 5 minutes and then resuspended in DMEM serum-free culture medium. Target cell NUGC4_D8 was centrifuged at 300 g for 5 minutes and then resuspended in RPMI1640 serum-free culture medium. The density of the target cells was adjusted to $4×10^5$ cells/ml, and 25 μl of cell suspension was added to each well of a 96-well plate. Antibodies were diluted to different concentrations with serum-free culture medium, and 25 μl of antibody diluent was added to each well of a 96-well plate. 50 μl of normal human serum (GemCell, Cat #: 100-512) was added at a final concentration of 50%, and the obtained mixture was incubated at 37° C. for 24 hours. The 96-well plate was allowed to stand at room temperature for 30 minutes, and 100 μl/well of room temperature CellTiter-Glo chromogenic substrate was added. Afterwards, the samples were incubated in the dark at room temperature for 10 minutes. The 96-well plate was read with PE Enspire. CDC activity (%)=[1−(luminescent sample)/(luminescent mock control)]×100. IMAB362 analogue was used as positive control and antibody of human Iso IgG1 (CrownBio, Cat #: C0001-4) was used as negative control. FIG. 8 shows the CDC activity of HBM1029 antibody against NUGC4_D8 cells endogenously expressing CLDN18.2, HEK293 cells overexpressing human CLDN18.1, and HEK293 cells overexpressing human CLDN18.2. HBM1029 antibody mediated a stronger CDC effect in a dose-dependent manner on HEK293 hCLDN18.2 than the IMAB362 analogue, while no CDC activity was observed against NUGC4_D8 cells and HEK293 cell overexpressing human CLDN18.1. The $EC_{50}$ value of HBM1029 is shown in Table 9 and the $EC_{50}$ value of HBM1029-mediated CDC against HEK293 hCLDN18.2 was lower than the IMAB362 analogue.

TABLE 9

| | CDC activity of HBM1029 | | |
| --- | --- | --- | --- |
| cell | | HBM1029 | IIVIAB362 analogue |
| HEK293 hCLDN18.2 | Max Lysis (%) | 100.0 | 100.9 |
| | $EC_{50}$ (nM) | 0.42 | 1.07 |

Figure 9:
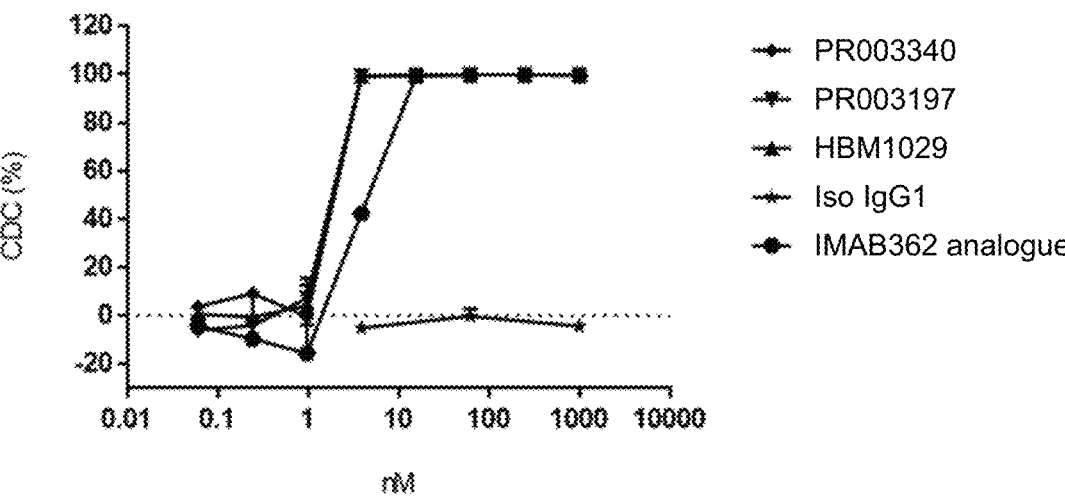
FIG. 9 shows that HBM1029, PR003197 and PR003340 antibodies triggered CDC effect in HEK293 hCLDN18.2 cells.

FIG. 9 shows the CDC activities of PR003197 and PR003340 against HEK293 cells overexpressing human CLDN18.2. PR003197 and PR003340 antibodies mediated a stronger CDC effect in a dose-dependent manner on HEK293 hCLDN18.2 than the IMAB362 analogue.

Example 7: Growth Inhibitory Activity of CLDN18.2 Antibody

Figure 10:
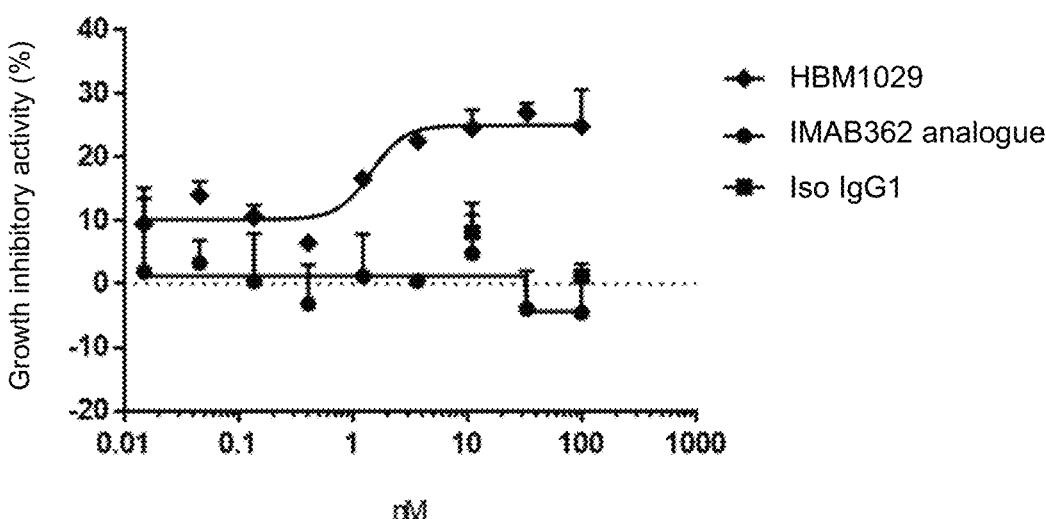
FIG. 10 shows the growth inhibitory activity triggered by HBM1029 antibody in HEK293 hCLDN18.1 cells and HEK293 hCLDN18.2 cells.
Figure 10:
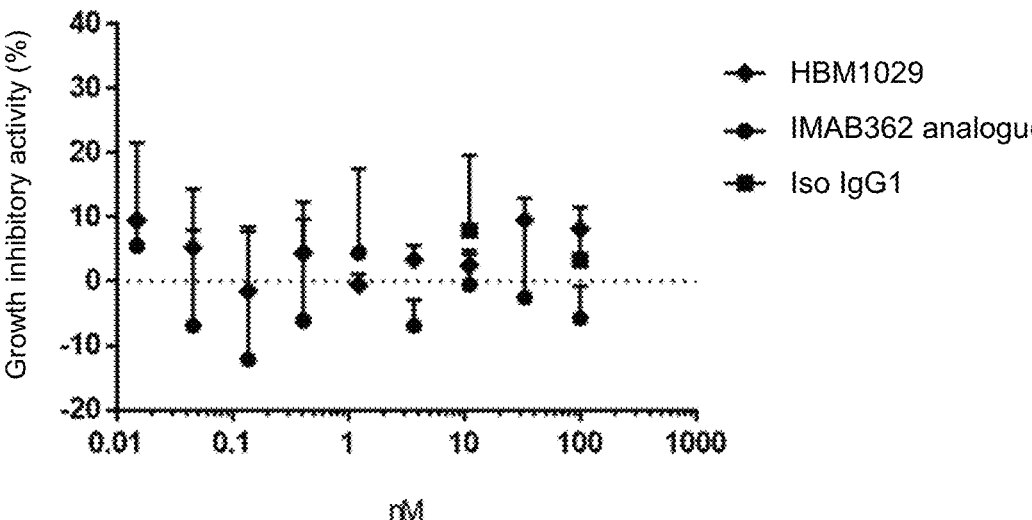

The ability of the CLDN18.2 antibody to induce growth inhibition against HEK293 hCLDN18.1 and HEK293 hCLDN18.2 was detected using the CellTiter-Glo luminescent cell viability assay kit (Promega, Cat #: G7573). Cells HEK293 hCLDN18.1 and HEK293 hCLDN18.2 were centrifuged at 300 g for 5 minutes and then resuspended in DMEM+0.5% FBS serum culture medium. The density of cells was adjusted to $1.2 \times 10^5$ cells/ml, and 50 μl of cell suspension was added to each well of a 96-well plate, and then incubated at 37° C. overnight. Antibodies were diluted to different concentrations with medium, and 50 μl of antibody diluent was added to each well of a 96-well plate. HEK293 hCLDN18.1 and HEK293 hCLDN18.2 cells were incubated with antibodies at 37° C. for 3 days. The 96-well plate was allowed to stand at room temperature for 30 minutes, and 100 μl/well of CellTiter-Glo chromogenic substrate at room temperature was added. Afterwards, the samples were incubated in the dark at room temperature for 10 minutes. The 96-well plate was read with PE Enspire. Growth inhibitory activity (%)=[1−(luminescent sample)/(luminescent mock control)]×100. IMAB362 analogue was used as positive control and antibody of human Iso IgG1 (CrownBio, Cat #: C0001-4) was used as negative control. FIG. 10 shows the growth inhibitory activity induced by HBM1029 antibody against HEK293 hCLDN18.1 and HEK293 hCLDN18.2. HBM1029 antibody induced stronger growth inhibition in a dose-dependent manner against HEK293 hCLDN 18.2 than the IMAB362 analogue. The $EC_{50}$ value of HBM1029 is shown in Table 10.

TABLE 10

| growth inhibitory activity of HBM1029 | | | |
|---|---|---|---|
| cell | | HBM1029 | IMAB362 analogue |
| HEK293 hCLDN18.2 | Max growth inhibition (%) | 25.0 | N/A |
| | $EC_{50}$ (nM) | 1.45 | N/A |

Example 8: Endocytosis (Internalization) Activity of CLDN18.2 Antibody (FACS-Based Assay)

Figure 11:
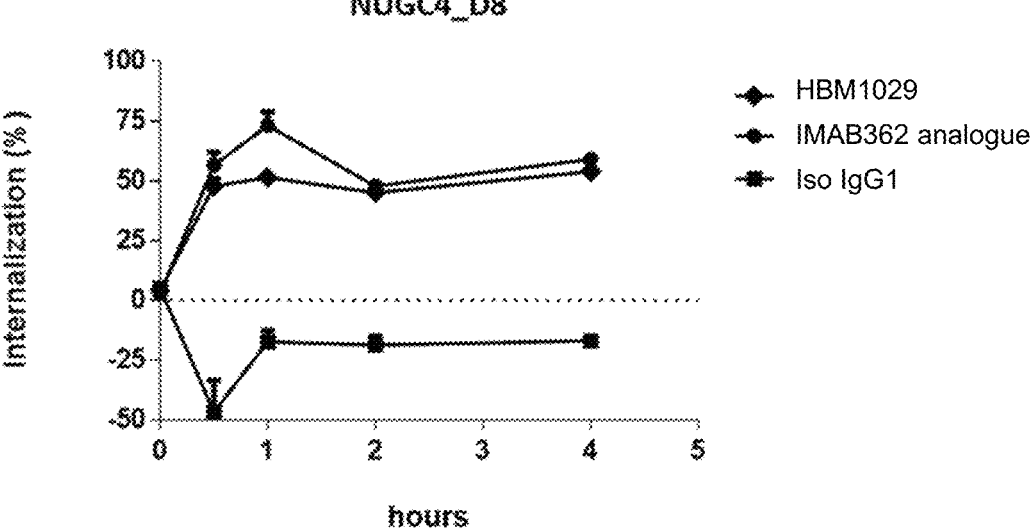
FIG. 11 shows the endocytic activity of HBM1029 anti-body in NUGC4_D8 cells. The results showed that: (A) NUGC4_D8 cells were mixed and incubated with 200 nM antibody for different time periods, and (B) NUGC4_D8 cells were mixed and incubated with different concentrations of antibody for 1 hour.
Figure 11:
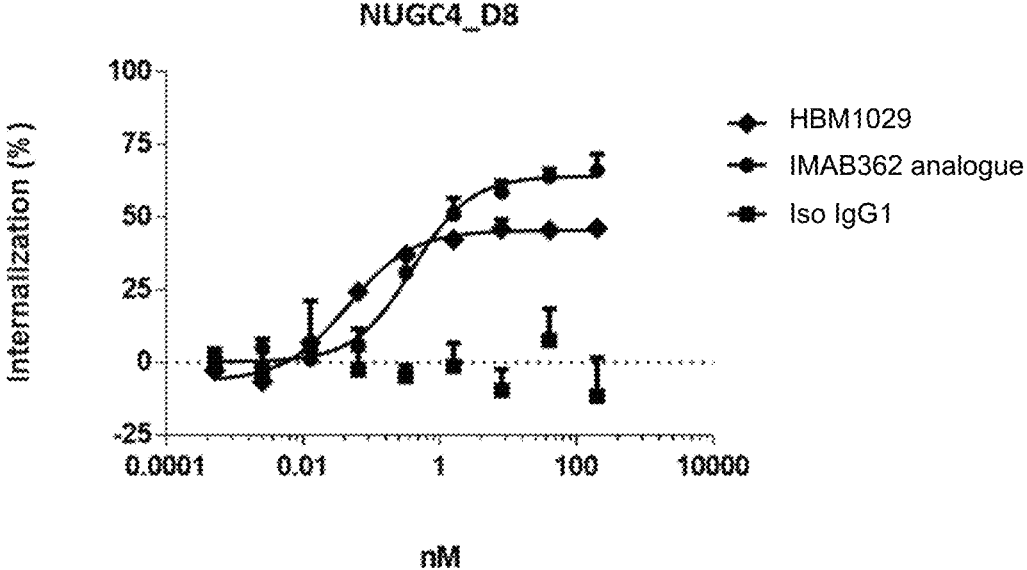

The endocytosis activity of antibodies was detected by FACS using NUGC4_D8 cells. The cells were digested with trypsin and washed once with FACS buffer (PBS containing 2% FBS). The cells were centrifuged at 300 g for 5 minutes and then resuspended in FACS buffer. The density of cells was adjusted to $4 \times 10^6$ cells/ml and pre-cooled on ice for 30 minutes. Antibodies were diluted to different concentrations in FACS buffer and pre-cooled on ice for 30 minutes. 700 μl of cell suspension and 700 μl of antibody diluent were added to the wells of the pre-cooled deep well plate. After incubation at 4° C. for 2 hours, the plate was washed 3 times with pre-cooled FACS buffer. The cells were resuspended with 250 μl pre-cooled FACS buffer, 100 μl of cell suspension and 1.1 ml of 37° C.-pre-heated FACS buffer were added to the wells of a 37° C.-pre-heated deep well plate; 100 μl of cell suspension and 1.1 ml of 4° C.-pre-cooled FACS buffer were added to the wells of a 4° C.-pre-cooled deep well plate. 50 μL of cell suspension ($10^5$ cells/well) was taken from the obtained mixture at 0, 30, 60, 120 and 240 minutes, respectively, and placed in a pre-cooled deep well plate (containing 1.2 ml FACS buffer). The cells were centrifuged at 300 g for 5 minutes, after which pre-cooled FACS buffer containing AF647-conjugated goat anti-human IgG secondary antibody (final concentration 1.5 μg/ml, Jackson, Cat #: 109-605-088) was added. After incubation at 4° C. for 1 hour, the plate was washed 2 times with pre-cooled FACS buffer. The cells were resuspended with fixative, followed by fluorescence detection using a FACS machine (BD Canto II). Endocytosis activity (%)=$(1-MFI_{37° C.}/MFI_{4° C.}) \times 100$. IMAB362 analogue was used as positive control and antibody of human Iso IgG1 (CrownBio, Cat #: C0001-4) was used as negative control. FIG. 11 shows the endocytosis activity of HBM1029 antibody in NUGC4_D8 cells incubated for various times. HBM1029 antibody induced approximately 50% endocytosis activity after incubation for 30 minutes. FIG. 11 also shows that HBM1029 antibody was able to induce higher endocytosis activity in a dose-dependent manner in NUGC4_D8 than the IMAB362 analogue. The $EC_{50}$ value of HBM1029 is shown in Table 11 and the $EC_{50}$ value of endocytosis induced by HBM1029 in NUGC4_D8 was lower than the IMAB362 analogue.

TABLE 11

| endocytosis activity of HBM1029 | | | |
|---|---|---|---|
| cell | | HBM1029 | IMAB362 analogue |
| NUGC4_D8 | Max endocytosis (%) | 45.4 | 64.1 |
| | $EC_{50}$ (nM) | 0.05 | 0.40 |

Example 9: Endocytosis Activity of CLDN18.2 Antibody (Cytotoxicity-Based Method)

Figure 12:
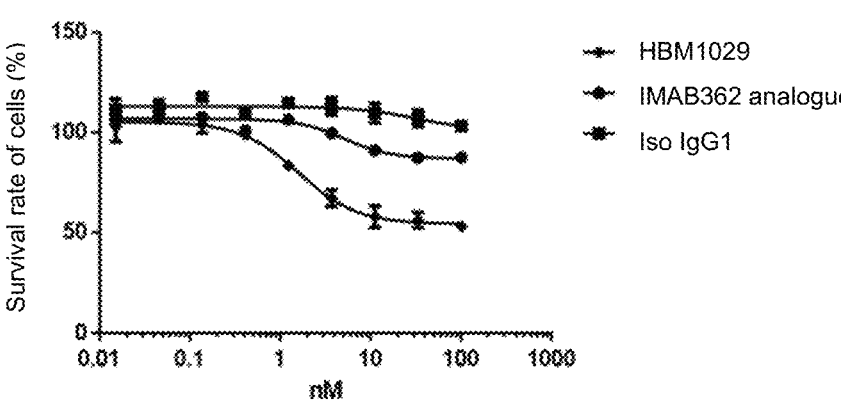
FIG. 12 shows the survival rate of target cells when HBM1029 antibody was co-cultured with anti-human IgG antibody-conjugated MMAF.
Figure 12:
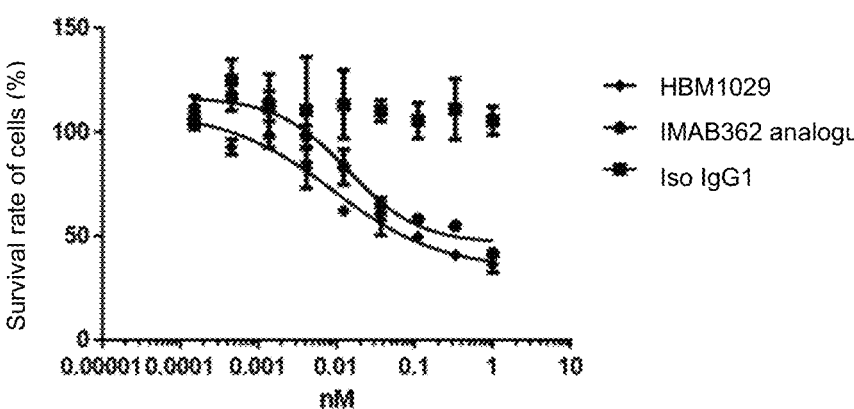
Figure 12:
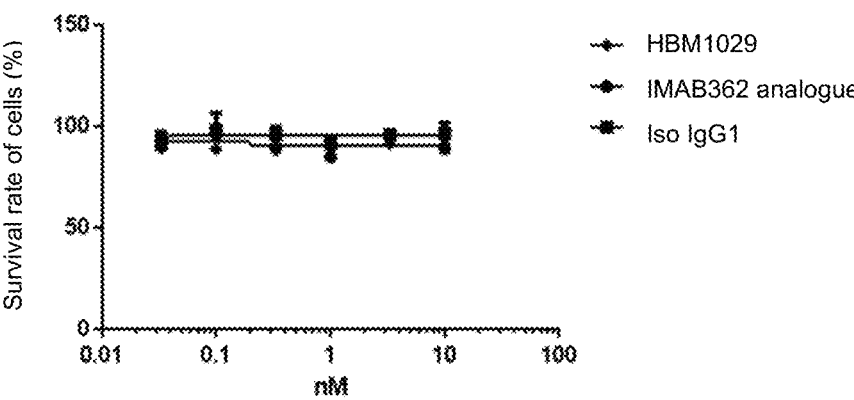

The CellTiter-Glo luminescence cell viability assay kit (Promega, Cat #: G7573) was used to detect the ability of HBM1029 antibody when co-cultured with MMAF-conjugated anti-human IgG antibody (Moradec, Cat #: AH-102-AF) to induce cytotoxicity against HEK293 hCLDN18.1, HEK293 hCLDN18.2 and NUGC4_D8 cells. HEK293 hCLDN18.1 cells and HEK293 hCLDN18.2 cells were centrifuged at 300 g for 5 minutes, and then resuspended in DMEM+10% FBS serum culture medium, and the density of cells was adjusted to $4 \times 10^4$ cells/ml. NUGC4_D8 cells were centrifuged at 300 g for 5 minutes, and then resuspended in RPMI1640+10% FBS serum culture medium, and the density of cells was adjusted to $2 \times 10^4$ cells/ml, and 50 μl cell suspension was added to each well of a 96-well plate and incubated at 37° C. overnight. HBM1029 antibody was diluted to different concentrations with culture medium, and 25 μl of antibody diluent was added to each well in a 96-well plate. MMAF-conjugated anti-human IgG antibody was diluted with culture medium, and 25 μl of antibody diluent was added to each well in a 96-well plate at a final concentration of 6.6 nM. Cells were incubated with antibody at 37° C. for 3 days. The 96-well plate was allowed to stand at room temperature for 30 minutes, and 100 l/well of CellTiter-Glo chromogenic substrate at room temperature was added. Afterwards, the samples were then incubated in the dark at room temperature for 10 minutes. The 96-well plate was read with PE Enspire. Cell viability (%)=[(luminescent sample)/(luminescent mock control)]×100. IMAB362 analogue was used as positive control and antibody of human Iso IgG1 (CrownBio, Cat #: C0001-4) was used as negative control. FIG. 12 shows the survival rate of target cells when HBM1029 antibody was co-cultured with MMAF-conjugated anti-human IgG antibody. HBM1029 antibody co-cultured with MMAF-conjugated anti-human IgG antibody induced a stronger cytotoxic effect in a dose-dependent manner on NUGC4_D8 cells and HEK293 hCLDN18.2 cells than the IMAB362 analogue, but no cytotoxic effect on HEK293 hCLDN18.1 cells.

Example 10: Competitive Binding Activity of HBM1029 Antibody

Figure 13:
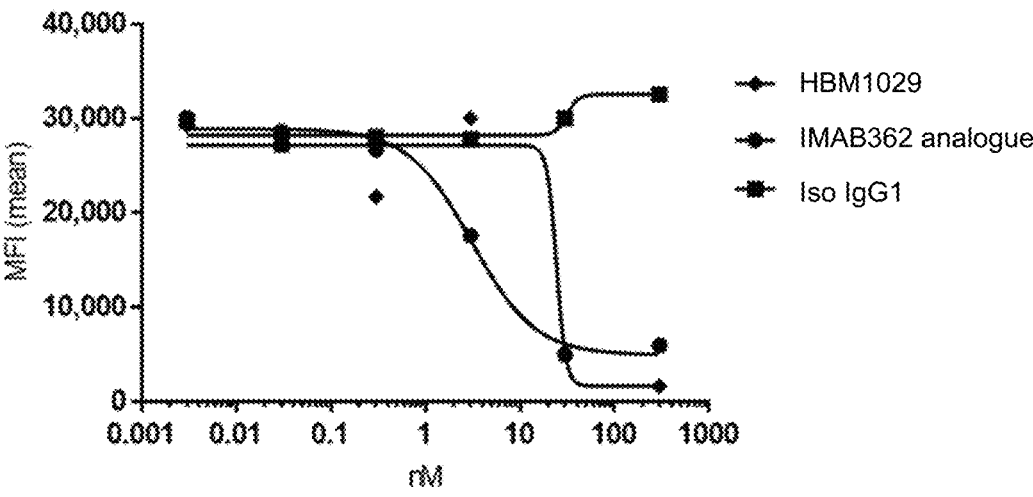
FIG. 13 shows the competitive binding affinity of HBM1029 antibody to IMAB362-FITC analogue in HEK293 hCLDN18.2 cells. Different concentrations of HBM1029 antibody were mixed and incubated with 20 nM IMAB362-FITC analogue and HEK293 hCLDN18.2 cells.

The competitive binding affinity of antibody was detected by FACS using HEK293 cells expressing human CLDN18.2. IMAB362 analogue was conjugated as IMAB362-FITC analogue using the FITC Fluorescence Conjugation Kit (Abcam, Cat #: ab188285). Cells were centrifuged at 300 g for 5 minutes and then resuspended in FACS buffer (PBS containing 2% FBS). The density of cells was adjusted to $10^6$ cells/ml, and 50 μl of cell suspension was added to each well of a 96-well plate. The FITC-conjugated antibody was diluted with FACS buffer, and 50 μl of the conjugated antibody diluent was added to each well of a 96-well plate. Antibody for competitive binding was diluted to different concentrations with FACS buffer, and 50 μl of antibody dilution was added to each well of a 96-well plate. After incubation at 4° C. for 2 hours, the plate was washed 2 times with FACS buffer. The cells were resuspended with fixative, after which the fluorescence of the cells was monitored using a FACS machine (ACEA Novo-Cyte). Antibody of human Iso IgG1 (CrownBio, Cat #: C0001-4) was used as negative control. FIG. 13 illustrates the competitive binding affinity of HBM1029 antibody to HEK293 hCLDN 18.2 cells than the IMAB362-FITC. HBM1029 antibody was able to bind competitively to HEK293 hCLDN 18.2 cells in a dose-dependent manner, presumably with similar binding epitopes to the IMAB362 analogue. HBM1029 competed with the IMAB362 analogue and inhibit its binding to CLDN18.2-expressing cells; whereas the IMAB362 analogue is known to bind only to CLDN18.2 and not to CLDN18.1. Therefore, it is hypothesized that HBM1029 binds to ECL1 (extracellular loop 1) of human CLDN18.2 protein instead of ECL2.

Example 11: Pharmacokinetic Study of CLDN18.2 Antibody

The pharmacokinetics of CLDN18.2 antibody was determined as follows: 6 female BALB/c nude mice weighing 18-22 g were administered the antibody drug by intravenous injection at a dose of 5 mg/kg; whole blood was collected from one group of 3 mice before administration and 15 minutes, 24 hours (1 day), 4 days, and 10 days after administration, respectively, and from another group of 3 mice only before administration and 5 hours, 2 days, 7 days, and 14 days after administration. Whole blood was allowed to stand for 30 minutes to coagulate, then centrifuged at 2,000 rpm for 5 minutes at 4° C. to collect isolated serum samples which were then frozen at −80° C. until analysis. The ELISA method was used to quantify drug concentrations in mouse serum. In the ELISA method, the antibody containing human Fc in mouse serum was captured by a goat anti-human Fc polyclonal antibody coated in a 96-well plate, and then HRP-labeled goat anti-human Fc secondary antibody was added for detection. Blood concentration data were analyzed using Phoenix WinNonlin software version 8.2, and the non-atrioventricular model (NCA) was chosen to evaluate the pharmacokinetic parameters.

Figure 14:
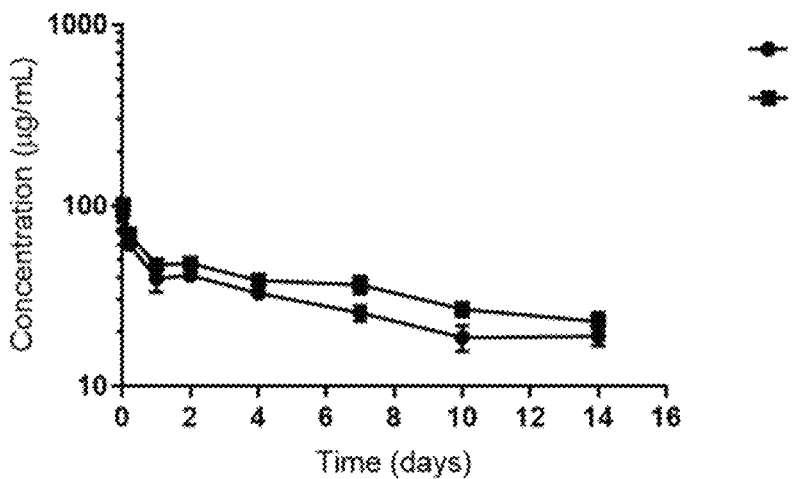
FIG. 14 shows the pharmacokinetic profile of the IMAB362 analogue and HBM1029.

FIG. 14 and Table 12 show the pharmacokinetic parameters of IMAB362 analogue and HBM1029. The results showed that the half-lives of IMAB362 analogue and HBM1029 in mice were 248 and 282 hours, respectively.

TABLE 12 pharmacokinetic parameters of IMAB362 analogue and HBM1029

|  | IMAB362 analogue | HBM1029 |
|---|---|---|
| $T_{1/2}$ (hr) | 248 | 282 |
| $V_d$ (ml/kg) | 112 | 94 |
| $AUC_{all}$ (μg/ml hr) | 9,542 ± 0385 | 12,062 ± 0418 |
| $C_1$ (ml/hr/kg) | 0.32 | 0.24 |
| $C_0$ (μg/ml) | 90 | 104 |

Example 11: In Vivo Pharmacodynamic Study of CLDN18.2 Antibody

Figure 15:
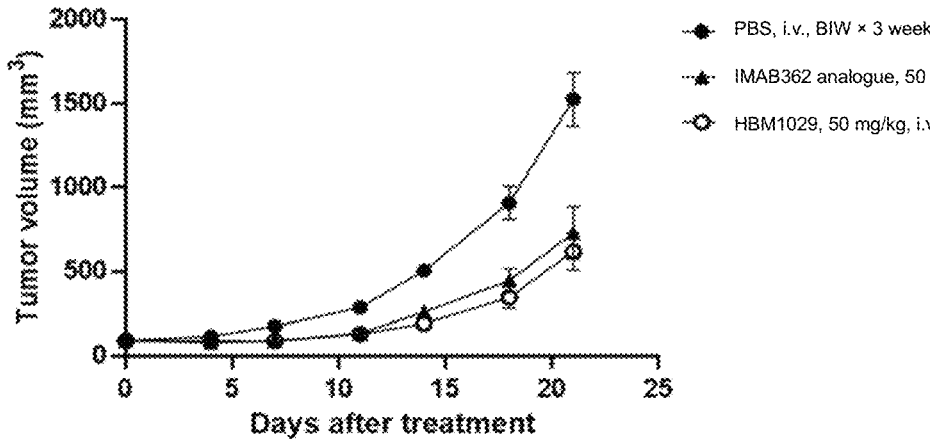
FIG. 15 shows a study on in vivo pharmacokinetics of the IMAB362 analogue and HBM1029.

In vivo pharmacodynamic study of CLDN18.2 antibody was performed as follows: on the day of cell inoculation, each NCG mouse was subcutaneously inoculated with $5×10^6$ NUGC4_D8 tumor cells, which were firstly resuspended in a mixture solution (0.1 ml) of PBS and Matrigel (1:1), and then mixed with PBMC (resuspended in 0.05 ml of PBS) and inoculated subcutaneously. When the average tumor volume of mice in each group was 90 $mm^3$, the mice were grouped, and 18 mice were divided into three groups; administration began after the grouping; the drug administration cycle was twice a week with a total of six times of administration; the drug administration method was tail vein injection. After start of administration, the body weight of mouse was weighed and tumor volume was measured twice a week; the tumor volume was calculated as follows: tumor volume $(mm^3)$=0.5×tumor long diameter×tumor short diameter$^2$. The experimental observation was ended on day 21 after administration, and all mice were then euthanized. Data were analyzed by t-test. FIG. 15 shows the results of the in vivo pharmacodynamic study of IMAB362 analogue and HBM1029. The mean tumor volume of control mice was 1526 $mm^3$ on day 21 after administration. The mean tumor volume of the test drug IMAB362 analogue (50 mg/kg) treated mice was 728 $mm^3$ on day 21 after administration, with a significant difference compared to the vehicle control group (p-value of 0.0052) and a tumor growth inhibition (TGI) rate of 52.29%. The mean tumor volume of the test drug HBM1029 (50 mg/kg) treated mice was 618 $mm^3$ on day 21 after administration, with a significant tumor inhibition effect compared to the vehicle control group (p-value 0.0009) and a tumor growth inhibition (TGI) rate of 59.47%. Throughout the administration period in treatment, the animals showed good drug tolerance and there were no significant body weight loss and animal death.

Although the specific embodiments of the present invention have been described above, it should be understood by those skilled in the art that these are merely illustrative examples and that a variety of changes or modifications can be made to these embodiments without departing from the principles and spirits of the present invention. Therefore, the scope of protection of the present invention is limited by the appended claims.

What is claimed is:

1. An antibody targeting CLDN18.2 or an antigen-binding fragment thereof, comprising a light chain variable region and a heavy chain variable region, the heavy chain variable region comprises HCDR1, HCDR2 and HCDR3, the light chain variable region comprises LCDR1, LCDR2 and LCDR3; wherein, amino acid sequence of the HCDR1 is SEQ ID NO: 7, amino acid sequence of the HCDR2 is SEQ ID NO: 17, amino acid sequence of the HCDR3 is SEQ ID NO: 27, and amino acid sequence of the LCDR1 is SEQ ID NO: 41, amino acid sequence of the LCDR2 is SEQ ID NO: 48, and amino acid sequence of the LCDR3 is SEQ ID NO: 56; or, amino acid sequence of the HCDR1 is SEQ ID NO: 8, amino acid sequence of the HCDR2 is SEQ ID NO: 18, amino acid sequence of the HCDR3 is SEQ ID NO: 28, and amino acid sequence of the LCDR1 is SEQ ID NO: 42, amino acid sequence of the LCDR2 is SEQ ID NO: 47, and amino acid sequence of the LCDR3 is SEQ ID NO: 57; or, amino acid sequence of the HCDR1 is SEQ ID NO: 8, amino acid sequence of the HCDR2 is SEQ ID NO: 16, amino acid sequence of the HCDR3 is SEQ ID NO: 29, and amino acid sequence of the LCDR1 is SEQ ID NO: 42, amino acid sequence of the LCDR2 is SEQ ID NO: 47, and amino acid sequence of the LCDR3 is SEQ ID NO: 55; or, amino acid sequence of the HCDR1 is SEQ ID NO: 8, amino acid sequence of the HCDR2 is SEQ ID NO: 16, amino acid sequence of the HCDR3 is SEQ ID NO: 29, and amino acid sequence of the LCDR1 is SEQ ID NO: 42, amino acid sequence of the LCDR2 is SEQ ID NO: 47, and amino acid sequence of the LCDR3 is SEQ ID NO: 58; or, amino acid sequence of the HCDR1 is SEQ ID NO: 8, amino acid sequence of the HCDR2 is SEQ ID NO: 19, amino acid sequence of the HCDR3 is SEQ ID NO: 28, amino acid sequence of the LCDR1 is SEQ ID NO: 42, amino acid sequence of the LCDR2 is SEQ ID NO: 47, and amino acid sequence of the LCDR3 is SEQ ID NO: 57.

2. The antibody targeting CLDN18.2 or the antigen-binding fragment thereof of claim 1, wherein, the heavy chain variable region comprises the amino acid sequence of SEQ ID NO: 64 or a variant thereof, and the light chain variable region comprises the amino acid sequence of SEQ ID NO: 71 or a variant thereof;

or, the heavy chain variable region comprises the amino acid sequence of SEQ ID NO: 67 or a variant thereof, and the light chain variable region comprises the amino acid sequence of SEQ ID NO: 73 or a variant thereof;

or, the heavy chain variable region comprises the amino acid sequence of SEQ ID NO: 65 or a variant thereof, and the light chain variable region comprises the amino acid sequence of SEQ ID NO: 72 or a variant thereof;

or, the heavy chain variable region comprises the amino acid sequence of SEQ ID NO: 68 or a variant thereof, and the light chain variable region comprises the amino acid sequence of SEQ ID NO: 74 or a variant thereof;

or, the heavy chain variable region comprises the amino acid sequence of SEQ ID NO: 66 or a variant thereof, and the light chain variable region comprises the amino acid sequence of SEQ ID NO: 72 or a variant thereof;

wherein, the variant retains at least function of pre-mutated sequence, and the variant has at least 85% identity to the pre-mutated sequence.

3. The antibody targeting CLDN18.2 or the antigen-binding fragment thereof of claim 1, wherein, the antibody targeting CLDN18.2 further comprises an antibody heavy chain constant region and an antibody light chain constant region.

4. The antibody targeting CLDN18.2 or the antigen-binding fragment thereof of claim 3, which is a full-length antibody comprising a heavy chain and a light chain; wherein, the heavy chain comprises the amino acid sequence of SEQ ID NO: 77, and the light chain comprises the amino acid sequence of SEQ ID NO: 93;

or, the heavy chain comprises the amino acid sequence of SEQ ID NO: 78, and the light chain comprises the amino acid sequence of SEQ ID NO: 94;

or, the heavy chain comprises the amino acid sequence of SEQ ID NO: 79, and the light chain comprises the amino acid sequence of SEQ ID NO: 93;

or, the heavy chain comprises the amino acid sequence of SEQ ID NO: 85, and the light chain comprises the amino acid sequence of SEQ ID NO: 93;

or, the heavy chain comprises the amino acid sequence of SEQ ID NO: 83, and the light chain comprises the amino acid sequence of SEQ ID NO: 93;

or, the heavy chain comprises the amino acid sequence of SEQ ID NO: 84, and the light chain comprises the amino acid sequence of SEQ ID NO: 93;

or, the heavy chain comprises the amino acid sequence of SEQ ID NO: 81, and the light chain comprises the amino acid sequence of SEQ ID NO: 95;

or, the heavy chain comprises the amino acid sequence of SEQ ID NO: 82, and the light chain comprises the amino acid sequence of SEQ ID NO: 96;

or, the heavy chain comprises the amino acid sequence of SEQ ID NO: 80, and the light chain comprises the amino acid sequence of SEQ ID NO: 94;

or, the heavy chain comprises the amino acid sequence of SEQ ID NO: 86, and the light chain comprises the amino acid sequence of SEQ ID NO: 95;

or, the heavy chain comprises the amino acid sequence of SEQ ID NO: 87, and the light chain comprises the amino acid sequence of SEQ ID NO: 96;

or, the heavy chain comprises the amino acid sequence of SEQ ID NO: 88, and the light chain comprises the amino acid sequence of SEQ ID NO: 94;

or, the heavy chain comprises the amino acid sequence of SEQ ID NO: 89, and the light chain comprises the amino acid sequence of SEQ ID NO: 95;

or, the heavy chain comprises the amino acid sequence of SEQ ID NO: 90, and the light chain comprises the amino acid sequence of SEQ ID NO: 96.

5. A biomaterial encoding the antibody targeting CLDN18.2 or the antigen-binding fragment thereof of claim 1, wherein, the biomaterial is selected from the group consisting of:

(i) an isolated nucleic acid;

(ii) a recombinant expression vector comprising the isolated nucleic acid of (i);

(iii) a transformant, which is a host cell comprising the recombinant expression vector of (ii).

6. A medicament comprising the antibody targeting CLDN18.2 or the antigen-binding fragment thereof of claim 1, wherein, the medicament is selected from the group consisting of: (i) a chimeric antigen receptor; (ii) a genetically modified cell; (iii) an antibody drug conjugate; wherein the antibody drug conjugate further comprises a cytotoxic agent; (iv) a pharmaceutical composition, wherein, the pharmaceutical composition further comprises a pharmaceutically acceptable carrier.

7. A kit comprising the antibody targeting CLDN18.2 or the antigen-binding fragment thereof of claim 1.

8. A method for diagnosing or treating a CLDN18.2-mediated disease or symptom, which comprises: administering to a subject in need of a therapeutically effective amount of the antibody targeting CLDN18.2 or the antigen-binding fragment thereof of claim 1; the disease or symptom is a tumor.

9. A method of immunoassaying or measuring CLDN18.2, which comprises the antibody targeting CLDN18.2 or the antigen-binding fragment thereof of claim 1.

10. A combination therapy, which comprises: administering the antibody targeting CLDN18.2 or the antigen-binding fragment thereof of claim 1 and a second therapeutic agent, respectively, to a subject in need; the second therapeutic agent comprises other anti-tumor antibodies or a pharmaceutical composition containing the other anti-tumor antibodies, or one or more of the group consisting of hormone agents, targeted small molecule agents, proteasome inhibitors, imaging agents, diagnostic agents, chemotherapeutic agents, oncolytic drugs, cytotoxic agents, cytokines, activators of co-stimulatory molecules, inhibitors of inhibitory molecules and vaccines.

11. The antibody targeting CLDN18.2 or the antigen-binding fragment thereof of claim 7, wherein the heavy chain constant region is selected from hIgG1, hIgG2, hIgG3 or hIgG4 or variants thereof, and the light chain constant region is selected from κ chain or λ chain of a human antibody or variants thereof.

12. The antibody targeting CLDN18.2 or the antigen-binding fragment thereof of claim 11, wherein the heavy chain constant region is hIgG1, and the light chain constant region is κ chain of a human antibody.

13. The antibody targeting CLDN18.2 or the antigen-binding fragment thereof of claim 3, wherein the antibody targeting CLDN18.2 is a full-length antibody, a Fab, a Fab', a F(ab')$_2$, a Fv, a scFv, a bispecific antibody, a multispecific antibody, or a monoclonal antibody or a polyclonal antibody derived from the antibody as defined above.

14. The biomaterial according to claim 5, wherein the recombinant expression vector is a plasmid, a cosmid, a phage or a viral vector;

or, the host cell is an *E. coli* TG1, a BL21 cell or a CHO-K1 cell.

15. The medicament of claim 6, wherein the genetically modified cell is a eukaryotic cell;

wherein the cytotoxic agent is MMAF or MMAE;

wherein the pharmaceutical composition further comprises one or more of the group consisting of hormone agents, targeted small molecule agents, proteasome inhibitors, imaging agents, diagnostic agents, chemotherapeutic agents, oncolytic drugs, cytotoxic agents, cytokines, activators of co-stimulatory molecules, inhibitors of inhibitory molecules and vaccines.

16. The medicament of claim 15, wherein the genetically modified cell is an isolated human immune cell.

17. The kit according to claim 7, wherein the kit further comprises (i) a device for administering an antibody or an antigen binding fragment thereof, or an antibody drug conjugate or a pharmaceutical composition; or (ii) instructions for use.

18. The method according to claim 8, wherein the tumor is a CLDN18.2 positive tumor.

19. The method according to claim 18, wherein the CLDN18.2 positive tumor is gastric cancer, esophageal cancer, lung cancer, ovarian cancer, melanoma, renal cancer, breast cancer, colorectal cancer, liver cancer, pancreatic cancer, bladder cancer, head and neck cancer, bronchial cancer, glioma or leukemia.

\* \* \* \* \*